(12) United States Patent
Muse

(10) Patent No.: US 11,191,550 B2
(45) Date of Patent: Dec. 7, 2021

(54) MEDICAL DRILLING DEVICES AND RELATED SYSTEMS AND METHODS

(71) Applicant: Piper Access, LLC, Salt Lake City, UT (US)

(72) Inventor: Jay Allen Muse, Salt Lake City, UT (US)

(73) Assignee: Piper Access, LLC, Salt Lake City, UT (US)

( * ) Notice: Subject to any disclaimer, the term of this patent is extended or adjusted under 35 U.S.C. 154(b) by 276 days.

(21) Appl. No.: 16/280,897

(22) Filed: Feb. 20, 2019

(65) Prior Publication Data

US 2019/0282244 A1 Sep. 19, 2019

Related U.S. Application Data

(60) Provisional application No. 62/632,554, filed on Feb. 20, 2018.

(51) Int. Cl.
*A61B 17/16* (2006.01)
*A61C 3/02* (2006.01)

(52) U.S. Cl.
CPC ...... *A61B 17/1631* (2013.01); *A61B 17/1624* (2013.01); *A61B 17/1626* (2013.01); *A61C 3/02* (2013.01)

(58) Field of Classification Search
CPC ............ A61B 17/1615; A61B 17/1617; A61B 17/1622; A61B 17/1624; A61B 17/1626;
(Continued)

(56) References Cited

U.S. PATENT DOCUMENTS 1,436,707 A 11/1922 Gaschke
2,317,648 A 4/1943 Siqveland
(Continued)

FOREIGN PATENT DOCUMENTS

CA 2207561 6/1997
DE 102007005963 A1 8/2008
(Continued)

OTHER PUBLICATIONS

PCT International Searching Authority, Notification of Transmittal of the International Search Report and the Written Opinion of the International Searching Authority for International Application No. PCT/US17/57270, dated Jan. 12, 2018, 12 pages.
(Continued)

*Primary Examiner* — Si Ming Ku
(74) *Attorney, Agent, or Firm* — Med Venture Management, LLC; Daniel C. Higgs

(57) ABSTRACT

A medical driver can include a handle coupled to a drive shaft. The drive shaft can couple with an access assembly for drilling into bone, and can be displaced relative to the handle from a rotationally restricted state, in which the drive shaft is rotationally restricted relative to the handle, to a drilling state, in which the drive shaft is freely rotatable in at least one direction relative to the handle. The medical driver can further include a mechanical energy-storage device coupled to the drive shaft that can automatically rotate the drive shaft relative to the handle upon transition of the drive shaft to the drilling state. A biasing element can be coupled to the handle and to the drive shaft to provide a bias to maintain the drive shaft in the rotationally restricted state. When distal movement of the drive shaft is opposed, application of a distally directed force on the handle in an amount sufficient to overcome the bias of the biasing element can transition the drive shaft to the drilling state to automatically permit the (Continued)

energy-storage device to rotate the drive shaft relative to the handle.

20 Claims, 34 Drawing Sheets

(58) Field of Classification Search
CPC . A61B 17/1631; A61B 17/1633; A61B 17/17; A61C 3/02
USPC .......................................................... 408/10
See application file for complete search history.

(56) References Cited

U.S. PATENT DOCUMENTS

| | | | |
|---|---|---|---|
| 4,275,721 A | 6/1981 | Olson | |
| 4,321,914 A | 3/1982 | Begovac et al. | |
| 4,356,828 A | 11/1982 | Jamshidi | |
| 4,469,109 A | 9/1984 | Mehl | |
| 4,593,681 A | 6/1986 | Soni | |
| 4,736,742 A | 4/1988 | Alexson et al. | |
| 4,755,170 A | 7/1988 | Golden | |
| 4,755,173 A | 7/1988 | Konopka et al. | |
| 4,758,225 A | 7/1988 | Cox et al. | |
| 4,889,529 A | 12/1989 | Haindl | |
| 4,929,241 A | 5/1990 | Kulli | |
| 4,944,677 A | 7/1990 | Alexandre | |
| 4,952,207 A | 8/1990 | Lemieux | |
| 4,964,854 A | 10/1990 | Luther | |
| 4,969,870 A | 11/1990 | Kramer et al. | |
| 4,978,344 A | 12/1990 | Dombrowski et al. | |
| 5,040,542 A | 8/1991 | Gray | |
| 5,042,558 A | 8/1991 | Hussey et al. | |
| 5,049,136 A | 9/1991 | Johnson | |
| 5,053,017 A | 10/1991 | Chamuel | |
| 5,073,169 A | 12/1991 | Raiken | |
| 5,120,321 A | 6/1992 | Oksman et al. | |
| 5,122,114 A | 6/1992 | Miller et al. | |
| 5,135,504 A | 8/1992 | McLees | |
| 5,137,520 A | 8/1992 | Maxson et al. | |
| 5,183,468 A | 2/1993 | McLees | |
| 5,207,697 A | 5/1993 | Carusillo et al. | |
| 5,215,528 A | 6/1993 | Purdy et al. | |
| 5,263,939 A | 11/1993 | Wortrich | |
| 5,271,744 A | 12/1993 | Kramer et al. | |
| 5,279,591 A | 1/1994 | Simon | |
| 5,300,045 A | 4/1994 | Plassche, Jr. | |
| 5,304,151 A | 4/1994 | Kuracina | |
| 5,312,351 A | 5/1994 | Gerrone | |
| 5,312,364 A | 5/1994 | Jacobs | |
| 5,322,517 A | 6/1994 | Sircom et al. | |
| 5,328,482 A | 7/1994 | Sircom et al. | |
| 5,332,398 A | 7/1994 | Miller et al. | |
| 5,334,158 A | 8/1994 | McLees | |
| 5,344,408 A | 9/1994 | Partika | |
| 5,348,544 A | 9/1994 | Sweeney et al. | |
| 5,354,283 A | 10/1994 | Bark et al. | |
| 5,357,974 A | 10/1994 | Baldridge | |
| 5,364,367 A | 11/1994 | Banks et al. | |
| 5,366,446 A | 11/1994 | Tal et al. | |
| 5,368,046 A | 11/1994 | Scarfone et al. | |
| 5,375,588 A | 12/1994 | Yoon | |
| 5,405,348 A | 4/1995 | Anspach, Jr. et al. | |
| 5,423,766 A | 6/1995 | Di Cesare | |
| 5,431,655 A | 7/1995 | Melker et al. | |
| 5,449,370 A | 9/1995 | Vaitekunas | |
| 5,451,210 A | 9/1995 | Kramer et al. | |
| 5,458,658 A | 10/1995 | Sircom | |
| 5,472,427 A | 12/1995 | Rammler | |
| 5,533,974 A | 7/1996 | Gaba | |
| 5,554,154 A | 9/1996 | Rosenberg | |
| 5,556,411 A | 9/1996 | Taoda et al. | |
| 5,558,651 A | 9/1996 | Crawford et al. | |
| 5,562,633 A | 10/1996 | Wozencroft | |
| 5,571,133 A | 11/1996 | Yoon | |
| 5,584,810 A | 12/1996 | Brimhall | |
| 5,591,188 A | 1/1997 | Waisman | |
| 5,601,559 A | 2/1997 | Melker et al. | |
| 5,662,610 A | 9/1997 | Sircom | |
| 5,667,509 A | 9/1997 | Westin | |
| 5,683,378 A | 11/1997 | Christy | |
| 5,697,907 A | 12/1997 | Gaba | |
| 5,779,708 A | 7/1998 | Wu | |
| 5,807,275 A | 9/1998 | Jamshidi | |
| 5,882,337 A | 3/1999 | Bogert et al. | |
| 6,001,080 A | 12/1999 | Kuracina et al. | |
| 6,004,294 A | 12/1999 | Brimhall et al. | |
| 6,071,284 A | 6/2000 | Fox | |
| 6,077,244 A | 6/2000 | Botich et al. | |
| 6,117,108 A | 9/2000 | Woehr et al. | |
| 6,132,401 A | 10/2000 | Van Der Meyden et al. | |
| 6,135,769 A | 10/2000 | Kwan | |
| 6,183,442 B1 | 2/2001 | Athanasiou et al. | |
| 6,228,088 B1 | 5/2001 | Miller et al. | |
| 6,247,928 B1 | 6/2001 | Meller et al. | |
| 6,273,715 B1 | 8/2001 | Meller et al. | |
| 6,287,278 B1 | 9/2001 | Woehr et al. | |
| 6,443,927 B1 | 9/2002 | Cook | |
| 6,443,929 B1 | 9/2002 | Kuracina et al. | |
| 6,585,704 B2 | 7/2003 | Luther et al. | |
| 6,595,955 B2 | 7/2003 | Ferguson et al. | |
| 6,616,630 B1 | 9/2003 | Woehr et al. | |
| 6,623,458 B2 | 9/2003 | Woehr et al. | |
| 6,626,887 B1 | 9/2003 | Wu | |
| 6,629,959 B2 | 10/2003 | Kuracina et al. | |
| 6,652,486 B2 | 11/2003 | Bialecki et al. | |
| 6,652,490 B2 | 11/2003 | Howell | |
| 6,699,242 B2 | 3/2004 | Heggeness | |
| 6,749,588 B1 | 6/2004 | Howell et al. | |
| 6,761,726 B1 | 7/2004 | Findlay et al. | |
| 6,796,962 B2 | 9/2004 | Ferguson et al. | |
| 6,814,734 B2 | 11/2004 | Chappuis et al. | |
| 6,860,871 B2 | 3/2005 | Kuracina et al. | |
| 6,875,219 B2 | 4/2005 | Arramon et al. | |
| 6,902,546 B2 | 6/2005 | Ferguson | |
| 6,984,213 B2 | 1/2006 | Horner et al. | |
| 7,004,927 B2 | 2/2006 | Ferguson et al. | |
| 7,008,402 B2 | 3/2006 | Ferguson et al. | |
| 7,070,580 B2 | 7/2006 | Nielsen | |
| 7,179,244 B2 | 2/2007 | Smith et al. | |
| 7,226,434 B2 | 6/2007 | Carlyon et al. | |
| 7,264,613 B2 | 9/2007 | Woehr et al. | |
| 7,341,573 B2 | 3/2008 | Ferguson et al. | |
| 7,354,422 B2 | 4/2008 | Riesenberger et al. | |
| 7,357,784 B2 | 4/2008 | Ferguson | |
| 7,413,562 B2 | 8/2008 | Ferguson et al. | |
| 7,458,954 B2 | 12/2008 | Ferguson et al. | |
| 7,524,306 B2 | 4/2009 | Botich et al. | |
| 7,588,559 B2 | 9/2009 | Aravena et al. | |
| 7,601,139 B2 | 10/2009 | Woehr et al. | |
| 7,611,485 B2 | 11/2009 | Ferguson | |
| 7,618,395 B2 | 11/2009 | Ferguson | |
| 7,670,328 B2 | 3/2010 | Miller | |
| 7,699,808 B2 | 4/2010 | Marrs et al. | |
| 7,699,850 B2 | 4/2010 | Miller | |
| 7,749,225 B2 | 7/2010 | Chappuis et al. | |
| 7,811,260 B2 | 10/2010 | Miller et al. | |
| 7,815,642 B2 | 10/2010 | Miller | |
| 7,850,620 B2 | 12/2010 | Miller et al. | |
| 7,935,080 B2 | 5/2011 | Howell et al. | |
| 7,967,792 B2 | 6/2011 | Bierman | |
| 7,972,339 B2 | 7/2011 | Nassiri et al. | |
| 8,038,664 B2 | 10/2011 | Miller et al. | |
| 8,043,229 B2 | 10/2011 | Mulvihill et al. | |
| 8,096,973 B2 | 1/2012 | Snow et al. | |
| 8,142,365 B2 | 3/2012 | Miller | |
| 8,206,355 B2 | 6/2012 | Thorne | |
| 8,211,070 B2 | 7/2012 | Woehr et al. | |
| 8,246,584 B2 | 8/2012 | Aravena et al. | |
| 8,486,024 B2 | 7/2013 | Steube | |
| 8,506,568 B2 | 8/2013 | Miller | |
| 8,591,467 B2 | 11/2013 | Walker et al. | |
| 8,628,497 B2 | 1/2014 | Finnestad et al. | |
| 8,641,715 B2 | 2/2014 | Miller | |
| 8,656,929 B2 | 2/2014 | Miller et al. | |

(56) References Cited

U.S. PATENT DOCUMENTS

| | | |
|---|---|---|
| 8,668,698 B2 | 3/2014 | Miller et al. |
| 8,684,978 B2 | 4/2014 | Miller et al. |
| 8,715,287 B2 | 5/2014 | Miller |
| 8,844,112 B2 | 9/2014 | Snow et al. |
| 8,845,584 B2 | 9/2014 | Ferguson et al. |
| 8,864,714 B2 | 10/2014 | Harding et al. |
| 8,876,826 B2 | 11/2014 | Miller |
| 8,926,563 B2 | 1/2015 | Steube |
| 8,944,069 B2 | 2/2015 | Miller et al. |
| 8,974,410 B2 | 3/2015 | Miller et al. |
| 8,992,535 B2 | 3/2015 | Miller |
| 9,072,543 B2 | 7/2015 | Miller et al. |
| 9,220,483 B2 | 12/2015 | Frankhouser et al. |
| 9,295,487 B2 | 3/2016 | Miller et al. |
| 9,314,228 B2 | 4/2016 | Miller |
| 9,314,270 B2 | 4/2016 | Miller |
| 9,393,031 B2 | 7/2016 | Miller |
| 9,399,119 B2 | 7/2016 | Kuracina et al. |
| 9,408,632 B2 | 8/2016 | Erskine |
| 9,414,815 B2 | 8/2016 | Miller et al. |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,539,398 B2 | 1/2017 | Ferguson et al. |
| 9,545,243 B2 | 1/2017 | Miller et al. |
| 9,889,255 B2 | 2/2018 | Sonderegger et al. |
| 2001/0011164 A1 | 8/2001 | Bierman |
| 2002/0123724 A1 | 9/2002 | Douglas et al. |
| 2003/0225344 A1 | 12/2003 | Miller |
| 2003/0225411 A1 | 12/2003 | Miller |
| 2004/0059317 A1 | 3/2004 | Hermann |
| 2004/0220497 A1 | 11/2004 | Findlay et al. |
| 2005/0027263 A1 | 2/2005 | Woehr et al. |
| 2005/0033235 A1 | 2/2005 | Flint |
| 2005/0101933 A1 | 5/2005 | Marrs et al. |
| 2005/0107743 A1 | 5/2005 | Fangrow, Jr. |
| 2005/0165404 A1 | 7/2005 | Miller |
| 2005/0245878 A1 | 11/2005 | Mernoe et al. |
| 2006/0015066 A1 | 1/2006 | Turieo et al. |
| 2006/0025723 A1 | 2/2006 | Ballarini |
| 2006/0106402 A1 | 5/2006 | McLucas |
| 2007/0049945 A1 | 3/2007 | Miller |
| 2007/0270775 A1 | 11/2007 | Miller et al. |
| 2008/0140014 A1 | 6/2008 | Miller et al. |
| 2008/0215056 A1 | 9/2008 | Miller et al. |
| 2008/0221580 A1 | 9/2008 | Miller et al. |
| 2009/0054808 A1 | 2/2009 | Miller |
| 2009/0093830 A1 | 4/2009 | Miller |
| 2009/0118639 A1 | 5/2009 | Moos et al. |
| 2009/0204024 A1 | 8/2009 | Miller |
| 2009/0306697 A1 | 12/2009 | Fischvogt |
| 2010/0152616 A1 | 6/2010 | Beyhan et al. |
| 2010/0298784 A1 | 11/2010 | Miller |
| 2011/0028976 A1 | 2/2011 | Miller |
| 2011/0082387 A1 | 4/2011 | Miller et al. |
| 2013/0030370 A1 | 1/2013 | Walker et al. |
| 2013/0096561 A1 | 4/2013 | Miller et al. |
| 2014/0100528 A1 | 4/2014 | Finnestad et al. |
| 2014/0142577 A1 | 5/2014 | Miller |
| 2014/0276471 A1 | 9/2014 | Emery et al. |
| 2014/0277028 A1 | 9/2014 | Voic |
| 2014/0343454 A1 | 11/2014 | Miller et al. |
| 2015/0127006 A1 | 5/2015 | Miller |
| 2015/0230823 A1 | 8/2015 | Morgan et al. |
| 2015/0231364 A1 | 8/2015 | Blanchard et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0183974 A1 | 6/2016 | Miller |
| 2016/0184509 A1 | 6/2016 | Miller et al. |
| 2016/0206346 A1 | 7/2016 | Miller |
| 2017/0007271 A1 | 1/2017 | Miller et al. |
| 2017/0311981 A1 | 11/2017 | Real et al. |
| 2018/0125465 A1 | 5/2018 | Muse et al. |
| 2018/0256209 A1 | 9/2018 | Muse et al. |
| 2018/0256870 A1 | 9/2018 | Muse et al. |
| 2019/0282244 A1 | 9/2019 | Muse |

FOREIGN PATENT DOCUMENTS

| | | |
|---|---|---|
| EP | 0548612 A1 | 6/1993 |
| EP | 2849656 B1 | 5/2013 |
| EP | 2967508 B1 | 1/2016 |
| FR | 2481930 | 11/1981 |
| FR | 2522973 A2 | 9/1983 |
| FR | 2885512 A1 | 11/2006 |
| JP | 2000140125 A | 12/1998 |
| NL | 9401085 A | 6/1994 |
| WO | 200213893 A1 | 2/2002 |
| WO | 2008065646 A1 | 6/2008 |
| WO | 2013173360 A1 | 11/2013 |
| WO | 2014144239 A1 | 9/2014 |
| WO | 2018075694 A1 | 4/2018 |
| WO | 20180165334 A1 | 9/2018 |
| WO | 20180165339 A1 | 9/2018 |
| WO | 20190164990 A1 | 8/2019 |

OTHER PUBLICATIONS

Prometheus Medical Ltd., Prometheus PIN, Undated, Downloaded from https://www.prometheusmedical.co.uk/equipment/prometheus-equipment-intraosseous-access/prometheus-pin on Aug. 10, 2017, 2 pages.
United States Patent and Trademark Office, Office Action in U.S. Appl. No. 15/787,671, dated Feb. 27, 2020, 12 pages.
United States Patent and Trademark Office, Notice of Allowance in U.S. Appl. No. 15/787,671, dated Sep. 16, 2020, 18 pages.
United States Patent and Trademark Office, Notice of Allowance in U.S. Appl. No. 15/787,671, dated Dec. 31, 2020, 53 pages.
United States Patent and Trademark Office, Office Action in U.S. Appl. No. 15/914,964, dated Aug. 21, 2020, 19 pages.
United States Patent and Trademark Office, Office Action in U.S. Appl. No. 15/915,606, dated Sep. 23, 2020, 10 pages.
United States Patent and Trademark Office, Notice of Allowance in U.S. Appl. No. 15/915,606, dated Feb. 22, 2021, 49 pages.
U.S. Appl. No. 15/787,671, filed Oct. 18, 2017, Intraosseous Acces Devices, Systems, and Methods.
U.S. Appl. No. 15/914,964, filed Mar. 7, 2018, Safety Shields for Elongated Instruments and Related Systems and Methods.
U.S. Appl. No. 15/915,505, filed Mar. 8, 2018, Securement Devices, Systems, and Methods.

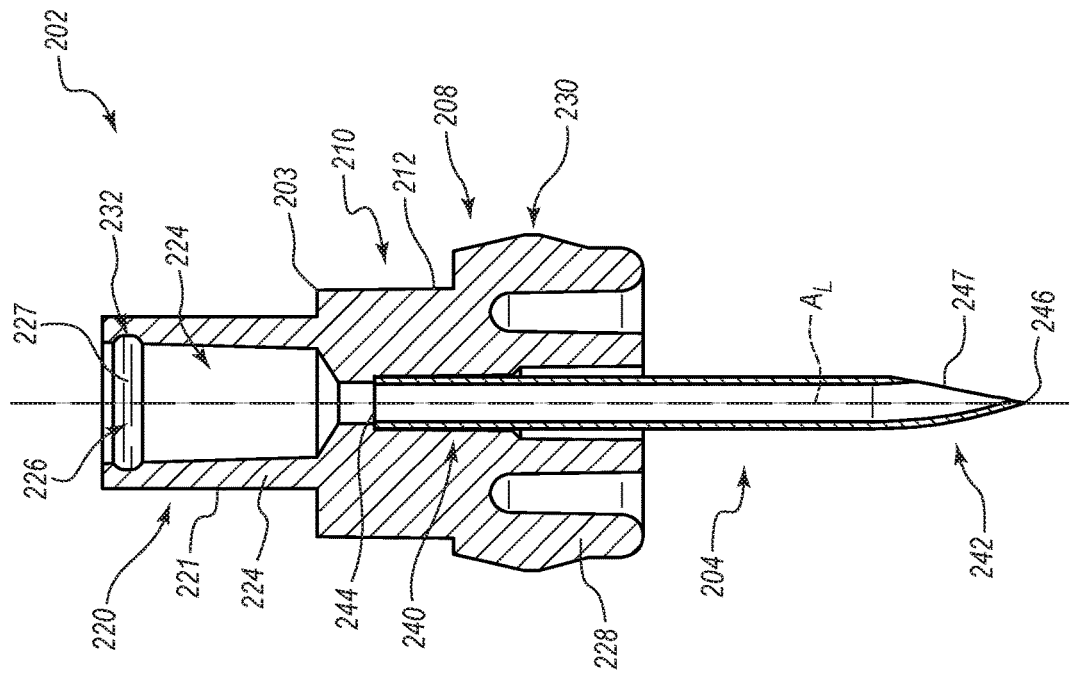
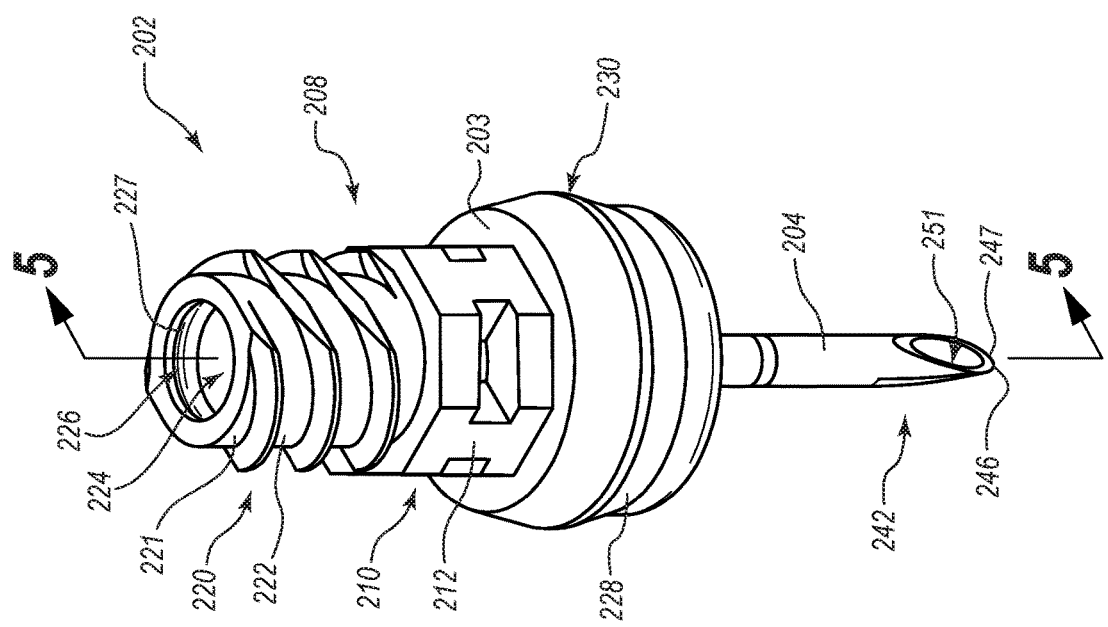

MEDICAL DRILLING DEVICES AND RELATED SYSTEMS AND METHODS

CROSS-REFERENCE TO RELATED APPLICATIONS

This application claims the benefit under 35 U.S.C. § 119(e) of U.S. Provisional Patent Application No. 62/632,554, titled DRILLING DEVICES AND RELATED METHODS, filed on Feb. 20, 2018, the entire contents of which are hereby incorporated by reference herein.

TECHNICAL FIELD

Certain embodiments described herein relate generally to drilling devices, and further embodiments relate more particularly to medical drilling devices, such as may be used, for example, for drilling into bone.

BACKGROUND

Medical drills are used for a variety of medical procedures, including, for example, orthopedic and dental procedures. Known devices, systems, and methods, however, suffer from one or more drawbacks and/or may not be suitable for providing access to an interior of a bone, such as for intraosseous vascular access. Moreover, many of such medical drills require electrical energy for operation, which may not be readily available in certain situations, such as in remote locales or after long periods of storage. These and/or other limitations of known medical drills and methods can be resolved, remedied, ameliorated, or avoided by certain embodiments described herein. Moreover, certain embodiments disclosed herein in the context of illustrative medical procedures can be used in other contexts, including contexts outside of the medical field.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 4 is a perspective view of an embodiment of a needle assembly portion of the access assembly of FIG. 1;

FIG. 5 is a cross-sectional view of the needle assembly taken along the view line 5-5 in FIG. 4;

DETAILED DESCRIPTION

The present disclosure relates generally to drilling devices, systems, and methods, and in particular, relates to medical drills and related methods. In some instances, drills are used to drill into or through bone, such as in orthopedic or dental procedures. Known systems for bone drilling can suffer from significant drawbacks, however.

Moreover, certain known drilling systems may not be suitable for providing access to an interior of a bone, such as for intraosseous vascular access applications. The present inventor has recognized the desirability, in at least some instances, of ensuring a user applies to a drill a forward or distally directed force (e.g., an insertion force) falling within a predetermined optimal range or otherwise exceeding a threshold value during a drilling event to achieve optimum drilling efficiency. Stated otherwise, in at least some instances, ensuring that a user applies the forward or distally directed force within the predetermined optimal range or otherwise in excess of the threshold value can yield a torque at a penetrator tip that is optimal for cutting through cortical bone. Certain embodiments described herein can advantageously ensure that drilling takes place within an optimized force and/or torque range and/or can achieve other and/or further advantages that are discussed herein or that will otherwise be apparent from the present disclosure.

Although certain embodiments are particularly well-suited for medical drilling to achieve intraosseous access, the present disclosure is not so limited. For example, some embodiments may be suitable for other medical applications, such as bone drilling for bone biopsy, orthopedic, or dental procedures. Still other or further embodiments may be suitable for non-medical applications.

Figure 1:
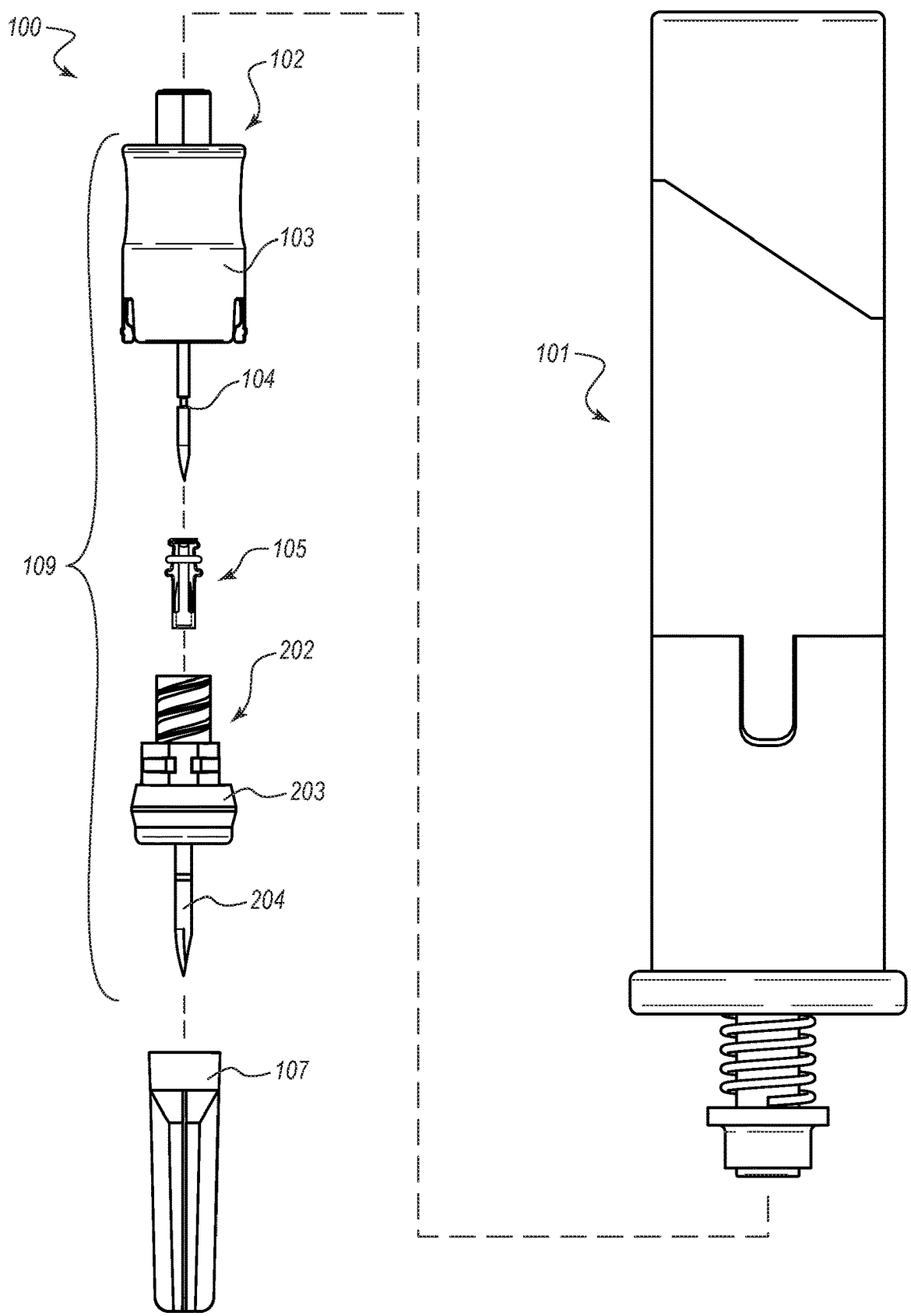
FIG. 1 is an exploded elevation view of an embodiment of an intraosseous access system that includes an access assembly and a driver that is configured to couple with the access assembly and drive a portion thereof into a bone of a patient.

FIG. 1 is an exploded elevation view of an embodiment of an intraosseous access system 100. The intraosseous access system 100 can be used to penetrate skin and underlying hard bone for intraosseous access, such as, for example to access the marrow of the bone and/or a vasculature of the patient via a pathway through an interior of the bone.

In various embodiments, the system includes a driver 101 and an access assembly 109. The driver 101 can be used to rotate the access assembly 109 into a bone of a patient. As further discussed hereafter, the driver 101 can be mechanically powered, such as via conversion of stored mechanical potential energy to kinetic energy. In further instances, the driver 101 can be automated. For example, the driver 101 may be pre-wound, preloaded, pre-charged, or otherwise placed in a state of stored mechanical energy, and the stored energy can be released automatically when certain predetermined conditions are met to drill the access assembly 109 into bone. The driver 101, when powered and/or automated, can achieve rotational speeds suitable for efficiently cutting through bone (e.g., cortical bone). In certain instances, the rotational speeds can far exceed speeds obtainable solely by manual manipulation of a drill (e.g., solely via manual rotation). In other or further embodiments, the driver 101 may be usable in a manual mode to partially or fully insert the access assembly 109 into bone manually. For example, the driver 101 may be configured for use as a powered and/or automated drill, but may optionally be used in a fully manual mode, as further discussed below.

The intraosseous access system 100, or more specifically the access assembly 109, can include an obturator assembly 102, a safety shield 105, and a needle assembly 202. Stated otherwise, the obturator assembly 102, the safety shield 105, and the needle assembly 202 may be referred to, collectively, as the access assembly 109. The access assembly 109 may also be referred to as an access system, a penetration system or assembly, an insertion system or assembly, etc.

The obturator assembly 102 is referred to as such herein for convenience, given that in the illustrated embodiment, the obturator assembly 102 includes an obturator 104. However, in various other embodiments, the obturator 104 may be replaced with a different elongated medical instrument. As used herein, the term "elongated medical instrument" is a broad term used in its ordinary sense that includes, for example, devices such as needles, cannulas, trocars, obturators, stylets, etc. Accordingly, the obturator assembly 102 may be referred to more generally as an elongated medical instrument assembly, as any suitable elongated medical instrument is contemplated for use in conjunction with or in place of the obturator 104. In like manner, the obturator 104 may be referred to more generally as an elongated medical instrument.

In the illustrated embodiment, the obturator assembly 102 includes a coupling hub 103 that is attached to the obturator 104 in any suitable manner (e.g., one or more adhesives or overmolding). The coupling hub 103 can be configured to interface with the driver 101, as further discussed below. The coupling hub 103 may alternatively be referred to as an obturator hub 103 or, more generally, as an elongated instrument hub 103.

In the illustrated embodiment, the shield 105 is configured to couple with the obturator 104. The manner of coupling can permit relative longitudinal movement between the obturator 104 and the shield 105, such as sliding, translating, or other movement along an axis of elongation (i.e., axial movement), when the shield 105 is in a first operational mode, and can prevent the same variety of movement when the shield 105 is transitioned to a second operational mode. For example, the shield 105 may couple with the obturator 104 in a manner that permits longitudinal translation when the obturator 104 maintains the shield 105 in an unlocked state, and when the obturator 104 is moved to a position where it no longer maintains the shield 105 in the unlocked state, the shield 105 may automatically transition to a locked state in which little or no translational movement is permitted between the shield 105 and the obturator 104. Stated otherwise, the shield 105 may be longitudinally locked to a fixed or substantially fixed longitudinal orientation relative to the obturator 104 at which the shield 105 inhibits or prevents inadvertent contact with a distal tip of the obturator.

With continued reference to FIG. 1, the needle assembly 202 is referred to as such herein for convenience. In the illustrated embodiment, the needle assembly 202 includes a needle 204. However, in various other embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In the illustrated embodiment, the needle 204 is a cutting element or cutting cannula, which includes one or more cutting faces for cutting through bone, as discussed further below. The obturator 104 is not a cutting instrument and instead inhibits entry of material into a lumen defined by the needle 204. In other embodiments, the obturator 104 may be replaced with a cutting instrument, such as a trocar. Any suitable cutting arrangement for the access assembly 109 is contemplated.

In the illustrated embodiment, the needle assembly 202 includes a needle hub 203 that is attached to the needle 204 in any suitable manner. The needle hub 203 can be configured to couple with the obturator hub 103 and may thereby be coupled with the driver 101, as further discussed below. The needle hub 203 may alternatively be referred to as a cannula hub 203.

In the illustrated embodiment, the shield 105 is configured to couple with the needle hub 203. The coupling can prevent relative axial or longitudinal movement between the needle hub 203 and the shield 105, such as sliding, translating, or the like, when the shield 105 is in the first operational mode, and can permit the shield 105 to decouple from the needle hub 203 when the shield 105 is transitioned to the second operational mode. For example, the shield 105 may couple with the needle hub 203 so as to be maintained at a substantially fixed longitudinal position relative thereto when the obturator 104 maintains the shield 105 in the unlocked state, and when the obturator 104 is moved to a position where it no longer maintains the shield in the unlocked state, the shield 105 may automatically transition to a locked state relative to the obturator 104, in which state the shield 105 also decouples from the needle hub 203.

Figure 24:
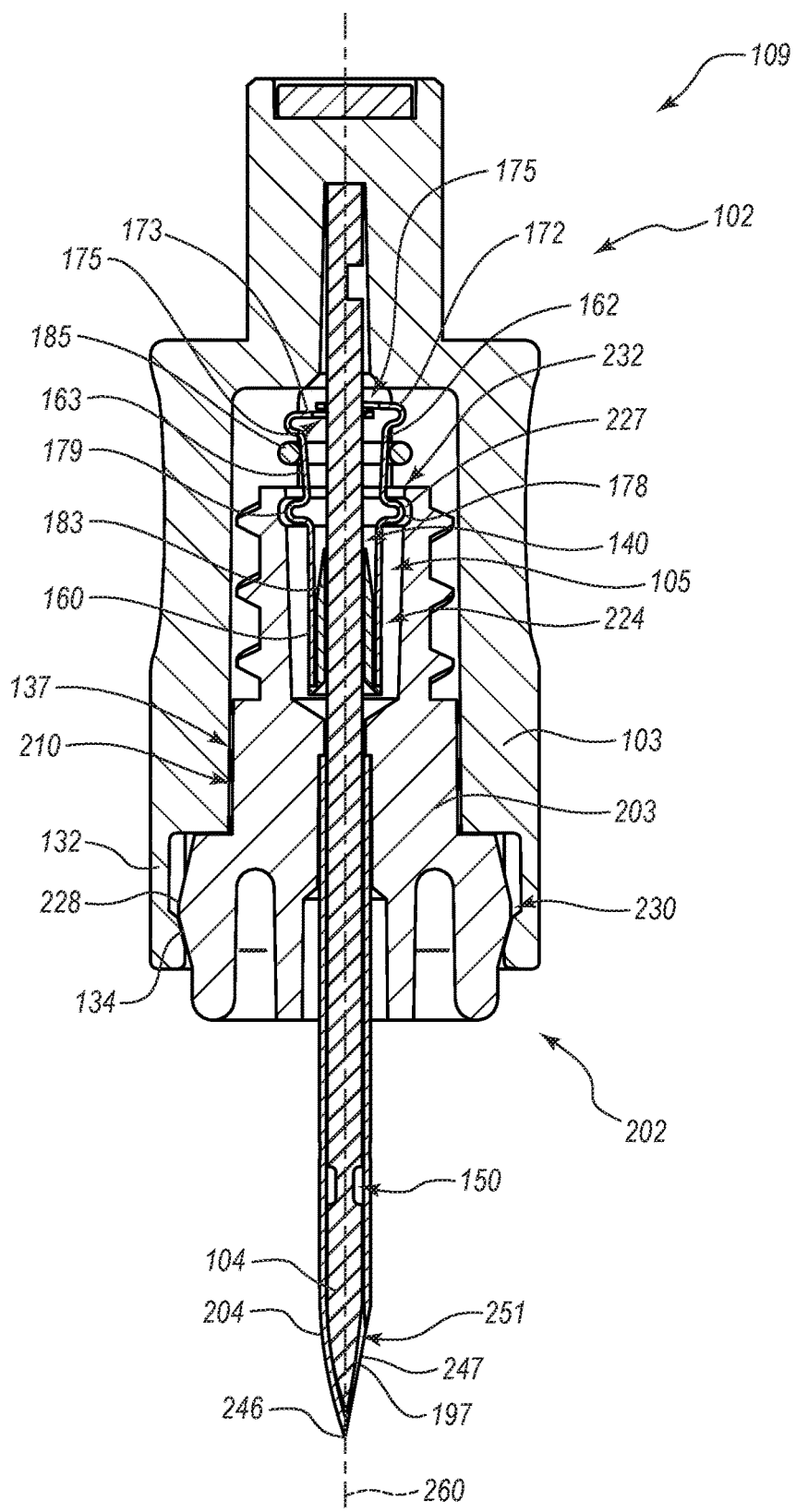
FIG. 24 is a cross-sectional view of the access assembly in an assembled state.

The shield 105 can be coupled with the obturator 104, the obturator 104 can be inserted into the needle 204, and the obturator hub 103 can be coupled to the needle hub 203 to assemble the access assembly 109 (see FIG. 24). In the illustrated embodiment, a cap 107 may be provided to cover at least a distal portion of the needle 204 and the obturator 104 prior to use of the access assembly 109. For example, as further discussed below, in the illustrated embodiment, a proximal end of the cap 107 can be coupled to the obturator hub 103.

Figure 3:
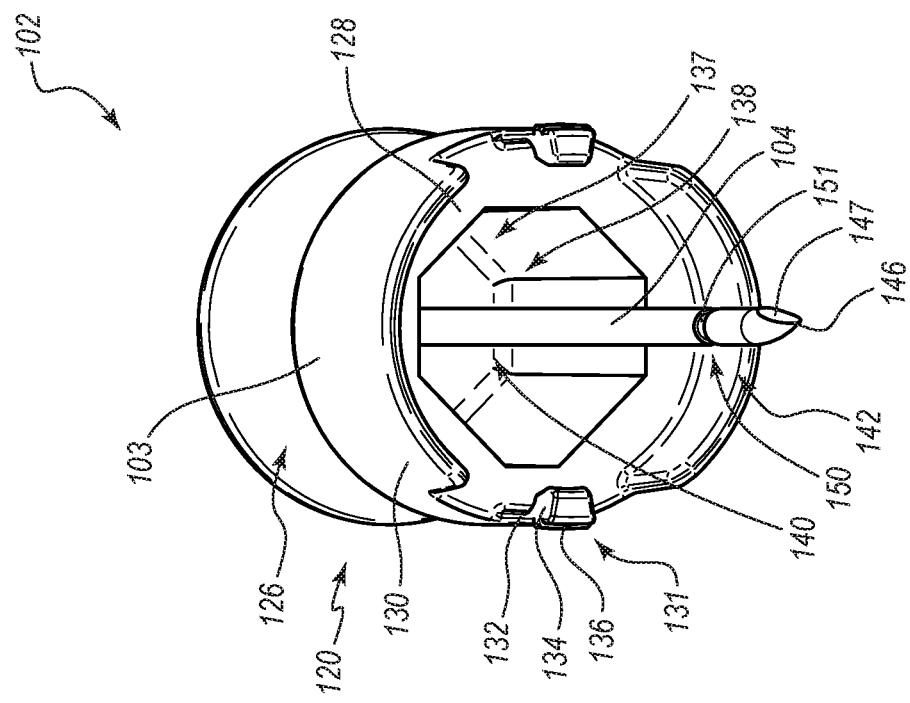
FIG. 3 is a further perspective view of the obturator assembly.
Figure 2:
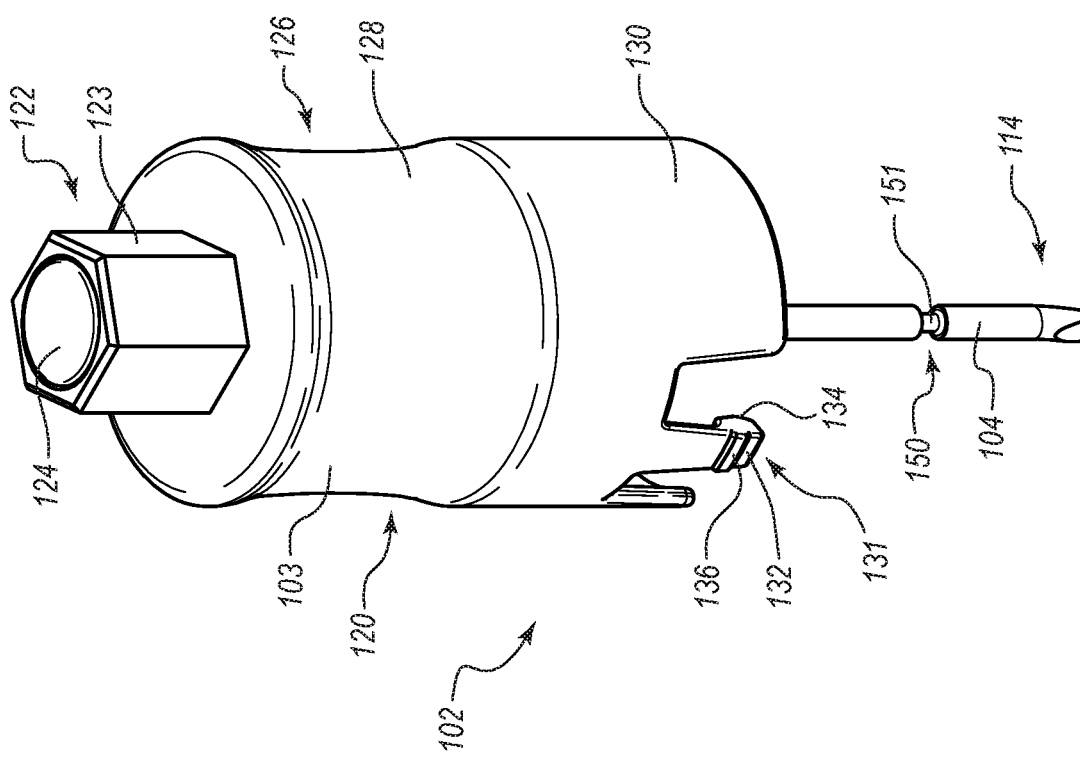
FIG. 2 is a perspective view of an embodiment of an obturator assembly portion of the access assembly of FIG. 1.

With reference to FIGS. 2, 3, and 24, the obturator assembly 102, which includes the obturator hub 103 and the obturator 104, is shown in greater detail. In the illustrated embodiment, the obturator hub 103 includes a body or housing 120. A proximal end of the housing 120 can be coupled with (e.g., may be attached to or may itself define) a coupling interface 122 for coupling with a corresponding coupling interface of the driver 101, as discussed further below with respect to FIGS. 6 and 7. In the illustrated embodiment, the coupling interface 122 is formed as a shaft 123 that is configured to be received within a cavity of a socket 329 defined by a drive shaft 320 of the automated driver 101 (see FIGS. 6 and 7). In particular, the shaft 123 can interface with the socket 329 so as to be rotated thereby. In the illustrated embodiment, the shaft 123 defines a hexagonal cross-section that complements a hexagonal cross-section of the socket 329. Any other suitable arrangement is contemplated. In further embodiments, the socket 329, and the shaft 123 may be reversed, in that the driver 101 may include a shaft and the obturator hub 103 may define a socket for receiving the shaft of the driver 101.

The coupling interface 122 of the obturator hub 103 may further include a magnetic member 124, which may facilitate coupling with and/or may strengthen a coupling between the coupling interfaces 122, 328 of the obturator hub 103 and the driver 101, respectively. In various embodiments, the magnetic member 124 may include, for example, one or more of a ferromagnetic material and a ferromagnet. In some embodiments, the socket 329 may include a similar magnetic member (e.g., that comprises a ferromagnetic material and/or a ferromagnet) that magnetically couples with the magnetic member 124. For example, in some embodiments, the magnetic member 124 may comprise a magnet and the socket 329 may include a complementary magnetic member 327 (see FIG. 25A) at the base of the socket 329. In other embodiments, the socket 329 itself may be formed as the magnetic member. For example, in some embodiments, the magnetic member 124 may comprise a magnet and the socket 329 may be formed of a magnetic material to which the magnetic member 124 is attracted. In still other embodiments, the magnetic member 124 may be omitted.

With continued reference to FIGS. 2, 3, and 24, the body or housing 120 may further define a grip 126 that may facilitate manipulation of the obturator hub 103. For example, in the illustrated embodiment, the grip 126 is formed as an indented region of a sidewall 128 that spans a full perimeter of the housing 120.

The illustrated obturator hub 103 includes a skirt 130 that extends distally from a central portion of the housing 120. In the illustrated embodiment, the skirt 130 is defined by a distal portion of the sidewall 128. The skirt 130 can include one or more mechanical coupling members 131 that are configured to selectively couple the obturator hub 103 to the needle hub 203. In the illustrated embodiment, the skirt 130 includes two such mechanical coupling members 131 at opposite sides thereof. In particular, the illustrated embodiment includes two resilient arms or projections 132 that are capable of resiliently deforming in a lateral or radial direction. Each arm can include a snap interface, inward protrusion, or catch 134 at an internal side thereof that can interface with the needle hub 203 to achieve the coupling configuration.

In the illustrated embodiment, the obturator hub 103 further includes a pair of outward protrusions 136 that can assist in coupling the cap 107 to the obturator hub 103. For example, in some embodiments, the cap 107 can define an inner diameter only slightly larger than an outer diameter of the skirt 130. The outward protrusions 136 can slightly deform a proximal end of the cap 107 from a substantially cylindrical shape to a more oblong shape, which may enhance a grip of the cap 107 against the skirt 130. Any other suitable connection arrangement for the cap 107 is contemplated.

With reference to FIGS. 3 and 24, the sidewall 128 can further define a coupling interface 137 configured to couple the obturator hub 103 to the needle hub 203 in a manner that causes the obturator hub 103 to rotate in unison with the needle hub 203. In the illustrated embodiment, the coupling interface 137 is formed as a socket 138 into which a shaft portion of the needle hub 203 can be received. The socket 138 can define a keyed shape that permits the obturator hub 103 to be coupled to the needle hub 203 in only one unique rotational or angular orientation. In particular, in the illustrated embodiment, the socket 138 defines an elongated right octagonal prism of which five contiguous sides are substantially identically sized, two enlarged sides that extend from the ends of the five contiguous sides are lengthened relative to the five contiguous sides, and an eighth shortened side that extends between the two enlarged sides is shorter than the five contiguous sides. Any other suitable keying configuration is contemplated. As further discussed below, a keyed interface such as just described can ensure that the obturator 104 and the needle 204 are coupled to each other in a manner that may be desired, in some embodiments, such as to ensure that distal faces of both components are substantially parallel to each other and/or to otherwise ensure that a distal face of the obturator 104 is positioned in a desired manner relative to a distal face of the needle 204. For example, in some embodiments, the keyed interface ensures that the distal faces of the obturator 104 and the needle 204 are substantially parallel to each other and/or ensures that the distal face of the obturator 104 is fully recessed relative to the distal face of the needle 204.

With continued reference to FIG. 3, in some embodiments, the obturator 104 extends between a proximal end 140 that is coupled to the obturator hub 103 and a distal end 142. The distal end 142 of the obturator 104 has a distal tip 146 at an extremity thereof. In the illustrated embodiment, the housing 120 of the obturator hub 103 substantially encompasses the proximal end 140 of the obturator 104.

The distal end 142 of the obturator 104 includes a distal face 147, which may, in various embodiments, alternatively be referred to as a cut face, ground face, or angled face. In some embodiments, the distal face 147 is formed as a bevel that is at an angle relative to a central longitudinal axis of the obturator 104. For example, in the illustrated embodiment, the distal face 147 defines a substantially planar bevel. In some embodiments, the distal face 147 of the obturator 104 may be configured to be recessed relative to a distal face of the needle 204

The beveled distal face 147 can be formed in any suitable manner, such as by grinding. For example, the distal face 147 that is substantially planar may be formed by a bias grind (which may also be referred to as a simple bias grind). As further discussed below, in some embodiments, the ground distal face 147 is formed (e.g., ground) at a distal end of a substantially cylindrical rod, and the rod is bent after the distal face 147 has been formed. In other embodiments, the cylindrical rod is bent before the distal face 147 is formed.

In still other embodiments, a cylindrical rod is not bent, but rather, each of the distal face 147 and a curved or rounded region 148 adjacent thereto is instead formed by grinding. Other suitable processes for forming the distal end 142 of the obturator 104 are contemplated.

In some embodiments, the obturator 104 may be solid. For example, the obturator 104 may be devoid of passageways or openings extending through any portion thereof. Similarly, the distal end 142 of the obturator 104 may be substantially solid or closed, and may be devoid or openings or passageways therein or therethrough. The distal end 142 of the obturator 104 may substantially fill a lumen of the needle 204, or at least a distal portion of the lumen, to prevent skin or bone from entering into the needle 204 during an insertion event.

The obturator 104 may be formed of any suitable material, such as a substantially rigid material that can resist bending. The material can be sufficiently rigid and strong to inhibit tissue and/or bone from entering a lumen of the needle 204 during an access event. In various embodiments, the obturator 104 can comprise one or more of a rigid plastic or stainless steel. The obturator 104 may, in some instances, provide internal or structural support to the needle 204 during an insertion event. For example, the obturator 104 may act as a stiffener or stylet to inhibit bending of the needle 204 during drilling.

The distal end 142 of the obturator 104 may be shaped and sized to substantially fill a distal end of the needle 204, as shown in FIG. 24. In various embodiments, such an arrangement can inhibit bending or flattening of the distal end of the needle 204. For example, in some embodiments, there may be a close fit between an inner wall of the distal tip of the needle 204 and an outer surface of the distal end 142 of the obturator 104, and contact between these surfaces can permit the obturator 104 to reinforce the needle 204. For example, in the illustrated embodiment, the distal end 142 of the obturator 104 includes the curved region 148, which may also be referred to as a rounded, bent, or curved region or as a curved surface. A contour of the curved surface 148 can closely match a contour of an inner wall of the needle 204 at the distal end thereof. For example, in various embodiments, these curved surfaces may contact one another along a portion or substantially an entirety of length of the curved surface 148 of the obturator 104 and/or a portion or substantially an entire length of the inner curved surface of the distal end of the needle 204.

In other instances, a small space or gap may be present between the distal end 142 of the obturator 104 and the inner surface of the distal end of the needle 204. In certain of such arrangements, the distal end 142 of the obturator 104 may not initially provide resistance against bending of the needle tip. However, the obturator 104 may instead prevent the needle tip from bending beyond a preset amount. For example, upon bending of the needle tip such that the inner wall comes into contact with the distal end 142 of the obturator 104, the obturator 104 can stop or inhibit further bending of the needle tip.

In the illustrated embodiment, the obturator 104 may further include a recess 150. The recess 150 may be at a position that is between the proximal end and the distal end 142 of the obturator. Stated otherwise, the recess 150 may be positioned proximally relative to the distal tip 146 of the obturator 104. The recess 150 may be of any suitable variety, such as a groove, track, or any other suitable region of indentation or of reduced diameter or reduced thickness, as compared with, for example, a portion of the obturator 104 that is proximal to the recess 150. The recess 150 may or may not extend fully about a longitudinal axis of the obturator 104. In the illustrated embodiment, the recess 150 is defined as a groove 151 that extends fully about the longitudinal axis of the obturator.

With reference to FIGS. 4, 5, and 24, as previously discussed, the needle assembly 202 can include the needle hub 203 and the needle 204, which can be fixedly secured to each other in any suitable manner (e.g., one or more adhesives or overmolding). Further, as previously discussed, the needle hub 203 and the needle 204 may more generally be referred to as a cannula hub and as a cannula, respectively.

In the illustrated embodiment, the needle hub 203 includes a housing or body 208. The body 208 can define a coupling interface 210 that is configured to couple with the coupling interface 137 of the obturator hub 102 (see FIG. 3). For example, the coupling interface 210 can be formed as a shaft 212 that is configured to be received within the socket 138 of the obturator hub 102 (see FIGS. 3 and 24). As shown in FIG. 4, in some embodiments, the shaft 212 can define a keyed shape that permits the needle hub 203 to be coupled to the obturator hub 103 in only one unique rotational or angular orientation. In particular, in the illustrated embodiment, the shaft 212 defines an elongated right octagonal prism of which five contiguous sides are substantially identically sized, two enlarged sides that extend from the ends of the five contiguous sides are lengthened relative to the five contiguous sides, and an eighth shortened side that extends between the two enlarged sides is shorter than the five contiguous sides. The prism shape may be substantially the same as that defined by the coupling interface 137, but with slightly shorter sides. Any other suitable keying configuration is contemplated.

The needle hub 202 can further include a connector 220, e.g., a medical connector, of any suitable variety. The connector 220 may be defined by the housing 208 and may extend proximally from the shaft 212. The connector 220 can be configured to couple with any suitable medical equipment, such as for infusing fluid into and/or aspirating fluid from a patient, after the needle 204 has been inserted into bone. For example, in the illustrated embodiment, the connector 220 is formed as a Luer fitting 221 (i.e., a female Luer fitting). The illustrated Luer fitting 221 includes a sidewall 222 that defines a cavity or lumen 224. In some embodiments, a portion of a male Luer fitting may be received within the lumen 224 when the needle hub 202 is in use. The lumen 224 of the connector 220 can be in fluid communication with a lumen 251 of the needle 204.

In the illustrated embodiment, the sidewall 222 defines a connection interface 226 that is configured to couple the needle hub 202 with the shield 105 when the shield 105 is in the unlocked state relative to the obturator 104. In this state, the shield 105 may also be termed to be in a locked or engaged state relative to the needle hub 202. For example, in the illustrated embodiment, the connection interface 226 is formed as an annular groove 227 within which the outward protrusions of the shield 105 can be received to prevent the shield 105 from moving in at least a longitudinal direction relative to the needle hub 202.

The housing 208 may further define a skirt 228, which may extend distally from the shaft 212. The skirt 228 may also extend outwardly relative to the shaft 212. The skirt 228 may define a maximum transverse perimeter 230 of the hub 202. In the illustrated embodiment, the maximum transverse perimeter 230 is substantially circular. The maximum transverse perimeter 230 represents an outline of the needle assembly 202 when the assembly 202 is viewed from above or below, or stated otherwise, is viewed along a longitudinal axis of the needle assembly 202.

With reference to FIG. 5, an upper interior region of the sidewall 222 can define a maximum transverse perimeter 232 of the lumen 224. In the illustrated embodiment, the maximum transverse perimeter 232 is substantially circular. In other embodiments, the maximum transverse perimeter 232 may be defined by a portion of the sidewall 222 that is positioned further down, within the lumen 224, and may not, for example, be visible in a top plan view of the needle hub 203. In still other embodiments, the maximum transverse perimeter 232 represents an outline of the lumen 224 when the assembly 202 is viewed from above, or stated otherwise, is viewed along a longitudinal axis of the needle assembly 202.

With continued reference to FIG. 5, the needle 204 can include a proximal end 240 and a distal end 242. The proximal end 240 terminates at a proximal tip 244, and the distal end 242 terminates at a distal tip 246. The distal tip 246 may also be referred to as the distalmost point of the needle 204. The proximal end 240 can be fixedly secured to the housing 208 in any suitable manner. The needle 204 may be formed of any suitable material. For example, in some embodiments, the needle 204 is formed of stainless steel, such as 304 stainless steel, 316 stainless steel, or any other suitable grade of stainless steel (e.g., such as may be used for hypodermic needles). The material may desirably be sufficiently rigid to pierce a tissue layer and penetrate hard bone.

With reference to FIG. 5, the distal end 242 of the needle 204 can include a distal face 247, which may, in various embodiments, alternatively be referred to as a cut face, ground face, or angled face. In some embodiments, the distal face 247 is formed as a bevel that is at an angle relative to a central longitudinal axis $A_L$ of the needle 204, which can correspond to an axis of rotation of the needle 204 during an insertion event. For example, in the illustrated embodiment, the distal face 247 defines a substantially planar bevel. The beveled distal face 247 can be formed in any suitable manner, such as by grinding. For example, the distal face 247 that is substantially planar may be formed by a bias grind (which may also be referred to as a simple bias grind). In some embodiments, the ground distal face 247 is formed (e.g., ground) at a distal end of a substantially cylindrical tube, and the tube is bent after the distal face 247 has been formed. In other embodiments, the cylindrical tube is bent before the distal face 247 is formed. In some embodiments, the distal face 247 is substantially symmetrical relative to a vertical plane through the longitudinal axis $A_L$. The distal face 247 may be substantially equally efficient at cutting through bone regardless of the direction (clockwise, counterclockwise) the needle 204 is rotated about the longitudinal axis $A_L$.

Figure 6:
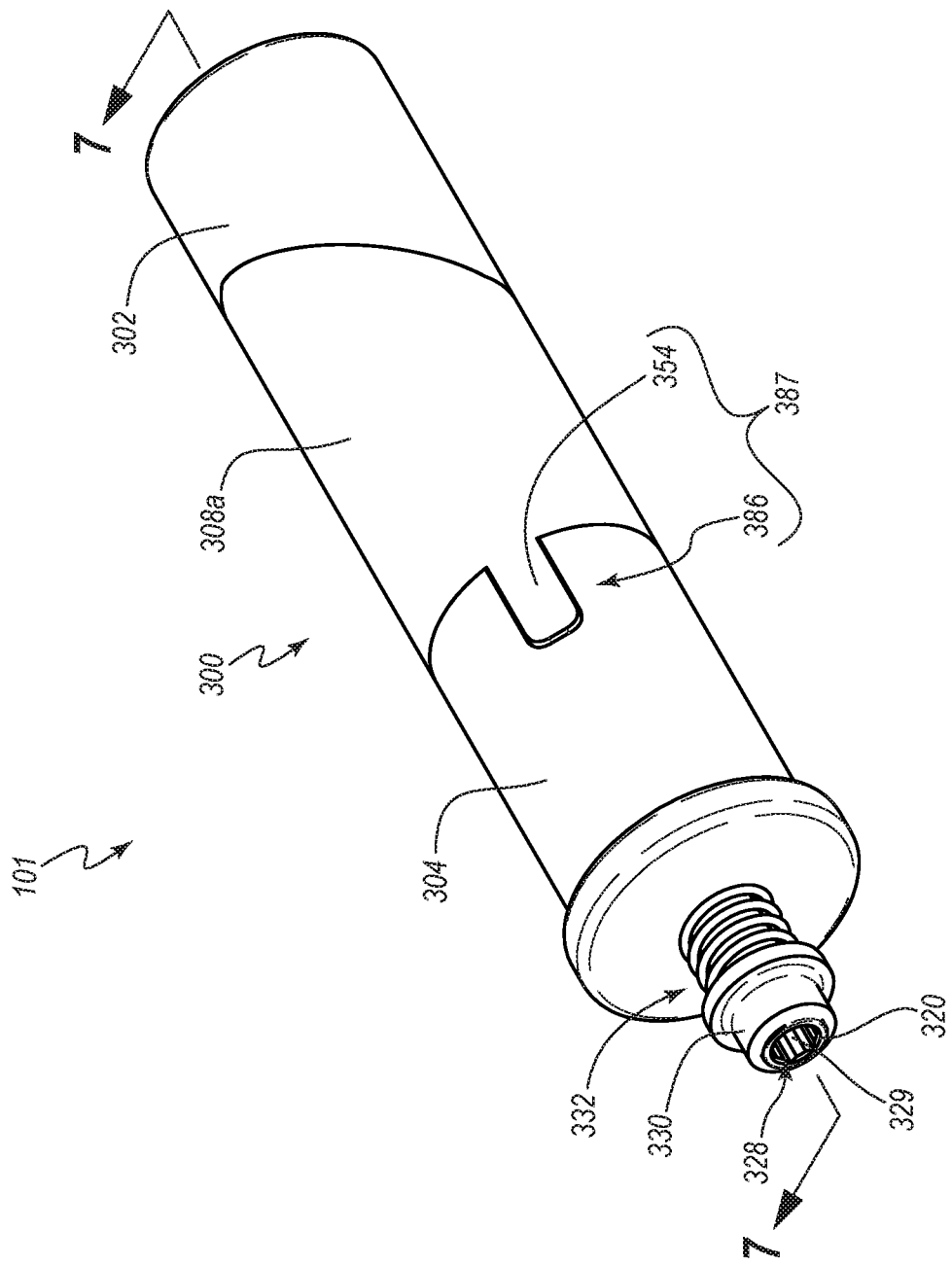
FIG. 6 is a perspective view of the driver of FIG. 1.
Figure 7:
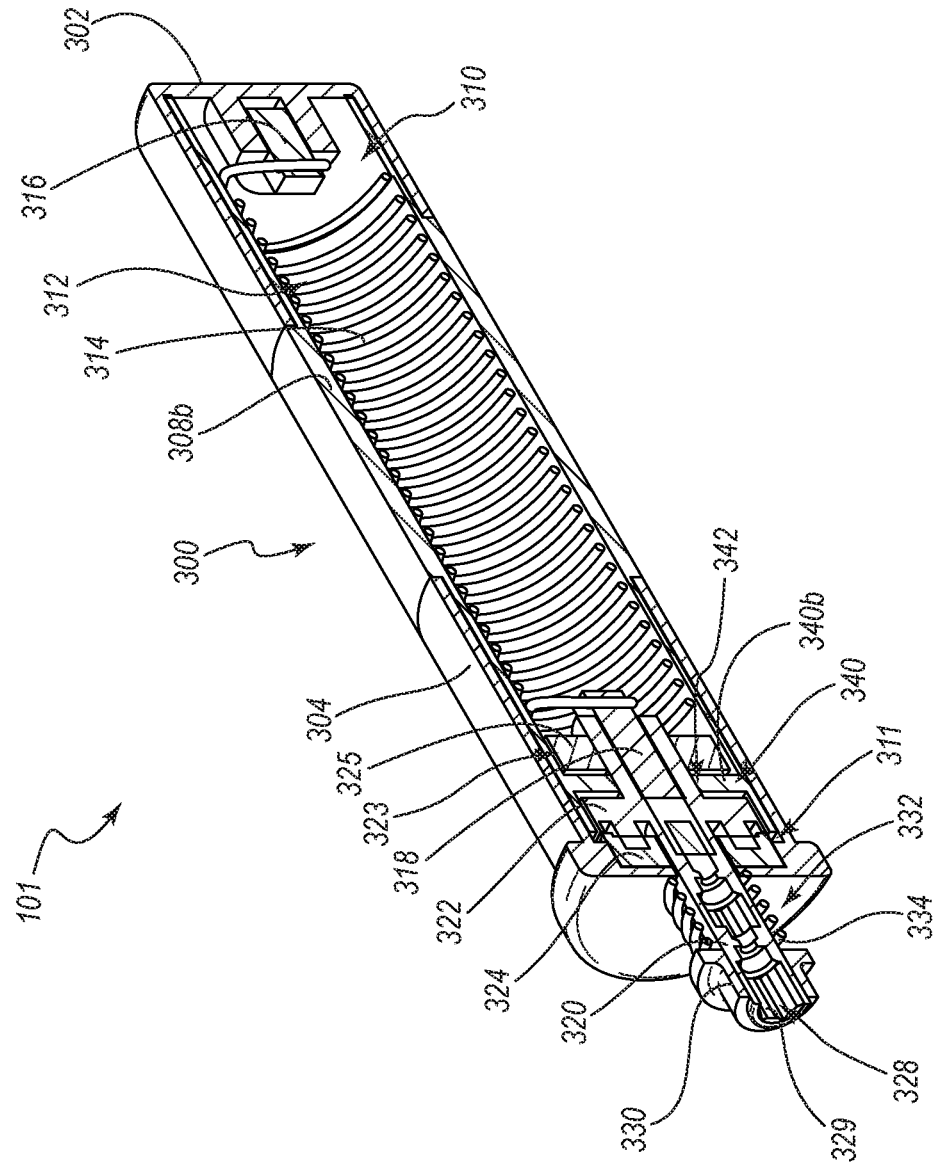
FIG. 7 is a perspective cross-sectional view of the driver taken along the view line 7-7 in FIG. 6.

FIGS. 6 and 7 depict an embodiment of a driver 101 that is compatible with the system 100. The driver 101 can be particularly well suited for introducing the access assembly 109 into a bone of a patient. The driver 101 may also be referred to as a drill.

The illustrated embodiment of the driver 101 includes a housing 300, a proximal cap 302, and a distal cap 304. For reasons that will be apparent hereafter, the housing 300 may also or alternatively be referred to as a body, a shaft, a stem, an intermediate structure, a hub, a base, a translational/rotational base, a core, etc.; the proximal cap 302 may also or alternatively be referred to as a winding cap, a tensioning cap, a rotational cap, a rotational element, etc.; and the distal cap 304 may also or alternatively be referred to as a sliding cap, a regulating (e.g., force-regulating) cap, a translational cap, an advancement element, etc. Further, the proximal cap 302 may also or alternatively be referred to as a dial, grasp, or grip 302 and/or the distal cap 304 may also or alternatively be referred to as a handle 304. For these and other components disclosed herein, other appellations than those explicitly recited herein are also possible based on their functionalities, structures, or the like.

The housing 300 can encompass or enclose a substantial amount of one or more internal components of the driver 101. The housing 300 may be formed of multiple components. In the illustrated embodiment, the housing 300 comprises two segments: a housing component 308a and a housing component 308b. In the illustrated embodiment, as further discussed below, the housing components 308a, 308b are identical to each other. Each may be referred to as a housing half. In some instances, utilizing multiple identical components to form the housing can facilitate and/or reduce the cost of manufacture for the driver 101.

The housing components 308a, 308b can cooperate to define a proximal cavity 310 (FIG. 7), which may also be referred to as a torsion cavity, a drive cavity, or energy storage cavity. The proximal cavity 310 can be sized to receive a mechanical energy-storage device 312 therein. The mechanical energy-storage device 312, as its name implies, can comprise any suitable mechanical device capable of storing energy. For example, in some embodiments, the mechanical energy-storage device 312 can be displaceable, deformable, or otherwise alterable to transition from a natural or resting state to a loaded or energy-storage state in which the device 312 stores potential energy that can subsequently be converted to mechanical kinetic energy. The mechanical energy-storage device 312 may also be referred to as a rotational biasing member. For example, when in a loaded state, the device 312, or rotational biasing member, can provide a rotational bias to the drive shaft 320.

In the illustrated embodiment, the mechanical energy-storage device 312 comprises a torsion spring 314. The torsion spring 314 can be coupled to the proximal cap 302. In the illustrated embodiment, a proximal end of the torsion spring 314 is coupled with the proximal cap 302 via a proximal coupling block 316, which may also be referred to as a coupling member. The torsion spring 314 can define a longitudinal cavity extending therethrough.

The torsion spring 314 can also be coupled to a drive shaft 320, which is discussed in greater detail hereafter. In the illustrated embodiment, a distal end of the torsion spring 314 is coupled to the drive shaft 320 via a distal coupling block 318, which may also be referred to as a coupling member. The drive shaft 320 may be positioned entirely at an exterior of the longitudinal cavity of the torsion spring 314, or may extend through at least a portion of the longitudinal cavity. In the illustrated embodiment, the drive shaft 320 extends through only a small portion of the longitudinal cavity of the torsion spring 314.

With continued reference to FIGS. 6 and 7, the drive shaft 320 extends through the handle 304, which is coupled to a distal end of the housing 300. In particular, the handle 304 covers or encompasses the distal end of the housing 300. The handle 304 can cooperate with the distal end of the housing 300 to define a distal cavity 311. The distal cavity 311 may also be referred to as a rotation control cavity.

With reference to FIG. 7, the drive shaft 320 can include a selectively engageable stopping mechanism, such as a clutch 322. The selectively engageable stopping mechanism can be configured to engage a stop 324, such as a clutch receiver, that is associated with or otherwise coupled to the handle 304. In the illustrated embodiment, the stop 324 comprises a clutch receiver that is complementary to and engageable with the clutch 322, which is defined by, or otherwise coupled to, the drive shaft 320.

The drive shaft 320 can also be coupled to a positioning element or bearing 323, such as a washer 325, which is positioned within the proximal cavity 310. In the illustrated embodiment, the washer 325 is fixedly secured (e.g., permanently adhered) to the drive shaft 320. In the illustrated embodiment the washer 325 is situated at a proximal side of a platform or partition 340 defined by the housing 300. Stated otherwise, the partition 340 is positioned between (e.g., sandwiched between) an upper surface of the clutch 322 and a lower surface of the washer 325. In some embodiments, one or more friction-reducing elements may be positioned between the clutch 322 and the partition 340 and/or between the partition 340 and the washer 325. For example, any suitable friction-reducing layer or coating (e.g., Teflon film or coating), bearing, or other friction-reducing component is contemplated, which can reduce friction between the partition 340 and the components positioned at either side thereof during rotation of the drive shaft 320.

With reference again to FIGS. 6 and 7, the drive shaft 320 can define a coupling interface 328, e.g., at a distal end thereof. The coupling interface 328 can be configured to selectively couple with the coupling interface 122 of the obturator hub 103 (FIG. 2). In the illustrated embodiment, the coupling interface 328 comprises a socket 329 that is complementary to and configured to engage with the coupling interface 122 of the obturator hub 103. In particular, the socket 329 is shaped the same as and just slightly larger than (so as to achieve, e.g., a close, snug, or tight fit with) the shaft 123, as previously described.

A laterally projecting collar 330 can be fixedly secured to the drive shaft 320 in any suitable manner. The collar 330 can function as a stop that can contact a distal end of a biasing member 332. The biasing member 332 can also or alternatively be referred to as a longitudinal biasing member, a separation biasing member, a regulating member, a force-control member, a drilling-optimization member, etc. In the illustrated embodiment, the biasing member 332 comprises a compression spring 334. The compression spring 334 can extend between the collar 330 and the handle 304. In the illustrated embodiment, a distal end of the compression spring 334 presses against a proximal face of the collar 330 and a proximal end of the compression spring 334 presses against a distal, external surface of the handle 304.

As further discussed below, the compression spring 334 can be configured to ensure that the driver 101 achieves efficient drilling through bone. For example, the compression spring 334 can set, determine, or regulate a force at which drilling is automatically permitted to commence. In other or further instances, the compression spring 334 can ensure that, after having commenced, the drilling continues only within a set range of distally directed forces. The compression spring 334 can oppose proximally directed forces on the drive shaft 320, such as may be applied to the drive shaft when an accesses assembly 109 that is coupled to the drive shaft 320 is pressed against a bone.

Figure 8:
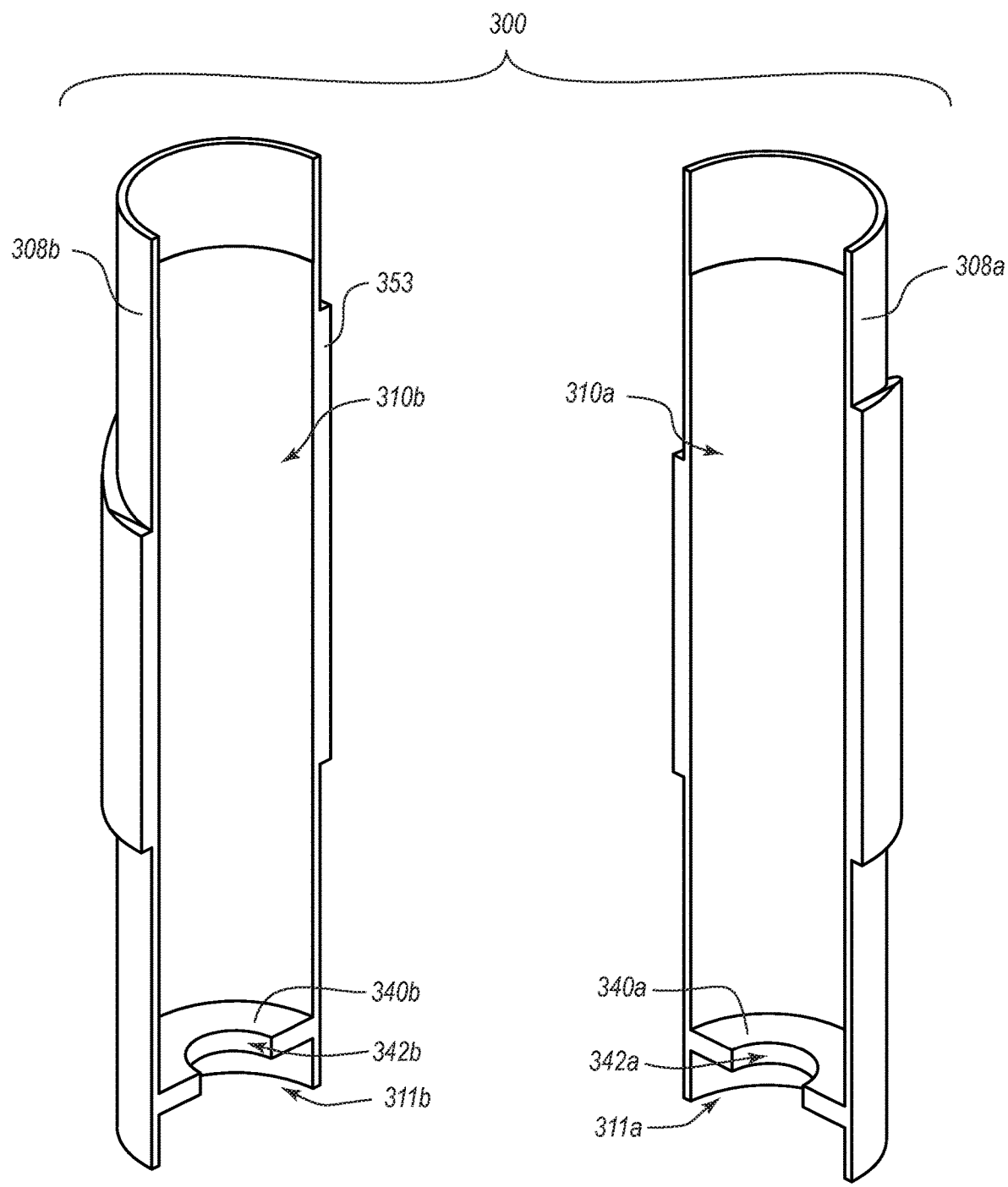
FIG. 8 is an exploded perspective view of an embodiment of a housing portion of the driver, which includes two separate housing components.

With reference to FIG. 8, as previously discussed, the housing 300 can include two housing components 308a, 308b. The housing components can be identical to each other. Each can define a separate cavity 310a, 310b, such that when the housing components 308a, 308b are brought together, they define at least a portion of the proximal cavity 310 previously described. Similarly, each of the housing components 308a, 308b can define a separate cavity 311a, 311b, such that when the housing components 308a, 308b are brought together, they define at least a portion of the distal cavity 311 previously described.

Each housing component 308a, 308b defines a portion of the partition 340. in particular, the housing component 308a defines a partition segment 340a, and the housing component 308b defines a partition segment 340b. In the illustrated embodiment, each partition segment 340a, 340b is substantially semi-circular, and each defines a recess 342a, 342b. When the housing components 308a, 308b are brought together, the resulting partition 340 (i.e., the combination of the partition segments 340a, 340b) substantially defines an annulus having an opening 342 (i.e., the combination of the recesses 342a, 342b) through which the drive shaft 320 can extend, as shown in FIG. 7.

Figure 10:
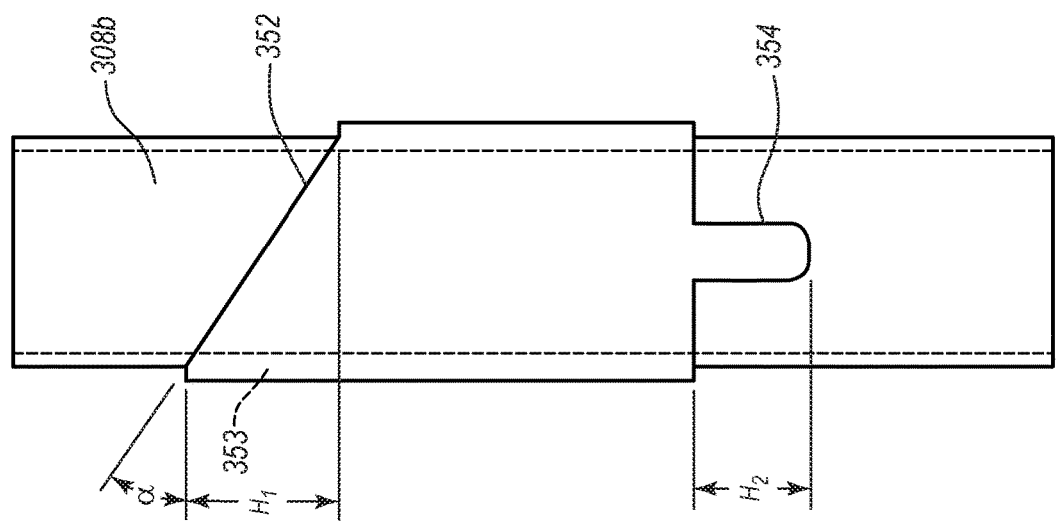
FIG. 10 is an elevation view of the housing component of FIG. 13.
Figure 9:
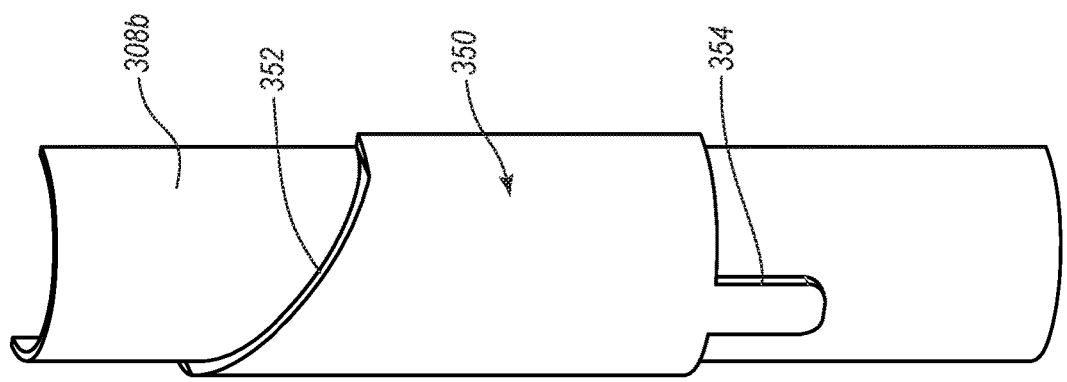
FIG. 9 is a perspective view of one of the housing components depicted in FIG. 8.
Figure 12:
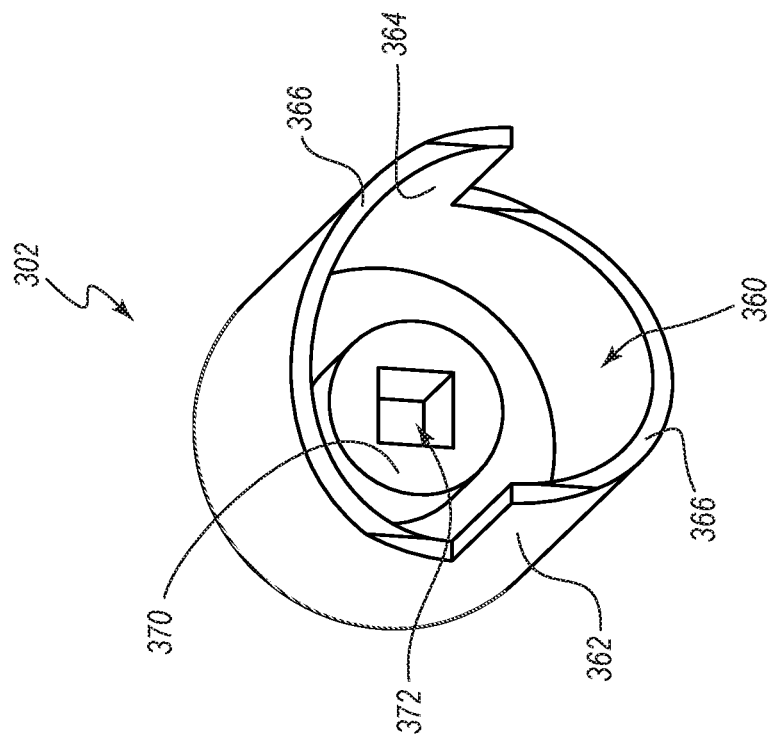
FIG. 12 is a bottom perspective view of the proximal cap of FIG. 11.
Figure 11:
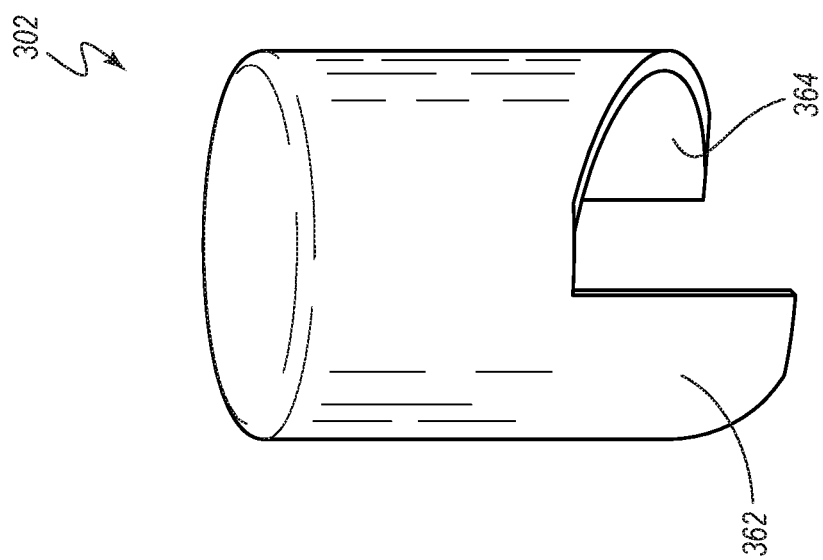
FIG. 11 is a top perspective view of an embodiment of a proximal cap portion of the driver, which may also be referred to as a winding cap.
Figure 14:
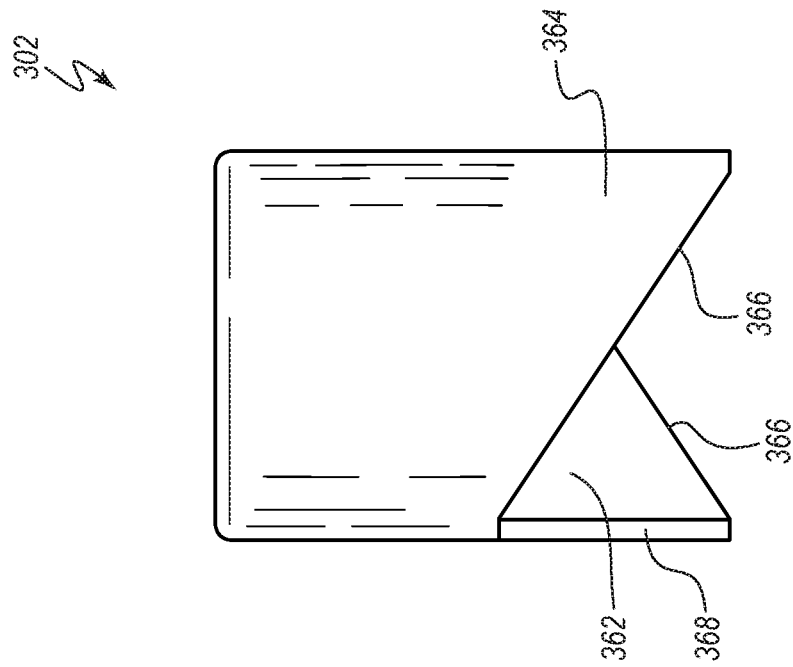
FIG. 14 is a further elevation view of the proximal cap of FIG. 11 rotated about a longitudinal axis thereof 90 degrees in a clockwise direction, as viewed from above.
Figure 13:
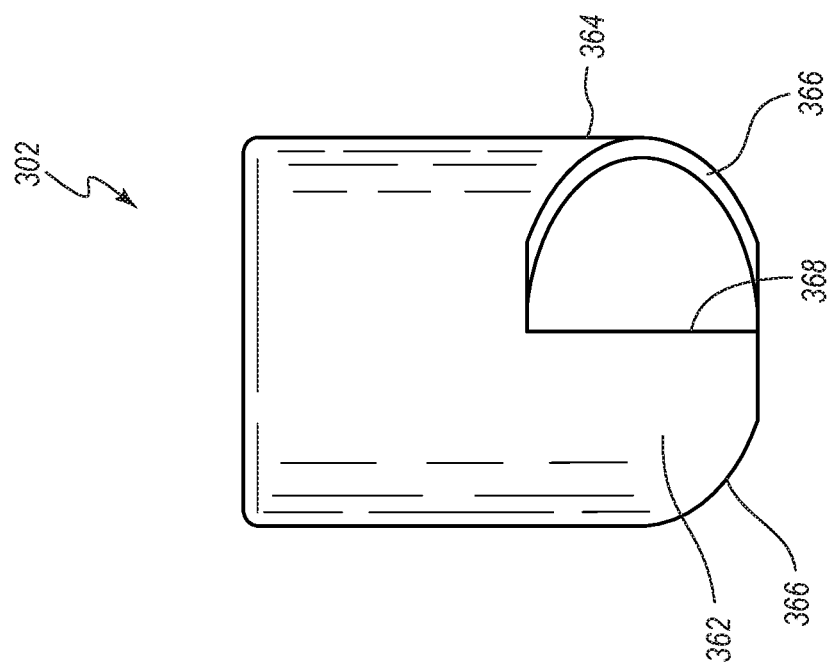
FIG. 13 is an elevation view of the proximal cap of FIG. 11.

FIGS. 9 and 10 depict an exterior of the housing component 308b. The housing component 308b can define two thicknesses. At distal and proximal ends thereof, the thickness can be less than at an expanded or thickened region 350. The narrower proximal end can readily receive the proximal cap thereover, whereas the narrower distal end can readily receive the distal cap thereover, as shown in FIGS. 6 and 7. The thickened region 350 can define active or action surfaces at both proximal and distal ends thereof for interacting with the proximal and distal caps 302, 204, respectively.

In particular, in the illustrated embodiment, a proximal end of the thickened region 350 defines a ramp 352, which may also be referred to as a camming surface. The ramp 352 can define an angle α relative to a horizontal plane (in the orientation of FIG. 10), or stated otherwise, relative to a lateral plane that is perpendicular to a longitudinal axis of the housing component 308b. The ramp 352 can further define a height $H_1$ in the longitudinal direction.

Adjacent to the upper end of the ramp 352, the thickened region 350 also defines a stop or abutment 353 (see also FIG. 8). The abutment 353 can extend longitudinally for a distance at least as great as the height $H_1$.

In the illustrated embodiment, a distal end of the thickened region 350 defines a stop or tab 354 that extends longitudinally. The tab 354 defines a height H2 in the longitudinal direction.

As previously noted, the housing component 308a can be identical to the housing component 308b. Accordingly, the housing component 308a can include each of the features discussed with respect to the housing component 308b, such as a thickened region 350 and its associated features.

With reference to FIGS. 11-14, in certain embodiments, the proximal cap 302 defines a cavity 360 into which the proximal end of the housing 300 is received. The cap 302 can further define a pair of arms 362, 364. Each arm 362, 364 can define active or action surfaces configured to interact with the action surfaces defined by the distal ends of the thickened regions 350 of the housing components 308a, 308b. In particular, each arm 362, 364 can define a ramp or camming surface 366, that is configured to alternatingly interact with the ramp or camming surface 352 of the housing component 308a and with the ramp or camming surface 352 of the housing component 308b. Each arm 362, 364 likewise can define a stop or abutment 368 that can interact with the abutments 353 of the housing components 308a, 308b. In some embodiments, each abutment 368 can define the same height $H_1$ as that defined by the abutments 353 of the housing components 308a, 308b (see FIG. 10).

The proximal cap 302 can further define a coupling extension 370 configured to couple with the coupling block 316. For example, in the illustrated embodiment, the coupling extension 370 defines a recess 372 having a square profile within which a complementary squarely shaped coupling block 316 (see FIG. 23) can be received. The coupling block 316 can be attached to the proximal cap 302 within the recess 372 in any suitable manner. In other embodiments, the coupling block 316 can be integrally formed with the proximal cap 302, or stated otherwise, the proximal cap 302 and the coupling block 316 can be integrally formed as a unitary component and/or the proximal cap 302 may itself define one or more features of the coupling block 316. In each instance discussed in the present paragraph, it may be said that the proximal cap 302 is coupled with the coupling block 316.

Figure 16:
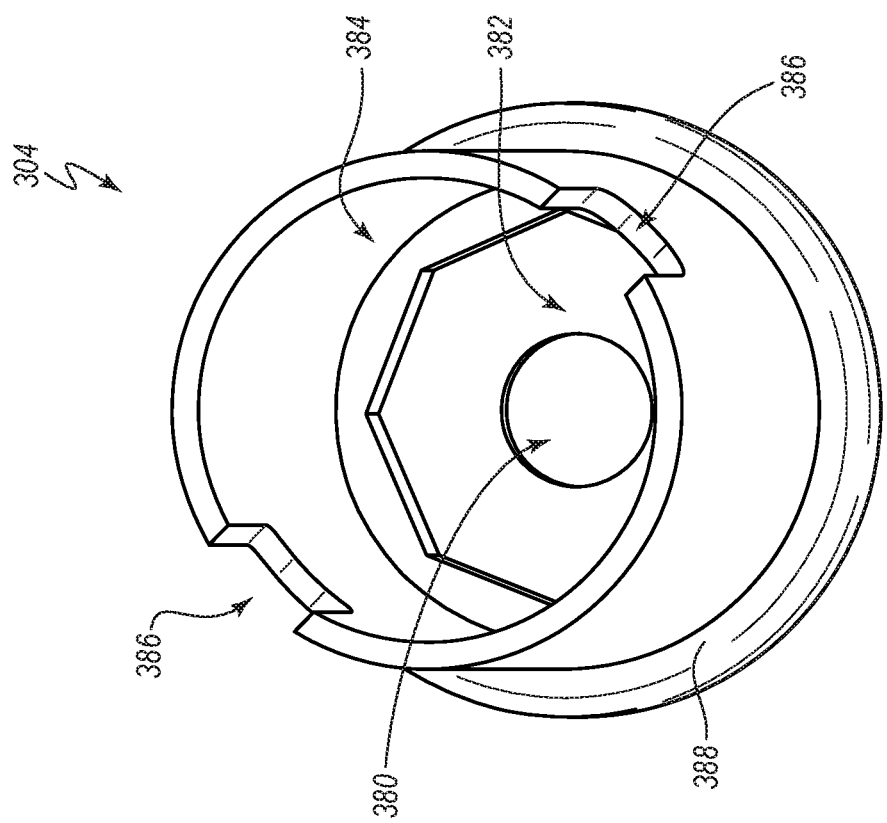
FIG. 16 is a top perspective view of the distal cap.
Figure 15:
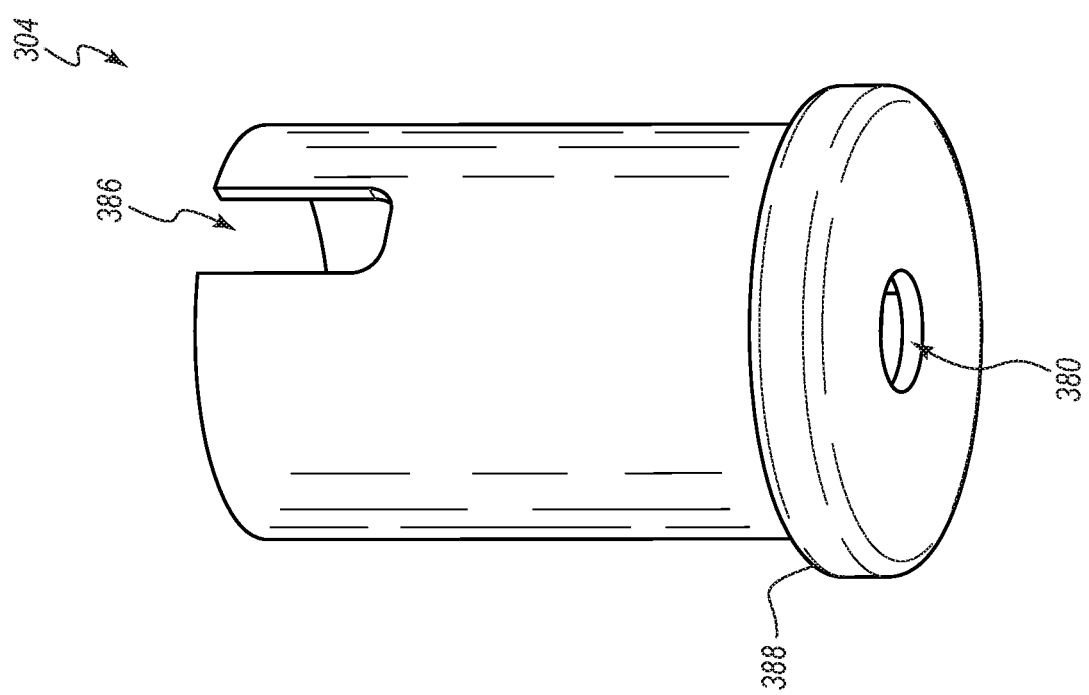
FIG. 15 is a bottom perspective view of an embodiment of a distal cap portion of the driver, which is also referred to herein as a handle.

With reference to FIGS. 15 and 16, the handle 304 can define an opening 380 through which the drive shaft 320 can extend. At an interior thereof, the handle 304 can define a recess 382 for receiving the stop 324. In the illustrated embodiment, the recess 382 defines an octagonal profile, which is complementary to an octagonal profile of the stop 324. Such an arrangement can prevent the stop 324 from rotating relative to the handle 304. Stated otherwise, the stop 324 can be attached to the handle 304 so as to be rotationally fixed relative to the cap. Any other suitable configuration (complementary or otherwise) is contemplated for the stop 324 and the recess 382. In some embodiments, the stop 324 may be integrally formed with the handle 304 as a single unitary component and/or the handle 304 may itself define one or more features of the stop 324. In each instance discussed in the present paragraph, it may be said that the handle 304 is coupled with the stop 324.

The handle 304 can further define a cavity 384 into which a distal end of the housing 300 can be received. A lower end of the cavity 384 can define a portion of the distal cavity 311 of the driver 101, which was discussed previously with respect to FIG. 7.

The handle 304 can further define a pair of slots 386 that are configured to interact with the tabs 354 defined by the housing 300 to prevent rotation of the handle 304 relative to the housing 300. Together, the slots 386 and the tabs 354 can function as a rotation restraint 387, which can delimit an amount of rotation the handle 304 can exhibit relative to the housing 300. The slots 386 can permit relative longitudinal translation between the housing 300 and the housing 304. Stated otherwise, the rotation restraint 387 may permit translation or relative longitudinal movement between the handle 304 and the housing 300. In the illustrated embodiment, the tabs 354 are positioned at diametrically opposite sides of the handle 304. In some embodiments, a depth of each tab 354 is at least as great as the height H2 defined by the tabs 354.

The handle 304 can further define an outward protrusion or shelf 388, which can facilitate use of the driver 101. For example, a user can press downwardly or distally on the shelf 388 to actuate the driver 101. The shelf 388 can enhance the grip or purchase that a user can have on the handle 304.

Figure 17:
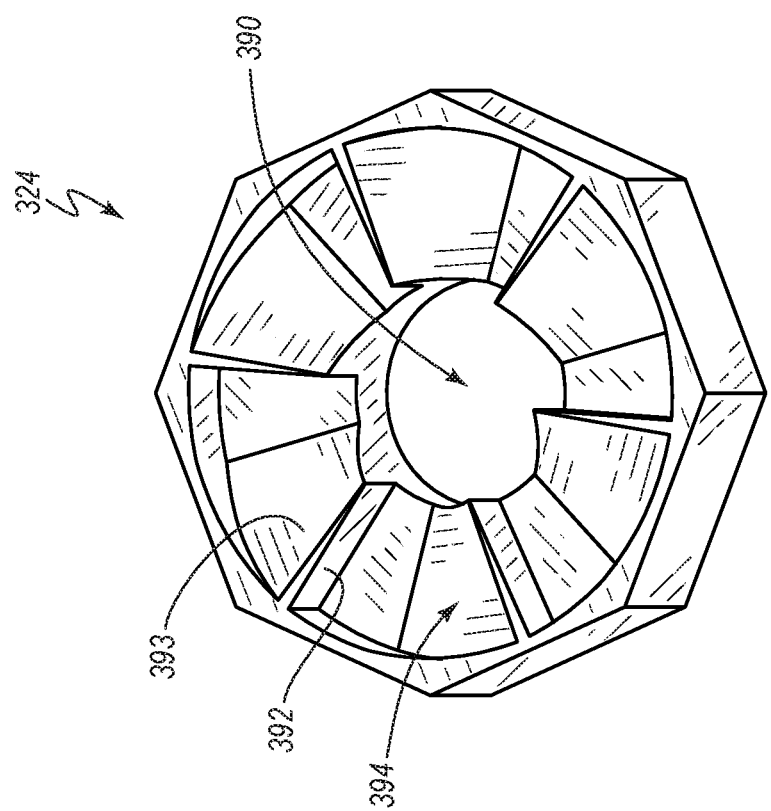
FIG. 17 is a top perspective view of an embodiment of a stop compatible with the driver.

With reference to FIG. 17, the stop 324 can define a central opening 390 through which the drive shaft 320 can extend. The stop 324 can further define one or more stopping surfaces 392 that are configured to prevent rotation of the drive shaft 320 in at least one direction. In the illustrated embodiment, the stop 324 defines a plurality of stopping surfaces 392 that are configured to prevent clockwise rotation of the drive shaft 320 when engaged with the drive shaft 320, or more particularly, with the clutch 322 to which the drive shaft 320 is fixedly secured. In the illustrated embodiment, each stopping surface 392 is defined by a substantially vertical face, as compared with a longitudinal axis extending through the opening 390. For example, in various embodiments, planes defined by each stopping surface 392 can intersect along the longitudinal axis or can extend parallel to the longitudinal axis. The stop 392 can further define one or more angled or camming surfaces or ramps 393 that may selectively permit or prevent counterclockwise movement of the clutch 322, depending on the amount of longitudinal force applied thereto, as further discussed below.

The illustrated stop 324 is formed as a clutch receiver that is configured to interact with the clutch 322. The stop 324 comprises a plurality of teeth 394 that define the stopping surfaces 392 and the ramps 393. In particular, each tooth 394 includes a stopping surface 392 and a ramp 393.

In some instances, the stop 324 and the clutch 322 can act as a ratchet system. For example, in the illustrated embodiment, the substantially vertically oriented stopping surfaces 392 of the teeth 394 prevent clockwise rotation when engaged with complementary surfaces of the clutch 322, but the ramps 393 of the teeth 394 can interact with complementary surfaces of the clutch 322 to urge the clutch 322 proximally and permit counterclockwise rotation of the clutch 322, under some circumstances. For example, with reference again to FIG. 7, it can be possible to increase an amount of potential energy stored by the torsion spring 314 by winding up (e.g., rotationally displacing) the torsion spring 314 via the drive shaft 320, rather than via the winding cap 302, and this winding can proceed in a ratcheting manner as discussed further below.

In other or further instances, the stop 324 and the clutch 322 can lock to prevent both clockwise and counterclockwise rotation of the drive shaft 320. For example, with reference again to FIG. 7, in the illustrated embodiment, when the partition 340 of the housing 300 maintains the clutch 322 engaged with the stop 324, the stopping surfaces 392 and the ramps 393 interact with complementary surfaces of the clutch 322 to prevent both clockwise and counterclockwise rotation of the drive shaft 320, as discussed further below.

Figure 18:
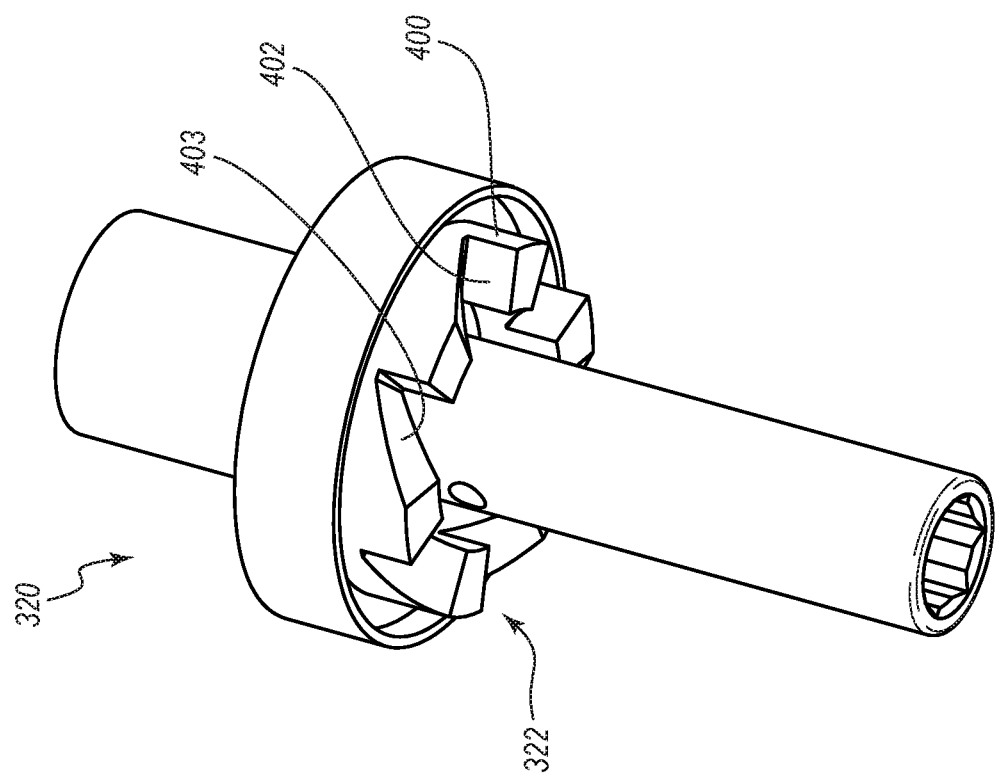
FIG. 18 is a bottom perspective view of an embodiment of a drive shaft that is compatible with the driver of FIG. 1.

With reference to FIG. 18, the drive shaft 320 includes the clutch 322. The clutch 322 may be integrally formed with the drive shaft 320, or may otherwise be fixedly secured thereto (e.g., the clutch 322 may be fixedly coupled with the drive shaft 320 in any suitable manner). In the illustrated embodiment, the clutch 322 defines a plurality of teeth 400 configured to interact with the teeth 394 of the stop 324 in manners previously discussed. Each tooth 400 can include a stopping surface 402 that interacts with a stopping surface 392 of the clutch receiver 324 to prevent relative rotation of the clutch components. Each tooth 400 can likewise define a ramp 403 that interacts with one or more ramps 393 of the clutch receiver 324 to selectively permit or prevent rotation of the clutch components, depending on how and where forces are applied to the driver 101, as discussed further below.

Figure 19:
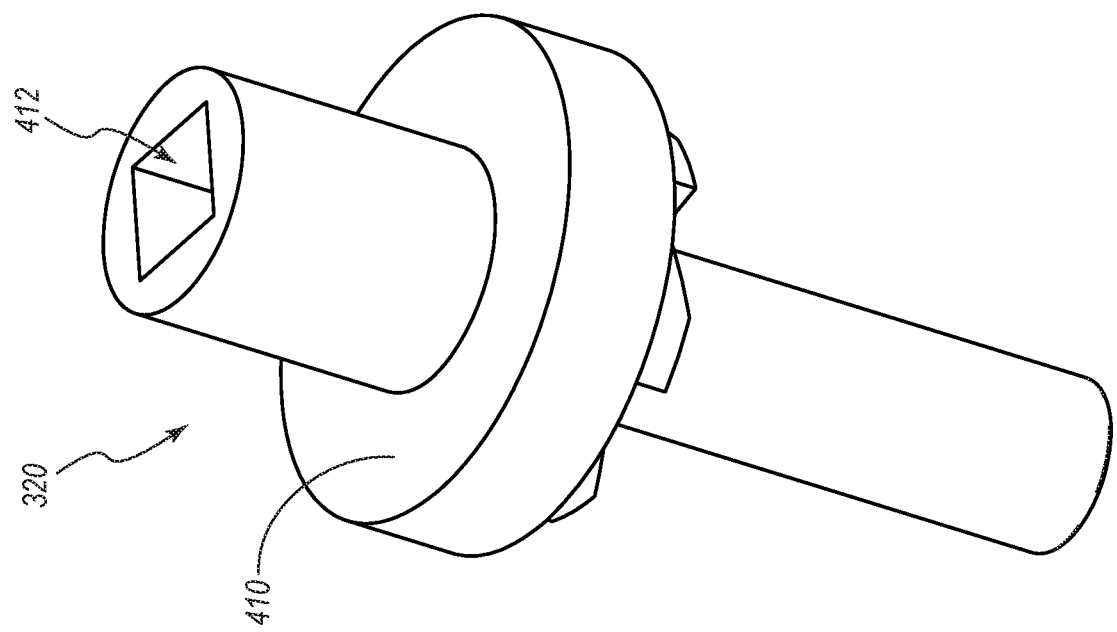
FIG. 19 is a top perspective view of the drive shaft.

With reference to FIG. 19, the drive shaft 320 further defines a substantially disk-shaped region or annulus 410. As previously discussed, the partition 340 of the housing 300 can be positioned between the annulus 410 and the washer 325. In some instances, the annulus 410 can prevent relative longitudinal translation between the housing 300 and the drive shaft 320. For example, with reference to FIG. 7, if a user holds onto the handle 304 (e.g., only the handle 304) and presses forward (i.e., in a distal direction) against a bone with sufficient force, the reactive force of the bone can push proximally on the drive shaft 320. The annulus 410 of the drive shaft 320 thus can push proximally on the partition 340 of the housing 300, which can cause the housing 300 to move proximally relative to the handle 304. Both the drive shaft 320 and the housing 300 may move in the proximal direction, relative to the handle 304, in unison.

The drive shaft 320 can further define a recess 412 having a square profile within which a squarely shaped coupling block 318 (see FIG. 22) can be received. The coupling block 318 can be attached within the recess 412 in any suitable manner. In other embodiments, the coupling block 318 may be incorporated into the drive shaft 320, or stated otherwise, the drive shaft 320 and the coupling block 318 may be integrally formed as a unitary component and/or the drive shaft 320 may itself define features of the coupling block 318. In each instance discussed in the present paragraph, it may be said that the drive shaft 320 is coupled with the coupling block 316.

Figure 20:
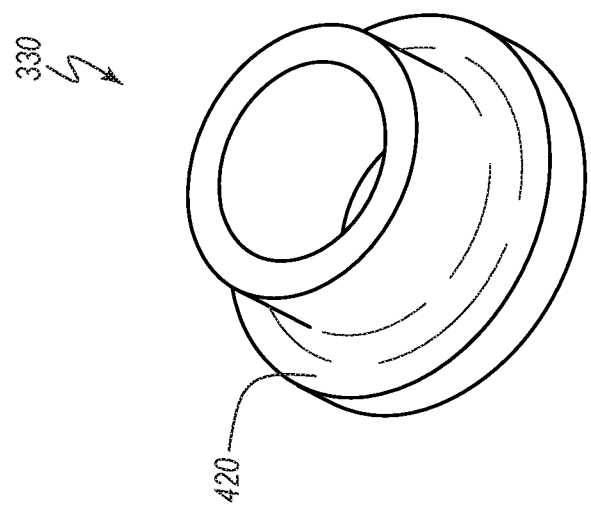
FIG. 20 is a top perspective view of an embodiment of a catch member that is couplable to the drive shaft.

With reference to FIG. 20, the collar 330 can define a laterally projecting surface or ledge 420 against which a distal end of the compression spring 334 can press. In some embodiments, the laterally projection surface or ledge 420 may instead be defined by a portion of the drive shaft 320, or stated otherwise, may be integrally formed therewith. The collar 330 may also or alternatively be referred to as a catch member, a shelf, etc.

Figure 21:
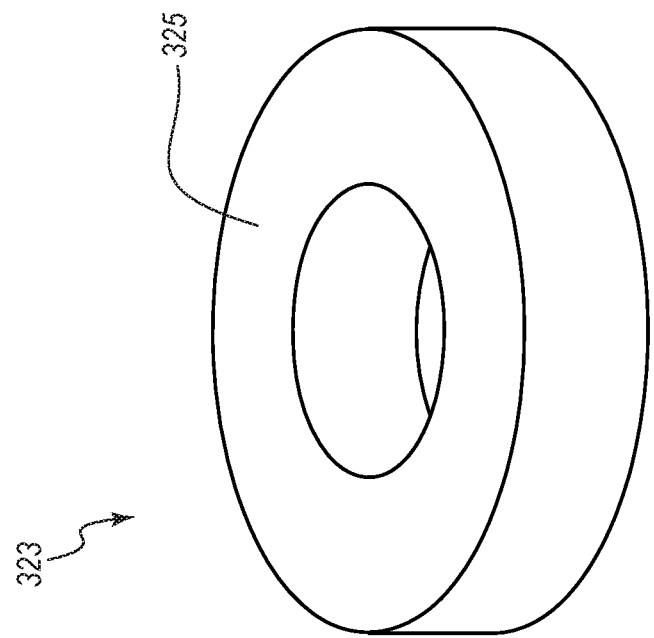
FIG. 21 is a top perspective view of an embodiment of a bearing that is couplable to the drive shaft.

FIG. 21 depicts an embodiment of the bearing 323. In the illustrated embodiment, the bearing 323 is formed as an annularly shaped washer 325. Any other suitable arrangement is contemplated. For example, other structures, such as laterally projecting rods or ribs can be secured to or otherwise extend from the drive shaft 320. The bearing 323 can substantially maintain alignment of a rotational axis of the drive shaft 320 with a longitudinal axis of the driver 101 during rotation of the drive shaft 320 relative to the handle 304. For example, an outer surface of the washer can interact with an inner surface of the housing 300 to center the drive shaft 320 relative to the housing throughout a drilling event.

In other or further instances, the bearing can prevent relative longitudinal translation between the housing 300 and the drive shaft 320. For example, as previously described, in some instances a user may hold onto the handle 304 (e.g., only the handle 304) and press forward (i.e., in a distal direction) against a bone with sufficient force for a reactive force from the bone to push proximally on the drive shaft 320, which in turn causes the drive shaft 320 to push proximally on the partition 340 to move the housing 300 proximally relative to the handle 304. Upon removal of the user-applied force, the compression spring 334 can urge the drive shaft 320 to move distally relative to the handle 304. The washer 325 or other structure projecting from the drive shaft 320 can, in turn, press distally on the partition 400 of the housing 300 to move the housing 300 distally relative to the handle 304.

Figure 23:
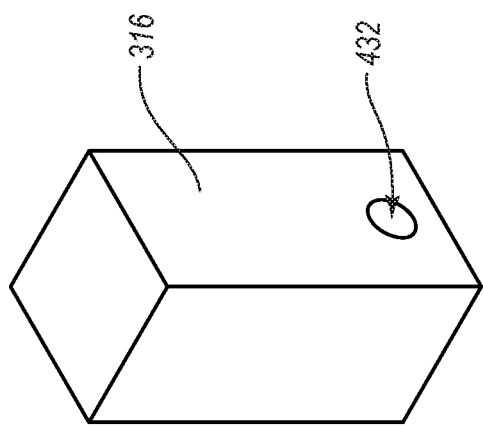
FIG. 23 is a top perspective view of an embodiment of a coupler that is configured to connect the proximal cap to the biasing member.
Figure 22:
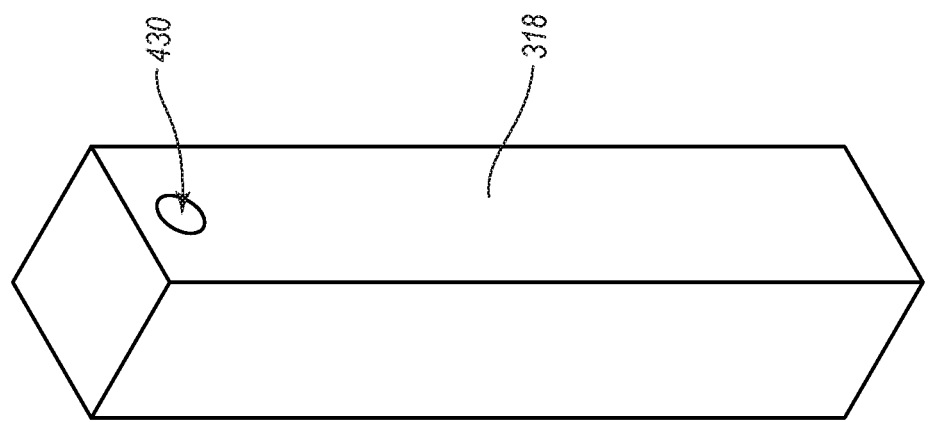
FIG. 22 is a top perspective view of an embodiment of a coupler that is configured to connect the drive shaft with a biasing member.

FIGS. 22 and 23 depict the coupling blocks 318, 316, respectively. Each block 318, 316 can define a coupling channel 430, 432, respectively, through which a respective distal and proximal end of the torsion spring 314 can be passed to couple the torsion spring 314 to the drive shaft 320 and the proximal cap 302, respectively. This coupling arrangement is also depicted in FIG. 7. The coupling blocks 318, 316 can define any suitable profile, which may be complementary to the profiles defined by the cavities 412, 372 and can be configured to prevent rotation between the coupling blocks 318, 316 and the drive shaft 320 and the proximal cap 302, respectively. In the illustrated embodiments, the coupling blocks 318, 316 define substantially square perimeters.

With further reference to FIG. 7, in certain embodiments, the driver 101, or various components thereof, may advantageously be secured together with few or no adhesive bonds. For example, in some embodiments, each of the proximal cap 302 and the handle 304 is secured to the housing 300 without any adhesive being used to directly adhere these components together. The housing components 308a, 308b may be devoid of any adhesive bonds. The torsion spring 314 may be connected at its proximal end to the proximal cap 302 via the coupling block 316, and may be connected at its distal end to the drive shaft 320 via the coupling block 318. The torsion spring 314 may be stretched or otherwise displaced during such assembly so as to provide an inwardly directed bias at each of its proximal and distal ends. Accordingly, the torsion spring 314 can pull distally on the coupling block 316, and hence on the proximal cap 302. Similarly, the torsion spring 314 can pull proximally on the coupling block 318, and hence on the drive shaft 320, the collar 330, the compression spring 334, and the handle 304. That is, the proximally directed forces on the drive shaft 320 pull proximally on the distal end of the compression spring 334, which causes the proximal end of the compression spring 334 to urge the handle 304 in the proximal direction. Thus, the torsion spring 314 provides a bias on each of the proximal and distal caps 302, 304 that tends to keep them tightly secured to the ends of the housing 300. When the torsion spring 314 is preloaded with a desired amount of potential energy, or stated otherwise, when the torsion spring 314 is pre-wound or pre-displaced to provide a desired amount of torsion, the inwardly directed bias provided thereby may be sufficiently strong to maintain the driver 101 in a fully assembled state.

Operation of the driver 101 will now be discussed, with continued reference to FIG. 7. Prior to a drilling event, the driver 101 can be wound to store energy in the torsion spring 314. Two illustrative forms of winding will be discussed.

In some instances, one or more of the handle 304 and the housing 300 can be held (e.g., by an end user or in a manufacturing process) while the proximal cap 302 is rotated. In the illustrated embodiment, the proximal cap 302 is rotated in a clockwise direction (as viewed from above) to load the torsion spring 314. Rotation of the cap 302 in this manner urges the ramps or camming surfaces 366 of the proximal cap 302 against the ramps or camming surfaces 352 of the housing 300. As can be appreciated from FIG. 10, this relative movement of the camming surfaces 352, 366 urges the proximal cap 302 upward—that is, proximally relative to the housing 300—as the camming surfaces 366 of the proximal cap 302 slide upwardly over the camming surfaces 352 of the housing 300.

Eventually, the bottom (i.e., distal) ends of the camming surfaces 366 of the proximal cap 302 reach the top (i.e., proximal) ends of the camming surfaces 352 of the housing 300. Additional clockwise rotation of the proximal cap 302 temporarily brings the camming surfaces 366, 352 out of contact with each other. The distally directed bias on the cap 302 provided by the extended or expanded torsion spring 314 pulls the proximal cap 302 downwardly until the camming surfaces 366 of the proximal cap 302 again come into contact with the camming surfaces 352 of the housing 300. Stated otherwise, the camming surfaces 366 of the proximal cap 302 alternatingly rise along the camming surfaces 352 of the housing 300 until they reach the top thereof—specifically, after undergoing one half turn—and then are pulled down by the torsion spring 314 into contact again with the camming surfaces 352 of the housing 300. Looking at the path followed by just one of the camming surfaces 366 of the proximal cap 302, the camming surface 366 rises along a first of the two camming surfaces 352 of the housing 300 and then falls into contact with the second of the two camming surfaces 352 of the housing 300.

At any point during winding, the proximal cap 302 can be released or otherwise permitted to rotate relative to the housing 300. When this occurs, the camming surfaces 366 of the proximal cap 302 are either brought into contact with or remain in contact with the camming surfaces 352 of the housing 300 due to the inward bias provided by the torsion spring 314, which urges the proximal cap 302 distally. The magnitude of this bias increases as the torsion spring 314 is wound. Interaction of the camming surfaces 366, 352 causes the cap 302 to rotate counterclockwise relative to the housing 300 until the abutments 368 of the proximal cap 302 come into contact with the abutments 353 of the housing 300. Interference between the abutments 368, 353 prevents any (or any further) rotation of the proximal cap 302 relative to the housing 300. The proximal cap 302 and the housing 300 may be said to operate as a ratchet system.

In this manner, the torsion spring 314 can be wound or loaded in one-half turn increments. Such an arrangement can readily allow a user to, for example, hold the housing 300 with one hand and rotate the proximal cap 302 clockwise with the other for one half, or a little over one half, of a turn. The user can then release the proximal cap 302 while maintaining a grip on the housing 300. This can permit the proximal cap 302 to rotate counterclockwise until the abutments 368, 353 engage and prevent further unwinding of the torsion spring 314. During this time, the user can readjust his or her grip on the proximal cap 302 to then rotate the proximal cap 302 clockwise again for another half turn.

In some embodiments, the torsion spring 314 grows longitudinally in length by an amount equal to a diameter of the wire every time the proximal cap 302 undergoes a full turn. As a result, the proximal cap 302 may be positioned higher and higher relative to the housing 300 after each half-turn of the proximal handle 304. Stated otherwise, a gap may begin to form between the camming surfaces 366 of the proximal cap 302 and the camming surfaces 352 of the housing 300 after one or more half-turns of the proximal cap 302. In such instances, it may be possible to determine how much energy has been stored in the torsion spring 314 by a size of this gap, which corresponds to an amount of longitudinal growth of the spring 314 due to the number of turns the spring 314 has been wound.

In some embodiments, a marking or other indicator, such as any suitable indicia on the housing 300 and/or on the proximal cap 302 may be used to show that a sufficient amount of energy has been stored in the torsion spring 314. In other instances, a stop on the housing 300 and/or on the proximal cap 302 may prevent the proximal cap 302 from being displaced proximally relative to the housing 300 by an amount greater than that needed to load the torsion spring 314 with a predetermined amount of potential energy.

In still other or further embodiments, the height $H_1$ of the camming surfaces 352 (see FIG. 10) can be adjusted to ensure that the torsion spring 314 is not overwound. For example, the camming surfaces 366 of the proximal cap 302 may continue to separate from the camming surfaces 352 of the housing as the torsion spring 314 grows in length due to winding. When the gap between the camming surfaces 366, 352 grows to an amount equal to the height $H_1$, any additional half-turns of the proximal cap 302 will fail to store any further energy in the torsion spring 314. That is, once the user releases the proximal cap 302 after having imparted the additional amount of clockwise turning, the torsion spring 314 will cause the proximal cap 302 to rotate counterclockwise until the abutments 368, 353 engage with each other again. Thus, in some embodiments, the height H₁ of the camming surfaces 352 can delimit an amount of energy that can be stored in the torsion spring 314.

Any suitable mechanism for showing that the driver 101 has been loaded with a desired amount of energy is contemplated. For example, as previously discussed, a size of a gap between the camming surfaces 366, 352 can indicates amount of energy in the driver 101. A predetermined gap at which appropriate amount of energy is stored can be marked to indicate that enough energy has been stored. In some embodiments, the gap may have a height within a range of from about 5 to 15 diameters of a wire of the torsion spring 314. For example, a suitable amount of energy may be stored after from about 10 to about 30 half-turns of the proximal cap 302.

In other instances, a suitable amount of energy may be stored in the driver 101 after only a single or partial turn of the proximal cap 302. An alignment of markings on the cap 302 and the housing 300, or any other suitable indicia system, may indicate that the system is in a wound, energized, or loaded state. Any other suitable number of turns or partial turns, and any other mechanism of indicating the amount of turning that has occurred to indicate an amount of energy that has been stored, are contemplated.

In other instances, the torsion spring 314 can be wound using the drive shaft 320. For example, the housing 300 can be held (e.g., by an end user or during a manufacturing process) while the drive shaft 320 is rotated. In the illustrated embodiment, a hex key or other suitable bit can be inserted into the socket 329 and rotated in a counterclockwise direction (as viewed from above [proximal-to-distal view]; clockwise as viewed from below [distal-to-proximal view]) to load the torsion spring 314. Rotation of the cap drive shaft 320 in this manner urges the ramps or camming surfaces 403 of the drive shaft 320 against the ramps or camming surfaces 393 of the stop 324. As can be appreciated from FIGS. 17 and 18, this relative movement of the camming surfaces 403, 393 urges the handle 304 downward—that is, distally relative to the housing 300—as the camming surfaces 403, 393 slide past one another while the housing 300, and hence the partition 340, are held still.

Each partial turn that brings one set of camming surfaces 403, 393 past each other incrementally increases the potential energy stored by the torsion spring 314. When winding is complete, camming surfaces 403, 393 can slide past each other in the opposite (e.g., clockwise) direction under the inward bias provided by the torsion spring 314 until the stopping surfaces 402, 392 come into contact with each other. The stopping surfaces 402, 392 prevent further unwinding of the torsion spring 314. The clutch 322 and the stop 324 may be said to interact with each other as a ratchet system.

During winding of the torsion spring 314 in this manner, interference between the abutments 368, 353 of the proximal cap 302 and the housing 300 prevent rotation of the proximal cap 302 relative to the housing 300, thus maintaining the proximal end of the torsion spring 314 rotationally fixed. However, as previously noted, as the torsion spring 314 is wound, a length of the torsion spring 314 can increase. This can cause the cap 302 to rise, or move proximally, relative to the housing 300. Thus, as the drive shaft 320 is rotated at the distal end of the driver 101 to wind the torsion spring 314, the abutments 368, 353 can maintain the proximal cap 302 in a fixed rotational relationship relative to the housing 300 while sliding longitudinally past one another as the proximal cap 302 rises.

Winding of the torsion spring 314 may be performed by a practitioner prior to (e.g., immediately prior to, or long in advance of) using the driver 101 to drill an access assembly 109 into a bone of a patient. For example, in some embodiments, the driver 101 may be provided in an uncharged or non-loaded state, or may be reusable, and a practitioner may wind or rewind the spring 314 prior to a drilling event. The practitioner may, for example, choose to pre-wind the torsion spring 314 so as to ensure the driver 101 is ready in the event of an emergency. The practitioner may choose to keep the driver 101 in the pre-loaded state when stored in a bag or other gear.

In other instances, the winding may be performed during a manufacturing step. For example, in some instances, the driver 101 may be intended for a single use or may be non-rewindable or non-reloadable. During manufacture of some embodiments of such a driver 101, the proximal cap 302 may be rotated relative to the housing 300 to wind or load the torsion spring 314 in manners such as previously discussed. The proximal cap 302 may then be fixed relative to the housing 300 in any suitable manner so as to prevent further relative rotation. For example, in some embodiments, a locking pin may be used to prevent relative movement of the proximal cap 302 and the housing 300 after the torsion spring 314 has been wound. In other embodiments, tape, adhesive, or any other suitable fixation mechanism may be used to secure the proximal cap 302 to the housing 300 after the spring 314 has been loaded by a desired amount.

In other or further embodiments, the proximal cap 302 may be fixedly secured to the housing prior to winding the torsion spring 314. For example, the torsion spring 314 may be wound via the drive shaft 320, rather than via the proximal cap 302, in manners such as previously discussed. In certain of such embodiments, sufficient space for longitudinal expansion of the spring 314 during loading may be provided within the driver 101. In some embodiments, the camming and abutment features of the housing and the proximal cap 302 may be omitted.

At any suitable stage, such as prior to winding the driver 101 (e.g., prior to winding the driver via the proximal cap 302), after winding the driver 101 (e.g., after winding the driver via the proximal cap 302 or via the drive shaft 320), or upon removing a pre-loaded driver 101 from packaging, an access assembly 109 can be coupled to the drive shaft 320 of the driver 101, in manners such as previously described. That is, the coupling shaft 122 of the obturator assembly 102 can be inserted into the socket 328 of the drive shaft 320. The access assembly 109 can be in a coupled state, such as depicted in FIG. 24. For example, the access assembly 109 may originally be provided to the end user in a coupled state. In other instances, the user may couple the various components of the access assembly 109 prior to use.

Any suitable access assembly 109 is contemplated. For example, certain embodiments may be employed with the access assemblies disclosed in U.S. Patent Application Publication No. 2018/0125465, titled INTRAOSSEOUS ACCESS DEVICES, SYSTEMS, AND METHODS, corresponding to U.S. patent application Ser. No. 15/787,671, filed Jan. 26, 2018; and U.S. Patent Application Publication No. 2018/0256209, titled SAFETY SHIELDS FOR ELONGATED INSTRUMENTS AND RELATED SYSTEMS AND METHODS, corresponding to U.S. patent application Ser. No. 15/914,964, filed Mar. 7, 2018, the entire contents of each of which are hereby incorporated by reference herein.

The illustrated access assembly 109 closely resembles embodiments of access assemblies disclosed in U.S. patent application Ser. No. 15/914,964 (the '964 Application). For example, the access assembly 109 can include the safety shield 105, which can automatically clip to the distal end of the obturator 104 as the obturator assembly 102 is withdrawn from the needle assembly 202. In particular, after the needle assembly 202 has been drilled into the bone of a patient, the obturator assembly 102 can be withdrawn from the needle assembly 202 as the needle assembly 202 remains in place within the bone of the patient. Automatic attachment of the shield 105 to the distal tip of the obturator 104 shields the distal tip from inadvertent contact therewith (e.g., prevents inadvertent sticking).

As discussed more fully in the '964 Application, the safety shield 105 can include a body 160 (e.g., formed of metal or any other suitable resilient material) having inwardly biased resilient arms 162, 163 with transverse extensions 172, 173 at the proximal end thereof. The transverse extensions 172, 173 define keyhole-shaped openings 175 each having a first region that is of relatively larger diameter to be able to slide over the exterior surface of the proximal, larger-diameter portion of the obturator 104 and a second region that is relatively smaller diameter to come to rest within the recess 150 and grip a narrowed portion of the obturator 104 once the obturator 104 has been withdrawn proximally relative to the shield 105 by a sufficient amount.

The resilient arms 162, 163 include outward protrusions 178, 179 that couple the shield 105 with the needle hub 203. The arms 162, 163 are maintained in their outward deflection by the keyhole-shaped openings 175. Interaction of the protrusions 178, 179 with the annular groove 227 of the needle hub 203 maintains the shield 105 in fixed longitudinal relation to the needle hub 203 as the obturator 104 is retracted proximally. Once the recess 150 enters the keyhole-shaped openings 175, the arms 162, 163 spring inwardly to grip the narrowed neck of the obturator 104, which causes the protrusions 178, 179 to exit the annular groove 227 and release the shield 105 from the needle hub 203. Thus, the shield 105 couples more securely (e.g., attaches to) the obturator 104 and decouples from the needle hub 203.

In the illustrated embodiment, the safety shield 105 includes two components in addition to the body 160. At an interior of the body 160 is disposed a guide 160 that can help maintain a desired longitudinal alignment of a longitudinal axis of the safety shield 105 with a longitudinal axis of the obturator 104. Stated otherwise, the guide 160 inhibits rotation of the safety shield 105 about axes perpendicular to the longitudinal axis of the safety shield 105 during translation of the obturator 104 relative to the safety shield 105. Further, the illustrated safety shield 105 includes a biasing member 185, such as a resilient O-ring, that provides additional inward biasing to that of the outwardly deflected resilient arms 162, 163.

Any of the foregoing processes may be part of one or more methods of using the driver 101 or, more generally, of using the system 100. Further stages of illustrative methods of using the system 100 are depicted in FIGS. 25A-25D.

Figure 25A:
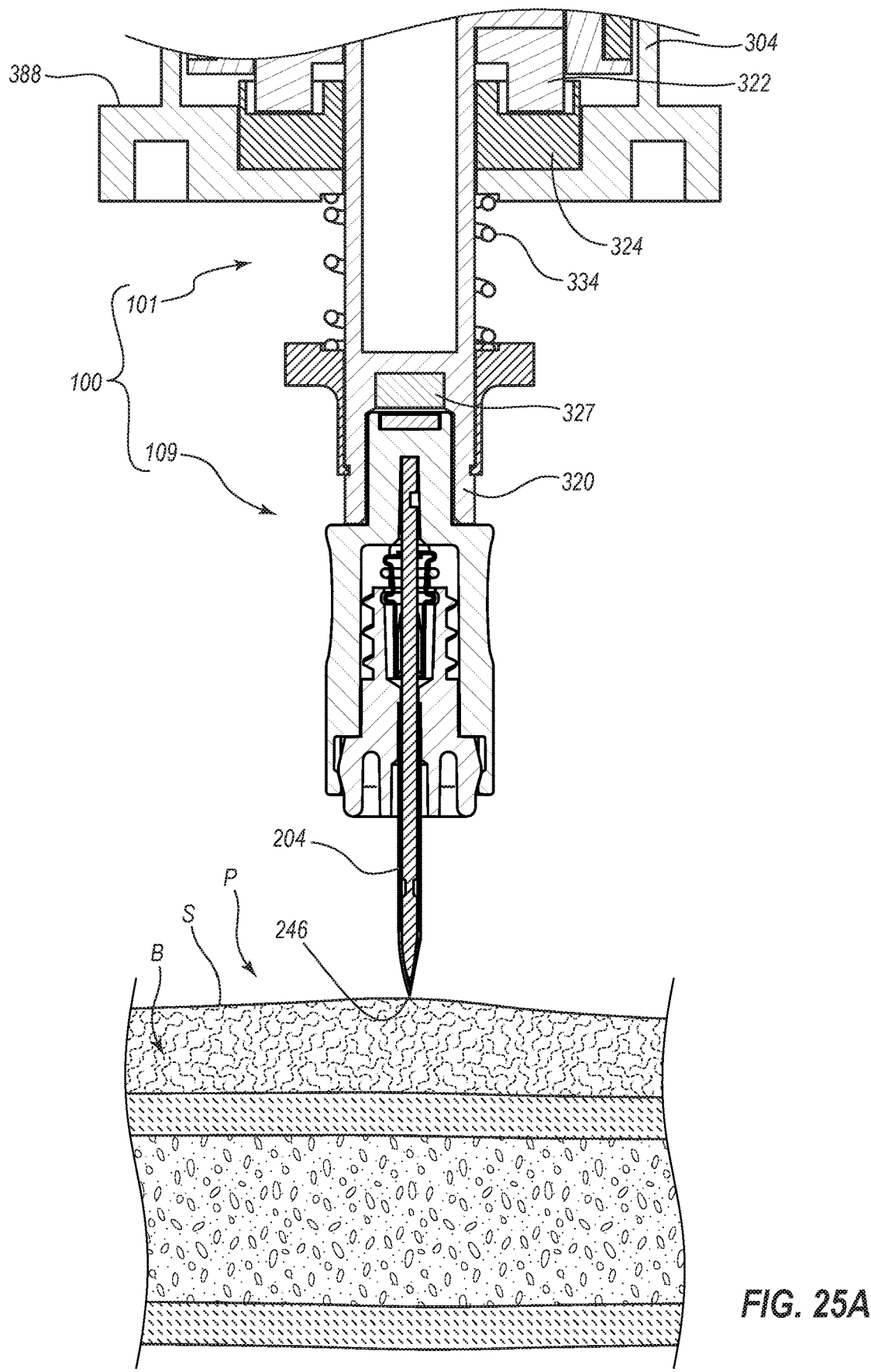
FIG. 25A depicts a stage of an illustrative method in which a distal end of the driver is coupled to the access assembly.

With reference to FIG. 25A, the access assembly 109 can be coupled to the drive shaft 320 in manners such as previously described. The user can grip the handle 304 and urge the system 100 distally toward the skin S of a patient P. In FIG. 25A, the system 100 is shown making initial contact with the skin S. Stated otherwise, the distal tip 246 of the needle 204 is at the surface of the skin S. The distal tip 246 of the needle 204 may initially be positioned at the surface of the skin S of the patient P at a position above a bone B into which access is desired. The user may grip the handle 304 and apply force distally to urge the needle 204 through the skin S. For example, the user may grip the handle 304 and push distally on the shelf 388.

In some embodiments, the skin S provides relatively little resistance to passage of the needle 204 therethrough. That is, the needle 204 may be effective at penetrating the skin S. Accordingly, distal movement of the access assembly 109 and the driver 101 may be relatively unopposed or only negligibly opposed. Stated otherwise, distal movement of the drive shaft 320 may be substantially unopposed or may be slightly inhibited. The relatively small opposition may nevertheless slightly compress the compression spring 334, in some instances, although the relative movement between the drive shaft 320 and the housing 304 is insufficient to decouple the clutch 322 from the stop 324. Accordingly, the rotational orientation of the drive shaft 320 and the housing 304 may remain fixed during passage of the needle 204 through the skin S toward the bone B.

Figure 25B:
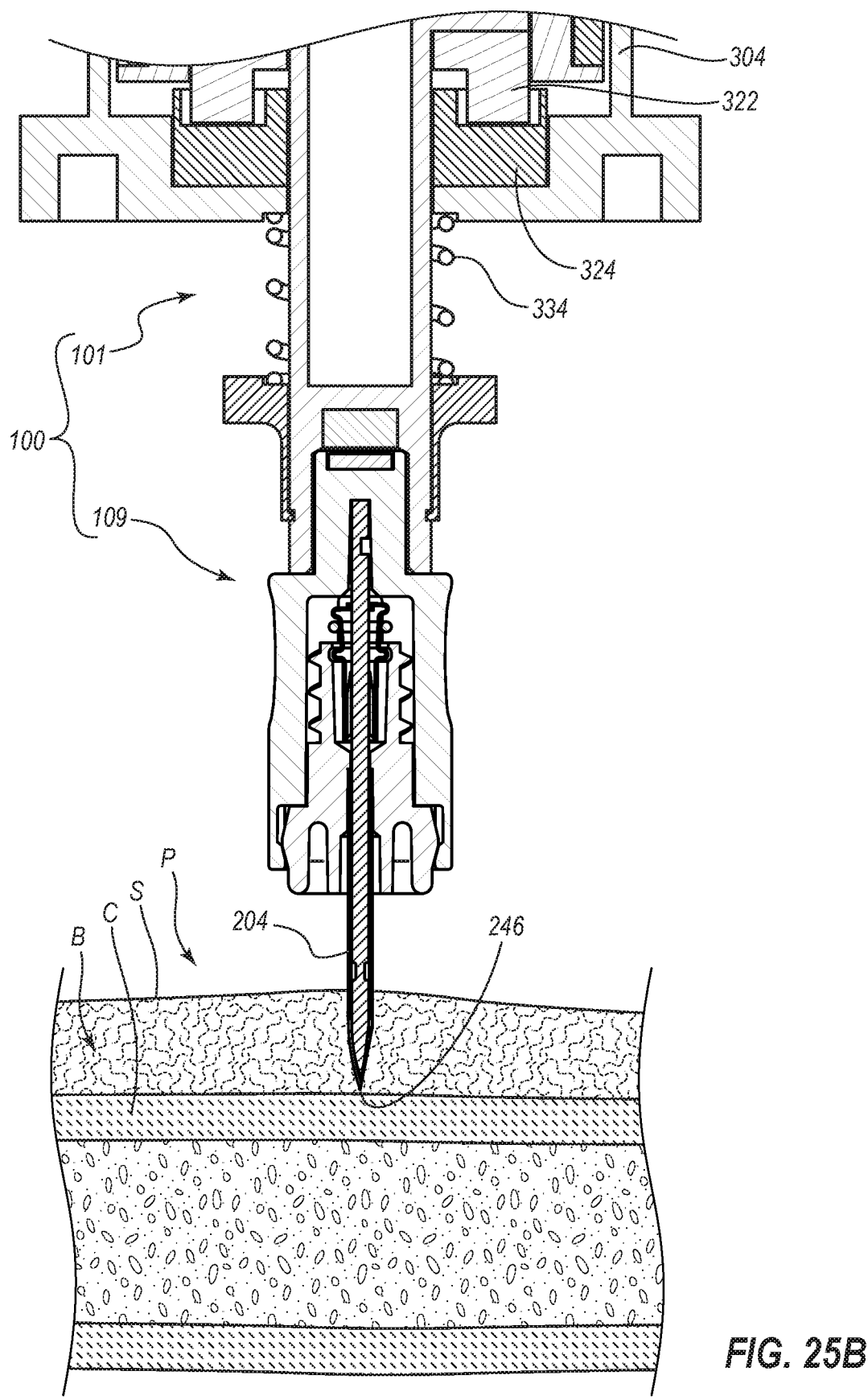
FIG. 25B depicts another stage of the illustrative method and is a cross-sectional view of the distal end of the driver and the access assembly after they have been used to pierce through skin of a patient to bring a distal tip of a cutting needle into contact with an external surface of a bone of the patient.
Figure 25C:
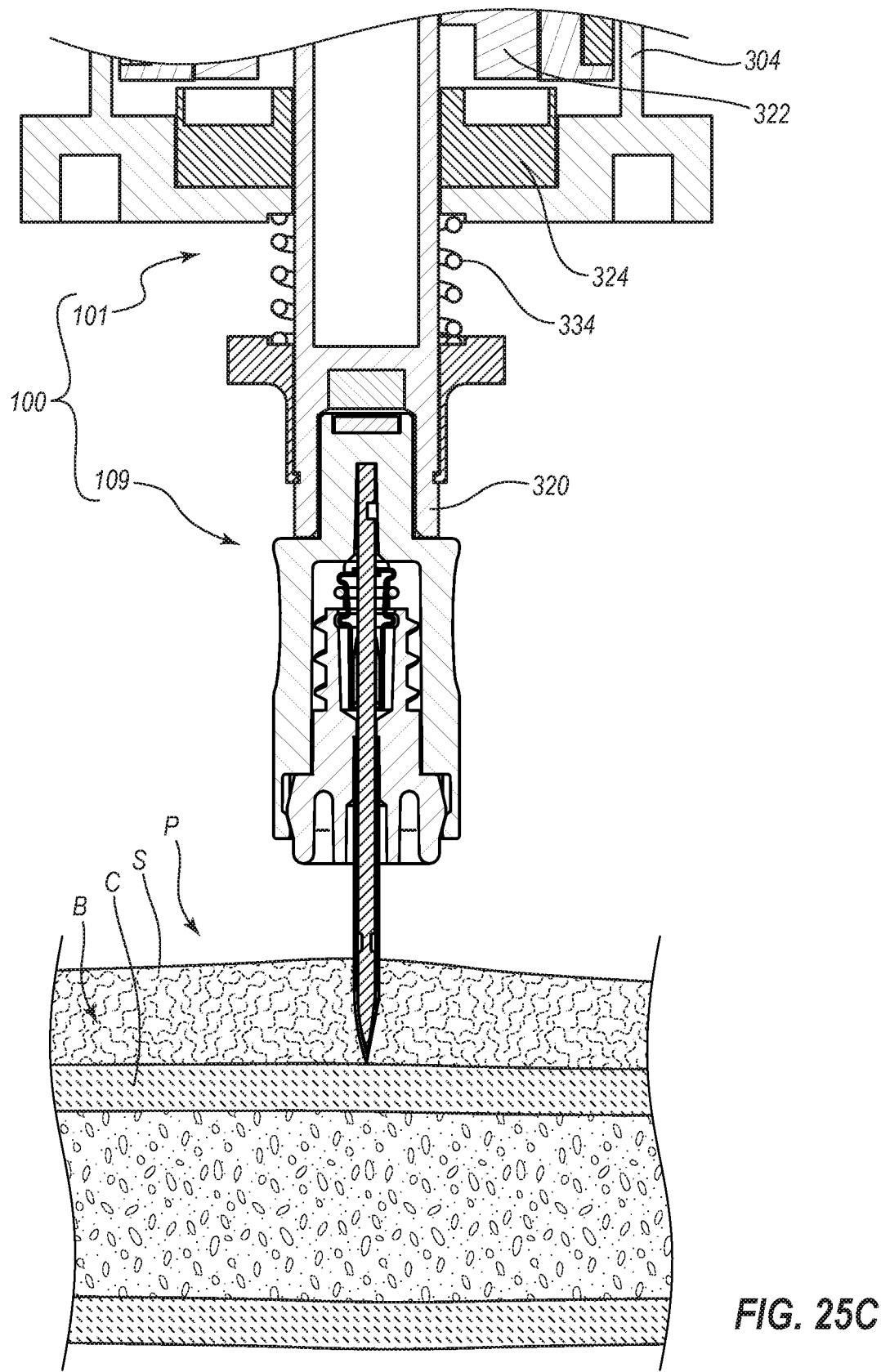
FIG. 25C depicts another stage of the illustrative method and is a cross-sectional view of the distal end of the driver and the access assembly showing the biasing member having been compressed by an amount sufficient to transition the drive shaft to a rotational state in which the drive shaft can rotate to drill the access assembly into the bone.

With reference to FIG. 25B, upon further distal advancement of the system 100, the distal tip 246 of the needle 204 may ultimately come into contact with an outer surface of the bone B, which may resist or oppose entry of the needle 204. A proximally directed reactive force of the bone B, or specifically, of a cortical layer C of the bone B, can increase with an increasing distally directed force on the handle 304. The distal force on the handle 304 and the resulting proximally directed force on the needle 204, which is transferred through the access system 109 to the drive shaft 320 of the driver 101, can continue to increase until the forces are sufficient to compress the compression spring 334 by an amount sufficient to decouple the clutch 322 from the stop 324.

In particular, as the compression spring 334 is compressed, the handle 304 moves distally relative to the drive shaft 320. As the handle 304 moves distally, the stop 324 that is fixedly coupled therewith also moves distally and away from the clutch 322, which is fixedly coupled with the drive shaft 320. Throughout this movement, the clutch 322 may be engaged with the stop 324 sufficiently to prevent rotation of the drive shaft 320 relative to the handle 304. The drive shaft 320 may be said to be in a rotationally restricted state. Once sufficient separation is achieved, as further discussed below, the drive shaft 320 is transitioned from the rotationally restricted state to a drilling state in which the drive shaft 320 is permitted to rotate relative to the handle 304 under the influence of the torsion spring 314 (FIG. 7). Stated otherwise, when in the drilling state, the drive shaft 320 is permitted to freely rotate, such as in the direction of rotational bias provided by the torsion spring 314.

With reference to FIGS. 6 and 7, as the handle 304 moves distally relative to the drive shaft 320, the handle 304 likewise moves distally relative to the housing 300. This is because the oppositional force imparted to the drive shaft 320 via the access assembly 109 is, in like manner, imparted from the drive shaft 320—specifically, from the clutch 322 of the drive shaft 320—to the partition 340 of the housing 300. In particular, a proximal face of the clutch 322 imparts the oppositional force to a distal face of the partition 340.

As the handle 304 moves distally relative to the housing 300, the slots 386 of the handle 304 move distally relative to the tabs 354 of the housing 300. Stated otherwise, the tabs 354 and the slots 386 translate relative to one another. The handle 304 may not be permitted to move distally relative to the housing 300 by an amount sufficient to fully displace the tabs 354 out of the slots 386. For example, the compression spring 334 may only permit a longitudinal displacement of the handle 304 relative to the drive shaft 320 by a predetermined distance, and this distance may be substantially less than the height H2 of the tab 354 (see FIG. 10) (or stated otherwise, substantially less than the height of the slot 386). Accordingly, the tabs 354 can remain within the slots 386 to prevent rotational movement of housing 300 relative to the handle 304.

The proximal cap 302 likewise may be rotationally fixed relative to the housing 300 throughout transition of the drive shaft 320 from the rotationally restricted state to the drilling state. In particular, as previously discussed, the inward bias provided by the torsion spring 314 can provide sufficient distal bias to the cap 302 to keep it in place, and the cooperating abutment surfaces of the housing 300 and the proximal cap 302 can prevent relative rotation of these components.

With reference to 25C, the outer surface of the cortical layer C of the bone B can continue to oppose distal movement of the drive shaft 320 as greater distal force is applied to the handle 304. Due to this oppositional force acting on the access assembly 109 and the drive shaft 320 coupled thereto, the handle 304 and the stop 324 can continue to move distally relative to the drive shaft 320 and associated clutch 322. When the stop 324 has been moved distally by a sufficient amount, the clutch 322 disengages from the stop 324, which permits the drive shaft 320 to spin under the influence of the torsion spring 314 (FIG. 7).

In arrangements such as just described, the torsion spring 314 can be actuated automatically. For example, rather than a user selectively actuating an actuator to initiate rotation of the drive shaft 320, the drive shaft 320 is automatically actuated once a sufficient force is applied to the driver 101—e.g., once a sufficient distally directed force is applied to the handle 304, where an opposition or reactive force in response to the applied force is proximally directed through or along the drive shaft 320. Stated otherwise, the driver 101 is configured to actuate automatically upon application of a minimum force or threshold drilling force thereto. The threshold drilling force may also be referred to as an actuation force, linear actuation force, or automatic actuation force of the driver 101.

In some embodiments, the compression spring 334 is preloaded such that it applies a distally directed "initial" force to the collar 330, and hence to the drive shaft 320. Likewise, the preloaded compression spring 334 applies a proximally directed "initial" force to the handle 304. For example, the compression spring 334 may be pre-compressed when the driver 101 is in a natural or undeployed state, such as depicted in FIG. 7. When the drive shaft 320, and hence the collar 330 presses proximally on the compression spring 334 by an amount greater than the "initial" force, the drive shaft 320 can begin to move proximally relative to the handle 304, depending on reference frame (e.g., in instances where distal movement of the handle 304 is opposed, or where the handle 304 is held steady). From a different reference frame, such as where it can be said that the drive shaft 320 is held steady, or where proximal movement of the drive shaft 320 is opposed, the handle 304 must press distally on the compression spring 334 by an amount greater than the "initial" force to move the handle 304 distally relative to the drive shaft 320.

With the application of a force slightly greater than the "initial" force, the drive shaft 320 will move proximally (or the handle 304 and stop 324 will move distally relative to the shaft 320) by an amount sufficient to disengage the clutch 322 from the stop 324, which automatically permits the discharge of the torsion spring 314 and associated rotation of the drive shaft 320. Thus, the "initial" force plus the additional force required to compress the spring 334 by an amount sufficient to disengage the clutch 322 from the clutch receiver 324 represents the minimum, threshold, or actuation force of the system.

In other embodiments, the compression spring 334 is not preloaded. For example, when the driver 101 is in an unactuated state, the compression spring 334 may be uncompressed, or in a natural, undeflected, or non-displaced state. The minimum, threshold, or actuation force of the system thus may correspond to the amount of force that is applied to the compression spring 334 to compress the spring 334 by an amount sufficient to disengage the clutch 322 from the clutch receiver 324. Stated otherwise, the compression spring 334 can provide a bias that must be overcome to transition the drive shaft 320 from the rotationally restricted state to the drilling state. The threshold force of the system corresponds to the force required to overcome this bias.

The minimum or threshold force can be selected to be sufficiently high to permit the driver 101 to urge the needle 204 through the skin of the patient and into contact with the bone without actuation (e.g., without disengaging the clutch 322). Further, the minimum or threshold force can be selected to require application of force to the bone in an amount sufficient to achieve efficient cutting of the bone via the needle 204. In various embodiments, the threshold force is about 20, 25, 30, 35, 40 or 45 newtons, is no less than about 20, 25, 30, 35, 40 or 45 newtons, or is no greater than about 20, 25, 30, 35, 40 or 45 newtons. In further embodiments, the threshold force is within a suitable closed range composed from the foregoing open-ended ranges. For example, in some embodiments, the threshold force is no less than about 20, 25, 30, 35, or 40 newtons and no greater than about 45 newtons, no less than about 20, 25, 30, or 35 newtons and no greater than about 40 newtons, etc.

At such forces, torque on the needle is within a range that achieves efficient cutting. In various embodiments, the torsion spring 314 can be preloaded with a torque of no less than about 100, 150, 200, 250, 300, 350, or 400 newton millimeters.

In certain embodiments, if the drilling force drops below the threshold force, the drilling automatically stops. In the illustrated embodiment, when the distally directed drilling force drops below the threshold force, the clutch 322 reengages the clutch receiver 322 and stops rotation of the drive shaft 320. This can, for example, prevent rapid spinning of the needle 204 that could overheat bone and surrounding tissue, to the discomfort of the patient.

In some embodiments, the compression spring 334 can inhibit application of excessive force to the drill 101 during a drilling event. This effect can be enhanced when the compression spring 334 has a relatively low spring constant, as this can facilitate maintaining a substantially constant force on the spring 334, due to the relationship:

$$F = -kx,$$

in which F is the force applied by the spring 334, k is the spring constant of the spring 172, and x is the displacement of the spring 334 from equilibrium (e.g., the displacement of the collar 330 and the handle 304 into either closer approximation to or greater spacing from each other, as compared with their relative positions when the spring is in an initial state). For example, for a given range of forces that might be desirable or acceptable to apply during a drilling event, a relatively high spring constant would permit only a narrow range of displacements of the collar 330 and the handle 304 relative to each other; a comparatively smaller spring constant would allow for a larger range of displacements. In some instances, this could advantageously make the system less sensitive to movement of the handle 304 relative to the drive shaft 320. In various embodiments, it can be desirable for the spring to have a maximum displacement when subjected to forces no greater than about 30, 35, 40, 45, or 50 newtons. Such forces may be considered the maximum recommended force for a given embodiment. In some instances, exceeding the maximum recommended force may, for example, cause the driver 101 to stall and/or suffer from other operational difficulties.

In some instances, it can be desirable for a user to slowly increase the amount of distal force applied to the handle 304 until the threshold or actuation force is reached and the driver 101 automatically actuates. Thereafter, it may further be advantageous for the user to continue applying approximately the same or slightly greater amount of force for a brief period over which drilling proceeds. A slow ramp up and/or substantially consistent application of force can reduce the likelihood of the user inadvertently exceeding the maximum recommended force. As previously discussed, in some embodiments, the compression spring 334 can beneficially regulate operation of the driver 101 within a range of forces that is bounded on one end by the actuation force and bounded on the other end by the maximum recommended force. Any suitable combination of the actuation and maximum recommended forces discussed above is contemplated.

The driver 101 can continue to drill so long as sufficient force is applied to the bone—and thus so long as the bone supplies sufficient reactive force—and also so long as the torsion spring 314 has sufficient energy to rotate the needle 204 to cut into the bone. As previously noted, if insufficient force is applied to the bone, the clutch 320 can reengage with the clutch receiver 322. The user then has the option to press harder on the bone to continue automated drilling, or to release the handle 304 and instead grip the housing 300 and/or the proximal cap 302 to continue drilling in a manual fashion, as discussed below. When the needle 204 stops spinning due to insufficient energy from the torsion spring 314, the user may permit the handle 304 to spring back, or proximally, relative to the housing 300 under the influence of the compression spring 334. The user can hold the housing 300 and/or the proximal cap 302 to continue drilling in a manual fashion, as discussed below.

The user also has the option of using the driver 101 in a manual fashion for an entirety of a drilling event, if so desired. For example, the user may use the driver 101 without charging and/or discharging the torsion spring 314. Stated otherwise, the driver 320 may remain rotationally fixed relative to the handle 304 throughout a manual drilling event.

To use the driver 101 in a manual mode, the user can grip the housing 300 directly and push distally while rotating the driver 101. The driver 101 can be rotated in either direction. In each direction, the tabs 354 interact with the slots 386 to ensure the handle 304 does not rotate relative to the housing 300. Moreover, the housing 300—or more particularly, the partition 340 of the housing 300—pushes on the clutch 320 sufficiently to maintain engagement between the clutch 320 and the clutch receiver 324. Accordingly, the drive shaft 320, the handle 304, and the housing 300 remain rotationally locked in either rotational direction when a user applies distally directed forces to the housing 300.

In like manner, the drive shaft 320, the handle 304, the housing 300, and the proximal cap 302 are rotationally locked when a user applies distally directed forces to the proximal cap 302. When the user pushes downward on the proximal cap 302 and rotates the driver 101 counterclockwise, the abutments 353, 368 engage.

When the user pushes downward on the proximal cap 302 and rotates the driver 101 clockwise, the camming surfaces 352, 366 engage each other. In the illustrated embodiment, the angle α defined by the camming surfaces 352 of the housing 300 (as well as the complementary camming surfaces 366 of the proximal cap 302) is relatively steep (see FIG. 10). Accordingly, the forces exerted by the camming surfaces 366 of the proximal cap 302 on the camming surfaces 352 of the housing 300 due solely to the clockwise twisting yield a significant downwardly (distally) directed component. This, in combination with downwardly directed forces applied to the proximal cap 302 can ensure that the proximal cap 302 remains rotationally locked relative to the housing 300. For example, when the angle α is 45 degrees or greater, the downward component of the twisting force when combined with the direct downward force will always overpower any component of the twisting force that would tend to rotate the proximal cap 302 relative to the housing 300.

Figure 25D:
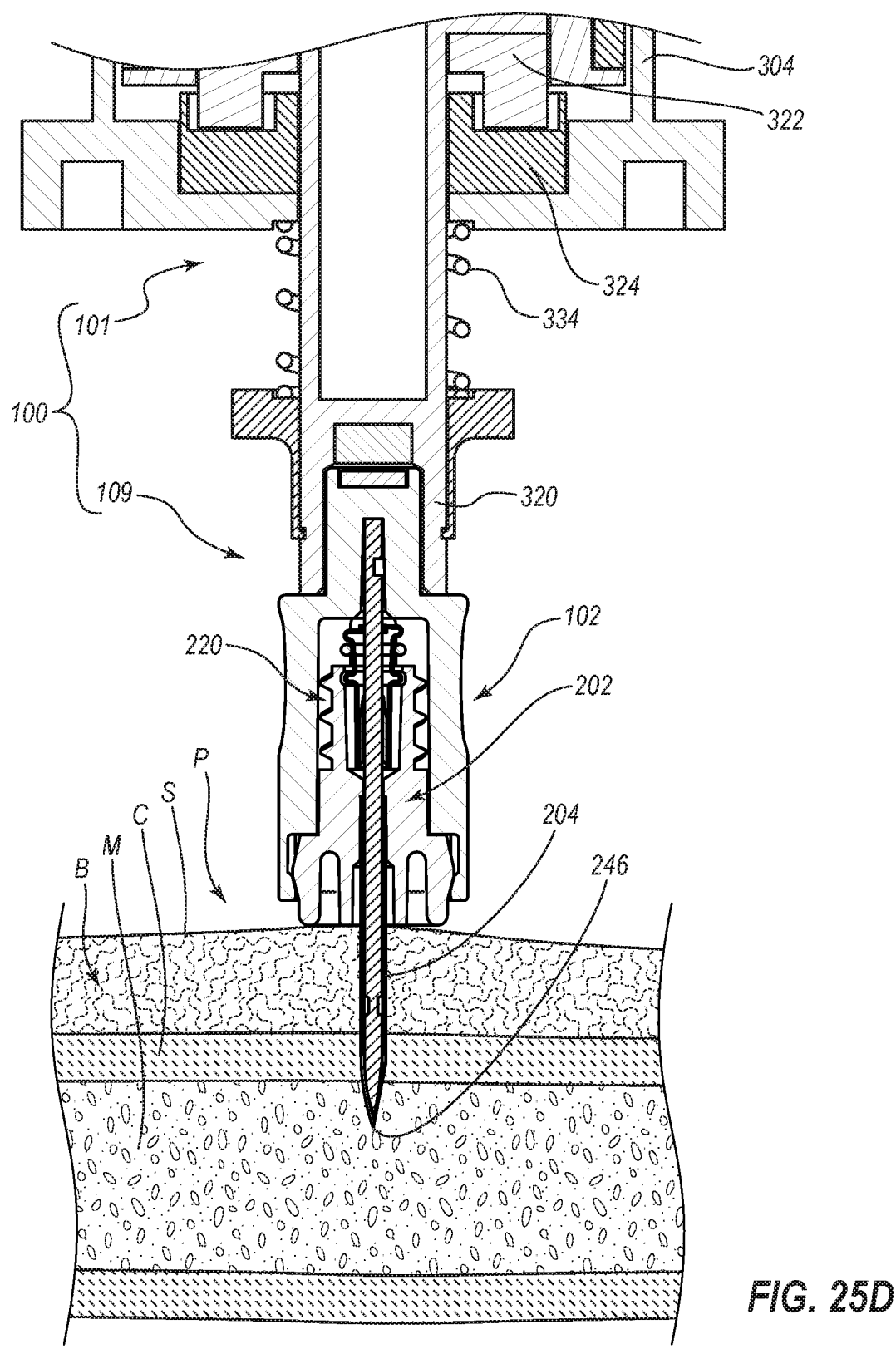
FIG. 25D depicts another stage of the illustrative method and is a cross-sectional view of the distal end of the driver and the access assembly after they have been used to provide access to an interior of the bone of the patient.

FIG. 25D depicts a method stage at which the needle 204 has been drilled past the cortical layer C and into the marrow M of the bone B and rotation of the needle 204 has stopped. As the distal tip 246 and distal end of the needle 204 pass through the hard, cortical layer C, the resistive or reactive force provided by the bone B in opposition to the drilling is reduced due to the softer structure of the marrow M. In some instances, this change in resistance can provide a tactile feedback to the user, alerting the user that a desired amount of drilling has been achieved. The user thus may voluntarily reduce or eliminate the amount of distally directed force applied on the handle 304. As smaller forces are applied in opposite directions on the handle 304 and the drive shaft 320, the compression spring 334 may decompress or otherwise return toward its starting position, thus bringing the clutch 322 and the stop 334 back into engagement to rotationally lock the drive shaft 320 relative to the housing 304. In other or further instances, the reduction in opposing, resistive, or reactive force supplied by the bone B upon transition from the cortical layer C to the marrow M may be sufficient on its own to bring the clutch 322 and the stop 334 back into engagement and automatically stop rotation of the drive shaft 320.

In some embodiments, the driver 101 can operate at relatively high rotation speeds. The speeds can far exceed speeds that are achievable by manual manipulation alone. In some instances, the rate of speed may have little effect on the overall ease by which the access system 109 is introduced into the bone B, yet it may be advantageous to operate at relatively high speeds to ensure a rapid discharge of the torsion spring 314. Such a rapid discharge can reduce the likelihood of inadvertently drilling too far, such as by drilling through the backside of the bone B (e.g., the back end of the cortical layer C). It takes some amount of time for the needle 204 to proceed through the cortex layer C, all the way through the marrow M, and then reach the cortex layer C again at the back side of the bone B. In some instances, the driver 101 can discharge all of the stored energy of the torsion spring 314 in fractions of a second, such that there is insufficient time for the needle 204 to reach the back side of the bone B while stored energy remains in the spring 314.

Once the access assembly 109 has been introduced into the bone B, such as shown in FIG. 25D, the driver 101 may be removed from the access assembly 109. The obturator assembly 102 may then be removed from the needle assembly 202 in manners such as previously described. Any suitable medical device (syringe, extension set, etc.) may then be coupled with the connector for subsequent infusion and/or aspiration.

Any suitable variation of the foregoing embodiments is contemplated. For example, as discussed above, the illustrated driver 101 is configured to be wound in one-half turn increments, which is achieved by the two identical housing components 308a, 308b and the two arms 362, 364 of the proximal cap 302 that interact with the same. Other arrangements are also possible. For example, in other embodiments, three identical housing components are used (e.g., each may form one third of the circumference of the housing), and the proximal cap 302 includes three identical arms to interact with the same. This can result in a driver 101 that can be wound in one-third turn increments. Other or further arrangements are contemplated, such as those that utilize other numbers or arrangements of housing components and corresponding arms of the proximal cap 302.

As another example, any suitable configuration for preventing rotational movement between the handle 304 and the housing 300 is contemplated. For example, in some embodiments, the handle 304 defines a tab and the housing 300 defines a slot into which the tab is received. Stated otherwise, the tab and slot arrangement of the illustrated embodiments may be reversed.

As yet another example, the proximal cap 302 and/or the handle 304 can be lengthened and the thickened region 350 (see FIG. 10) can be shortened. For example, in some instances, a user may grip one or more of the proximal cap 302 or the handle 304 during different stages of using the driver 101, with any gripping of the thickened region 350 being incidental or ancillary. For example, during winding of the driver 101, a user may grip the proximal cap 302 with one hand and the handle 304 (at least primarily) with the other. During automated drilling into bone, the user may grip (at least primarily) the distal cap 302. During manual drilling into bone, the user may grip (at least primarily) the proximal handle 304.

Figure 26:
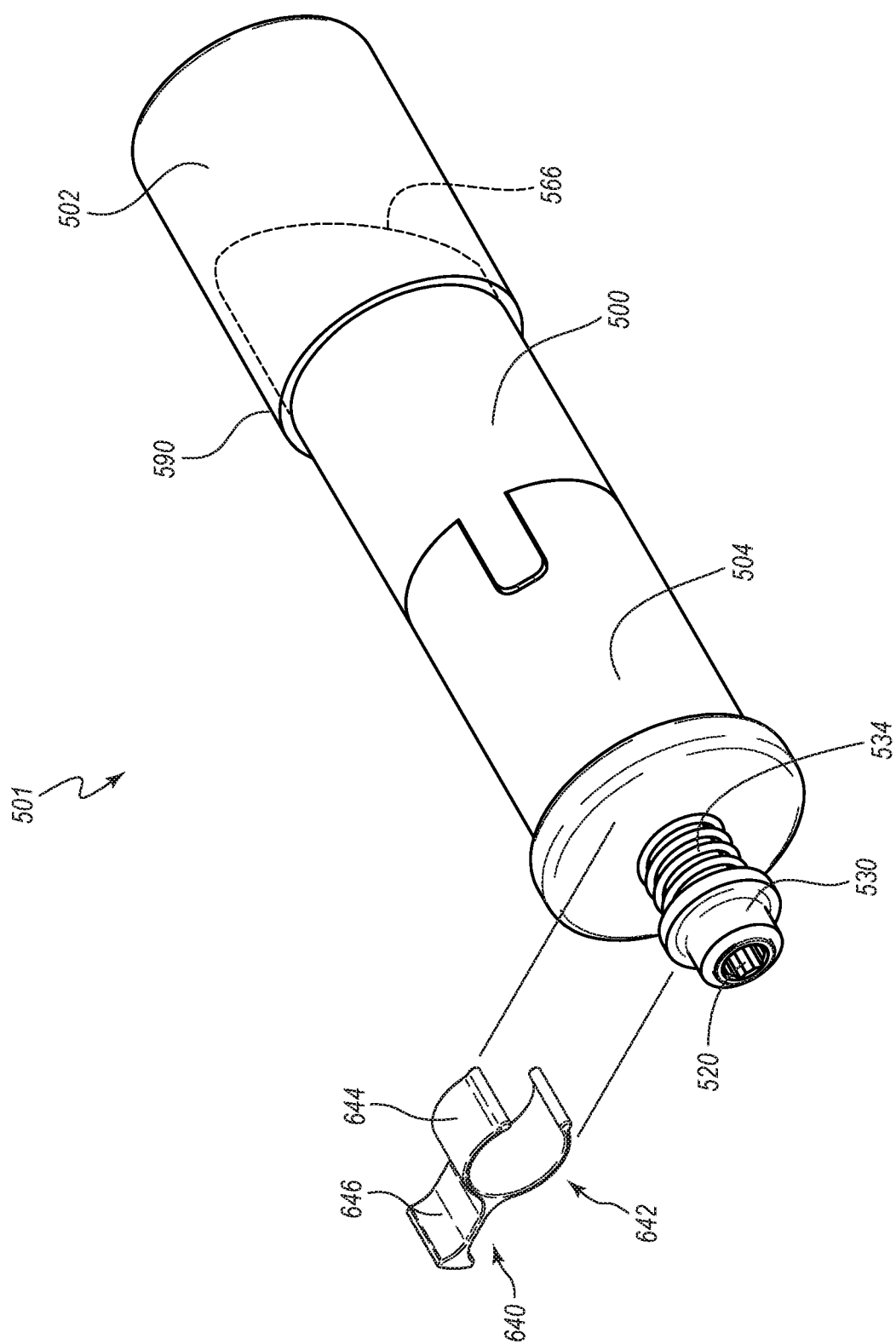
FIG. 26 is a perspective view of another embodiment of a driver that can be used, for example, with an access assembly for penetrating into a bone.
Figure 27:
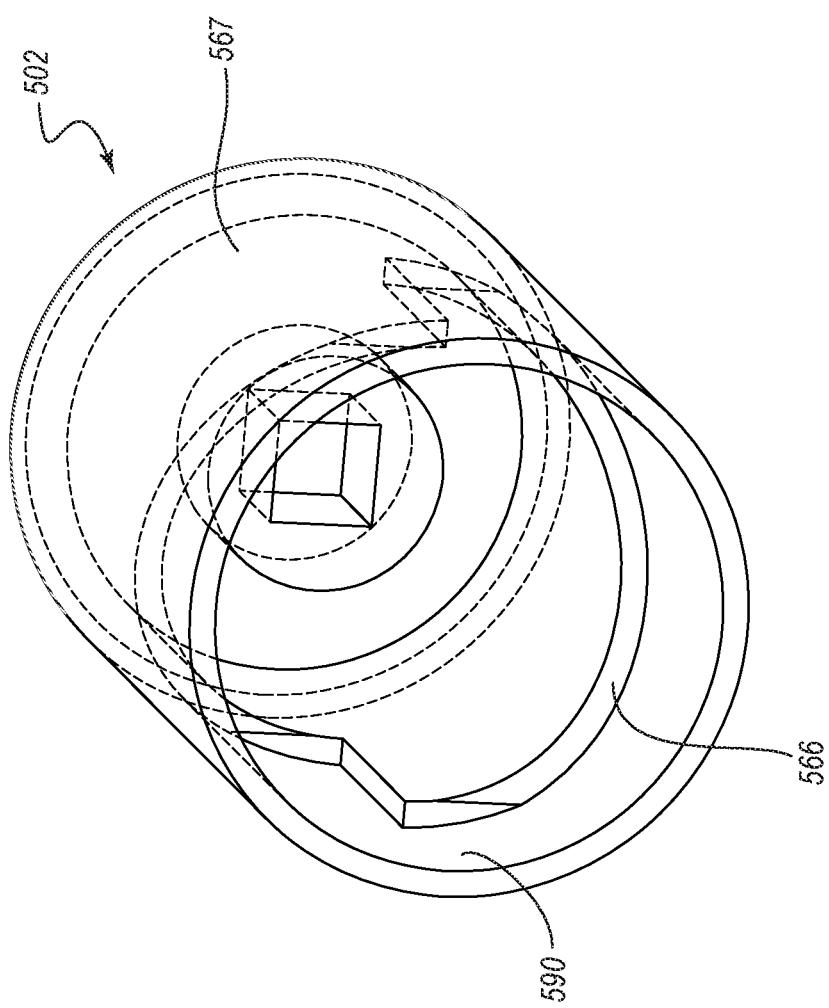
FIG. 27 is a bottom perspective view of a proximal cap portion of the driver of FIG. 26.

FIG. 26 depicts another embodiment of a driver 501 that resembles the driver 101 in many respects. Accordingly, like features are generally, although not necessarily exclusively, designated with like reference numerals, with the leading digits incremented either from "3" to "5" or from "4" to "6." Relevant disclosure set forth above regarding similar features (e.g., features identified by similarly reference numerals) thus may not be repeated hereafter. Moreover, specific features of the driver 501 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the driver 501. Any suitable combination of the features and variations of the same described with respect to the driver 101 can be employed with the driver 501, and vice versa. Further, the driver 501 may suitably be used in place of the driver 101 in the system 100. Stated otherwise, the access assembly 109 may be used with embodiments of the driver 501 in manners, methods, and procedures such as previously described. This pattern of disclosure applies equally to further embodiments depicted in subsequent figures and described hereafter, wherein the leading digits may be further incremented In the illustrated embodiment, the driver 501 includes a proximal cap 502 that sheaths a proximal end of a housing 500. As shown in FIG. 27, the proximal cap 502 includes a thicker sidewall 567 that defines a skirt 590 that encompasses a distal end of the housing 500. The proximal cap 502 can include an internal ramp 566 that resembles the ramps 366 discussed above with respect to the proximal cap 302.

With continued reference to FIG. 26, in some embodiments, the driver 501 includes a removable retainer 640 that may prevent inadvertent discharge or actuation of the driver 501. The retainer 640 can be coupled to the driver 501 about at least a portion of a compression spring 534. The retainer 640 can maintain a spacing between a collar 530 and a handle 504. Stated otherwise, the retainer 640 can prevent relative longitudinal movement between a drive shaft 520 and the handle 504, which might otherwise disengage a clutch (such as the clutch 322 described above) and actuate the driver 501 in manners such as previously discussed.

In certain illustrative reusable embodiments, the retainer 640 may be coupled to the driver 501 after a user has wound the driver 501 to ensure the driver 501 is ready for use at a later time. In certain illustrative single-use embodiments, the retainer 640 may be secured to the driver 501 at some point prior to packaging and/or shipping to ensure the single-use device is not prematurely actuated, such as during transport and/or unpackaging. A user may remove the retainer 640 prior to using the driver 501 for an access event.

In the illustrated embodiment, the retainer 640 includes a clip 642 configured to snap over at least a portion of the compression spring 534. In the illustrated embodiment, the clip 642 comprises a pair of opposing resilient arms 644. The retainer 640 can further include a grip or stem 646 to facilitate handling of the retainer 640.

Figure 28:
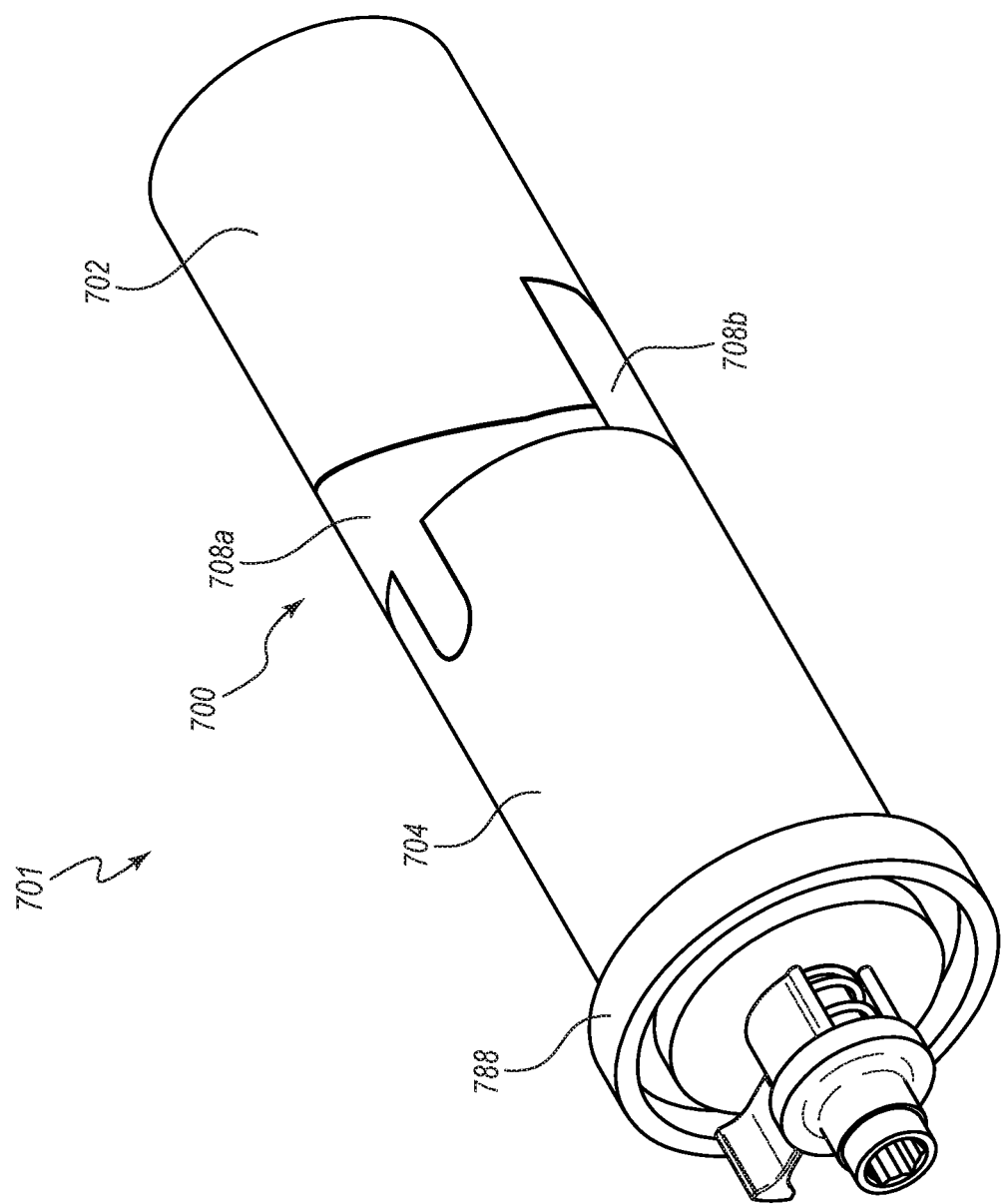
FIG. 28 is a perspective view of another embodiment of a driver that can be used, for example, with an access assembly to drill into a bone.

FIG. 28 depicts another embodiment of a driver 701 that resembles the drivers 101, 501 in many respects. Like these other drivers, the driver 701 includes a housing 700, a proximal or winding cap 702, and a distal cap or handle 704. The housing 700 may also or alternatively be referred to as a body, a shaft, a stem, an intermediate structure, a hub, a base, a translational/rotational base, a core, etc.

As compared with the drivers 101, 501, the proximal cap 702 and the distal cap 704 of the driver 701 are relatively longer. Likewise, the portion of the housing 700 that is externally exposed is relatively shorter. Indeed little more than the portions of the housing 700 that define camming and abutment surfaces and rotationally locking tabs, such as those previously described, are exposed at the external surface of the driver 701. In some instances, this arrangement can be advantageous, as illustrative methods of using the driver 701 may proceed by solely or primarily gripping the handle 704 and/or the winding cap 702. Stated otherwise, in some instances, all stages of using the driver 701 may proceed without any need to hold the exposed surface of the housing 700.

In the illustrated embodiment, the housing 700 is formed of two housing components 708a, 708b, in manners such as previously discussed. In other embodiments, the housing 700 may be formed of a single unitary component.

Figure 29:
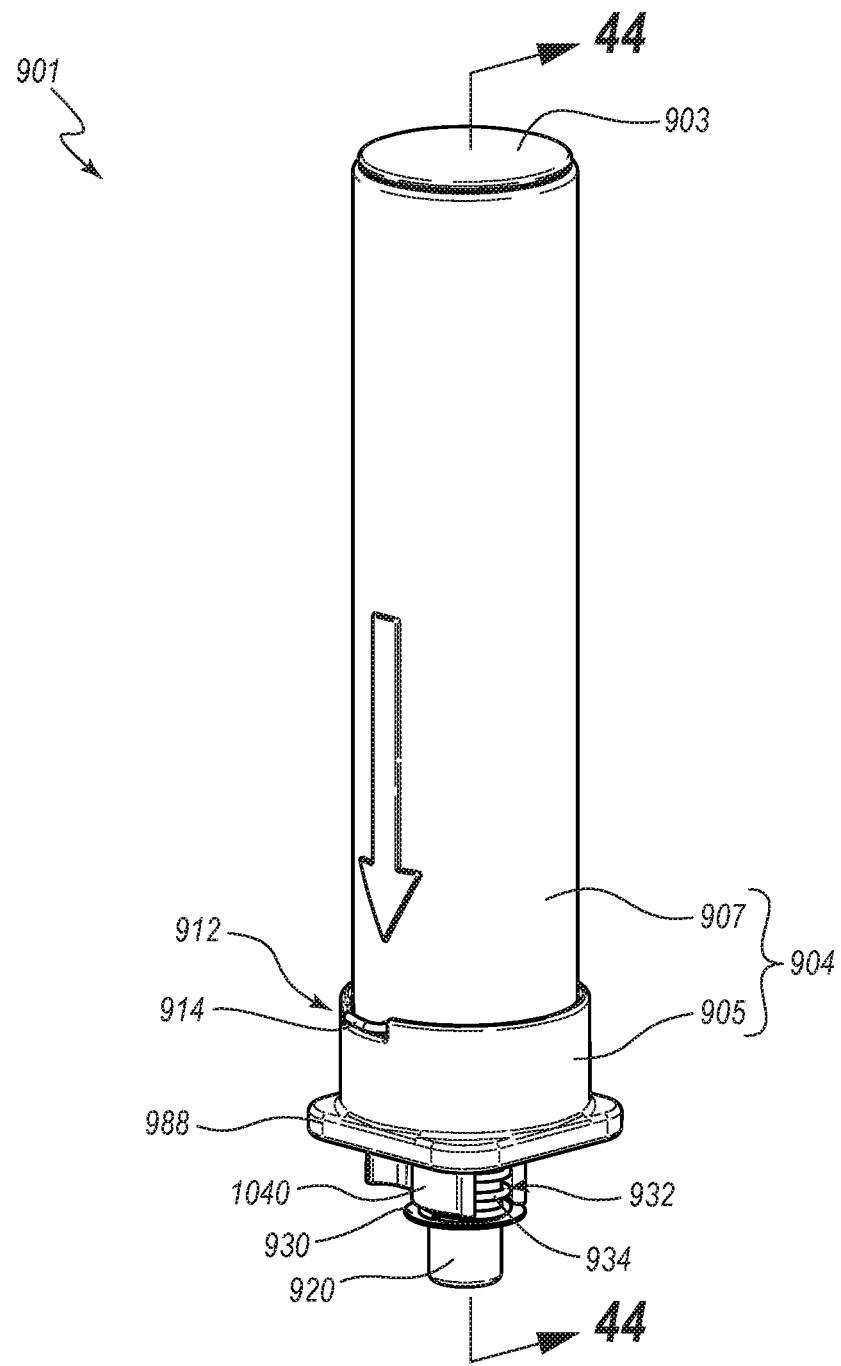
FIG. 29 is a perspective view of another embodiment of a driver that can be used, for example, with an access assembly to drill into a bone.

FIG. 29 depicts another embodiment of a driver 901 that resembles the drivers 101, 501, 701 in many respects. The driver 901, however, does not include housings or winding caps of the varieties previously discussed. Rather, the driver 901 includes a handle 904, which can be elongated relative to certain embodiments previously disclosed, and a drive shaft 920 that extends through a distal end of the handle 904 and that is coupled to a proximal cap or cover 903, which is positioned at a proximal end of the drive shaft 920. In the illustrated embodiment, a rotational biasing member 912 (e.g., a torsion spring 914), of which only a distal tip is visible in FIG. 29 (see FIGS. 37 and 44), is coupled with the handle 904 and the drive shaft 920, as discussed further below. The illustrated driver 901 further includes a collar 930, a longitudinal biasing member 932 (e.g., a compression spring 934), and a retainer 1040, which closely resemble similar features previously described.

With continued reference to FIG. 29, the handle 904 can include a distal cap 905 fixedly secured to an elongated shaft, tube, housing, or body 907. Accordingly, in the illustrated embodiment, the handle 904 is of a two-part construction. Any other suitable arrangement is contemplated. For example, in other embodiments, the handle 904 may be a single, monolithic, unitary component that defines the various features of the distal cap 905 and the body 907. In the illustrated embodiment, the distal end of the torsion spring 914 is captured between the distal cap 905 and the body 907, and is thereby fixedly secured to the handle 904. Any other suitable mechanism for fixedly securing the torsion spring 914 to the handle 904 is contemplated.

Figure 30:
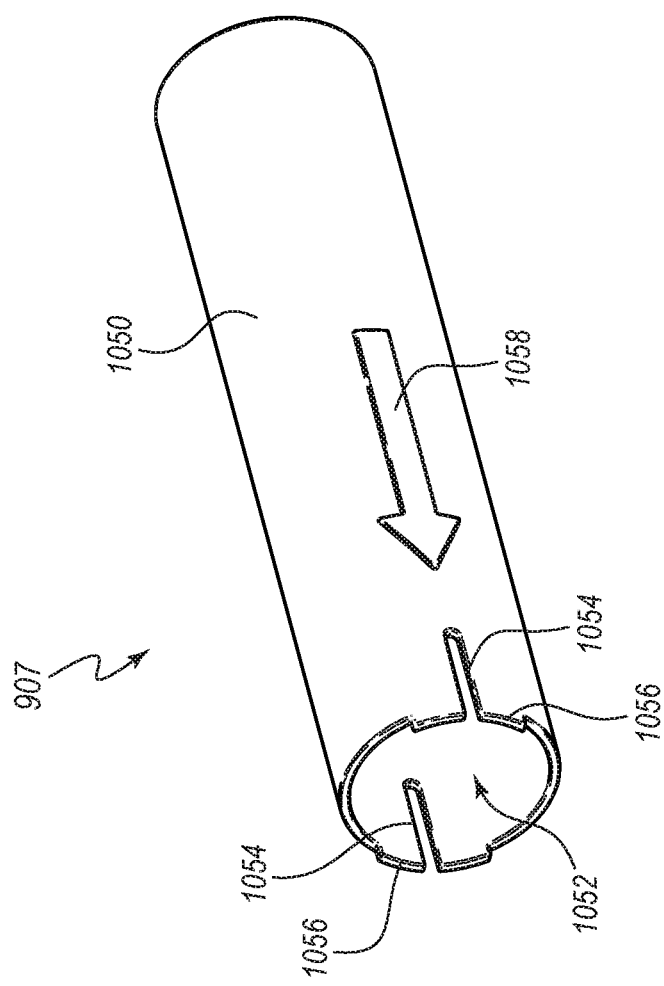
FIG. 30 is a perspective view of an embodiment of a handle compatible with the driver of FIG. 29.

With reference to FIG. 30, in the illustrated embodiment, the body 907 is formed as a substantially cylindrical tube 1050. The tube 1050 defines a lumen or cavity 1052 into which various components of the driver 901 are received. A distal end of the tube 1050 defines a pair of slots 1054 and a plurality of tabs 1056. Either slot 1054 may optionally be used to receive the distal end of the torsion spring 914 therein during manufacture of the driver 901.

In some embodiments, indicia 1058 of any suitable variety may be provided on the tube 1050. In the illustrated embodiment a pair (only one is visible) of diametrically opposed arrows point in the distal direction. The arrows can indicate to a user that the body 907 is to be gripped and urged distally to actuate the driver 901.

Figure 32:
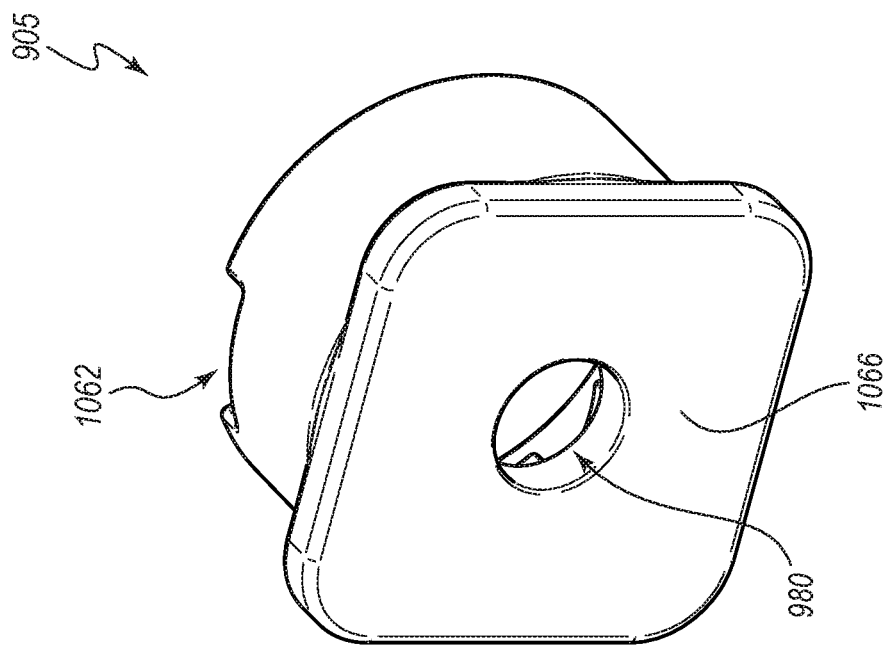
FIG. 32 is a lower perspective view of the distal cap.
Figure 31:
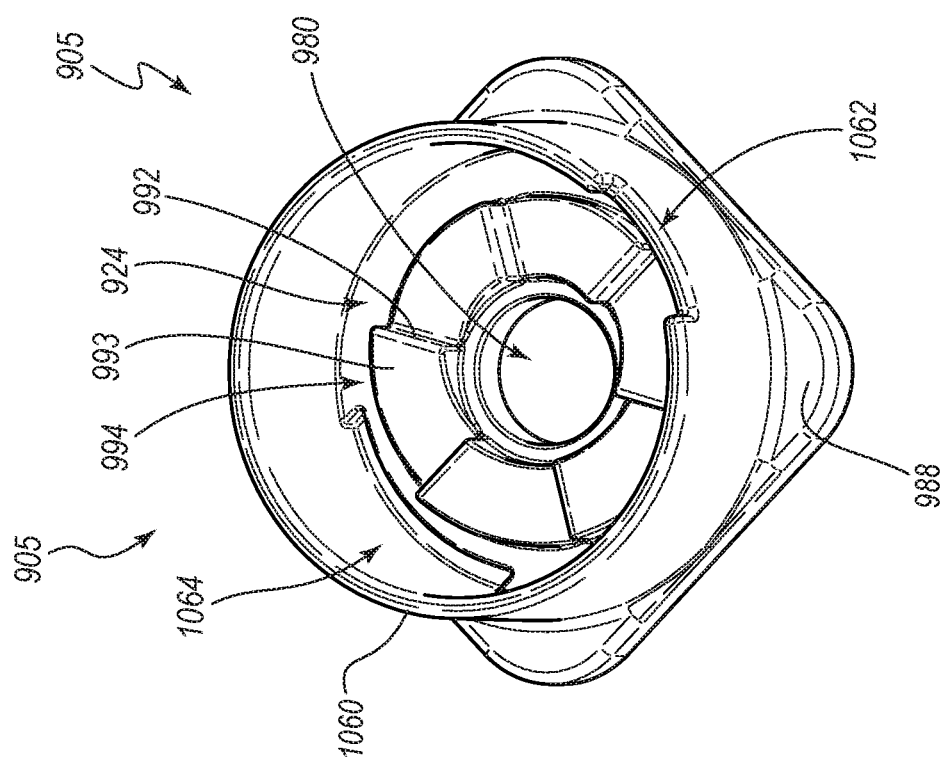
FIG. 31 is an upper perspective view of an embodiment of a distal cap compatible with the driver of FIG. 29.
Figure 34:
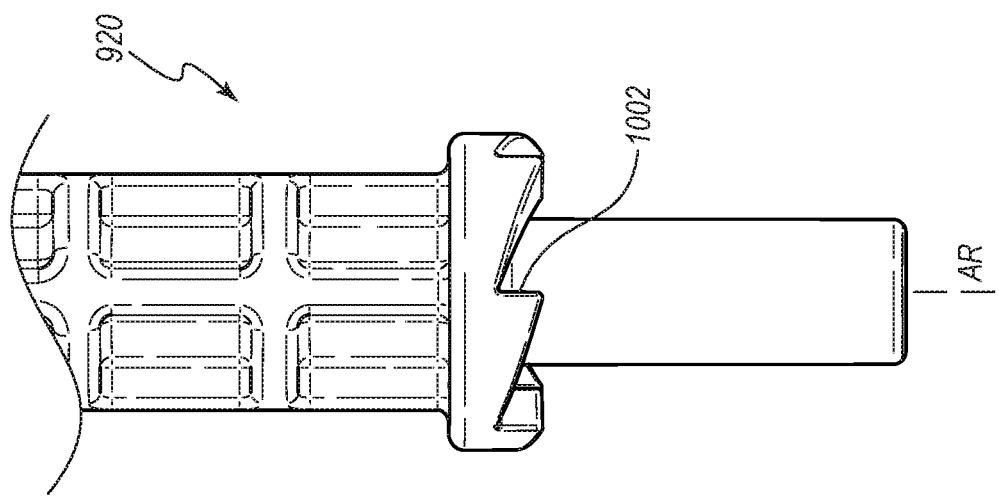
FIG. 34 is an elevation view of a distal portion of the drive shaft.
Figure 33:
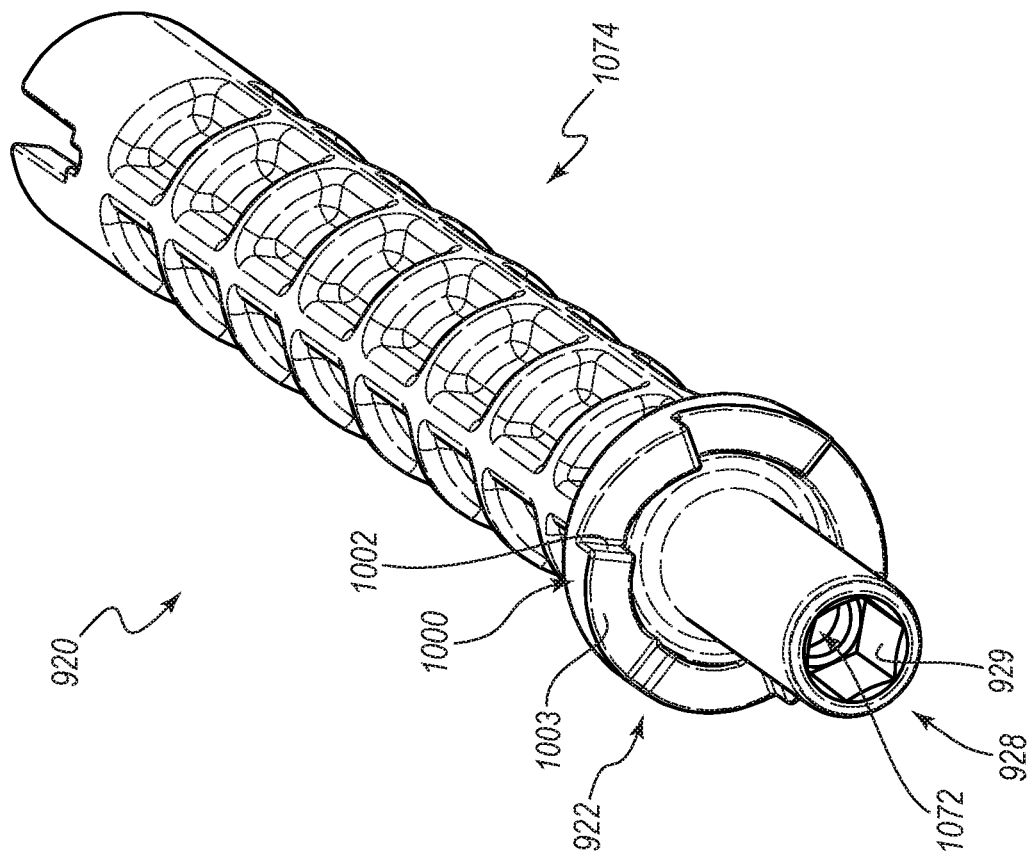
FIG. 33 is a lower perspective view of an embodiment of a drive shaft compatible with the driver of FIG. 29.

With reference to FIGS. 31 and 32, the distal cap 905 can resemble the distal cap 304 in many respects, with features of the stop 324 incorporated therein. The distal cap 304 can define a drive shaft opening 980 and a stop 924 similar to previously described features. The stop 924 can include a plurality of proximally extending teeth 994, each of which includes a stopping surface 992 and a ramp 993. These features can function in manners such as previously described.

The distal cap 905 can further include a protrusion or shelf 988. In some instances, a user may choose to apply distal force to the shelf 988 to assist in actuating the driver 901. In the illustrated embodiment, the shelf 988 defines a substantially square perimeter or profile. The shelf 988 thus may prevent inadvertent rolling of the driver 901 when the driver is set on its side. Any other suitable profile or other configuration of the shelf 988 is contemplated.

The distal cap 905 can include a shroud, skirt, or sleeve 1060 that extends proximally from the shelf 988. The sleeve 1060 may be sized to fit tightly over the tube 1050. In some embodiments, the sleeve 1060 defines a notch or recess 1062 to accommodate the distal end of the torsion spring 914. In other embodiments, the recess 1062 may be omitted. For example, in some embodiments, the distal cap 905 may be fixedly secured to the distal end of the torsion spring 914 in any suitable manner, and the sleeve 1060 may cover the distal end of the torsion spring 914.

As shown in FIG. 31, the distal cap 905 can include a pair (only one is visible) of diametrically opposed recesses 1064 into which the tabs 1056 of the tube 1050 can be received. In some embodiments, cooperation of the recesses 1064 and the tabs 1056 can enhance rotational locking of the distal cap 905 and the tube 1050.

As shown in FIG. 32, in the illustrated embodiment, the distal cap 905 includes a distal face 1066 that is substantially planar. As with other embodiments, the compression spring 934 can press against the distal face 1066.

With reference to FIGS. 33-36, the drive shaft 920 can resemble the drive shaft 320 discussed above in many respects. For example, the drive shaft 920 can include a distal protrusion or coupling interface 928 such as the coupling interface 328 discussed above. The coupling interface 928 can include a longitudinally extending shaft that defines a cylindrical outer face. The coupling interface 928 includes an internal socket 929. At the base of the socket is a recess 1072, which can receive a magnetic member therein for enhanced coupling with an access assembly, as previously described.

Further, the drive shaft 920 can include an integrally formed clutch 922, which extends transversely from an upper end of the coupling interface 928. The clutch 922 can include a plurality of distally extending teeth 1000. In the illustrated embodiment, each tooth 1000 includes a stopping surface 1002 and a ramp 1003. These features can function in manners such as previously described. For example, in the illustrated embodiment, each of the stopping surfaces 1002 is substantially vertical relative to an axis of rotation AR of the drive shaft 920. Stated otherwise, planes defined by each stopping surface 1002 can intersect along the rotational axis AR or can extend parallel to the rotational axis AR.

Figure 44:
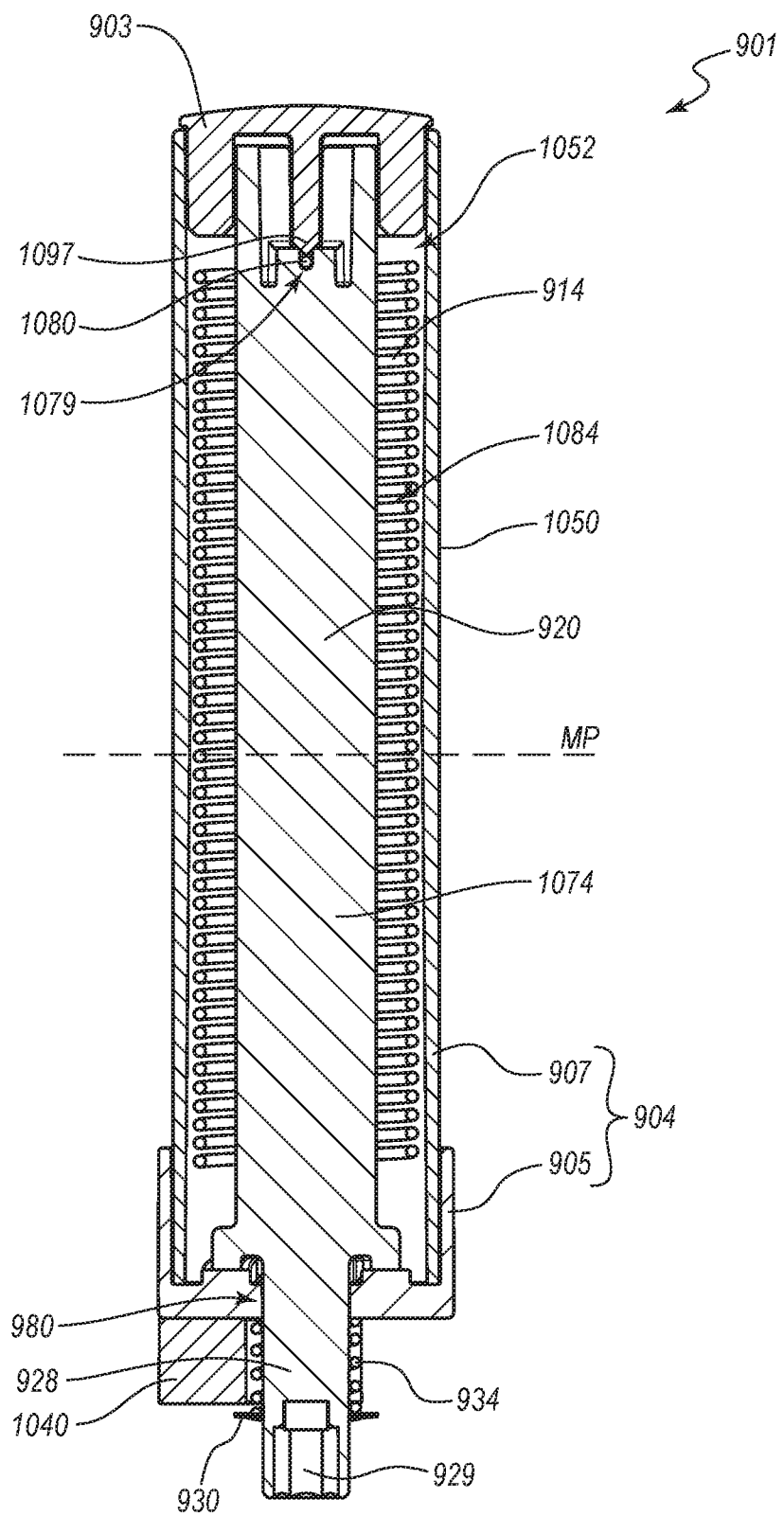
FIG. 44 is a cross-sectional view of the assembled driver of FIG. 29 taken along the view line 44-44 in FIG. 29.

The drive shaft 920 can include an elongated body 1074 that is substantially larger than a similar feature of the drive shaft 320. As shown in FIG. 44, the body 1074 can be nearly as long as the body 907 portion of the handle 904 in the illustrated embodiment. Other relative lengths are contemplated. Moreover, the drive shaft 920 is longer than the handle 904, in the illustrated embodiment. Other relative lengths are contemplated.

With continued reference to FIGS. 33-36, the body 1074 can include a waffle pattern, which may assist in the manufacturing process (e.g., when the drive shaft 920 is formed as a molded component), and may include a plurality of longitudinal and lateral ribs. The body 1074 can have a relatively large mass, and or a relatively large rotational inertia. In some instances, increasing the rotational inertia of the drive shaft 920 can assist in stabilizing the driver 901 during use.

Figure 36:
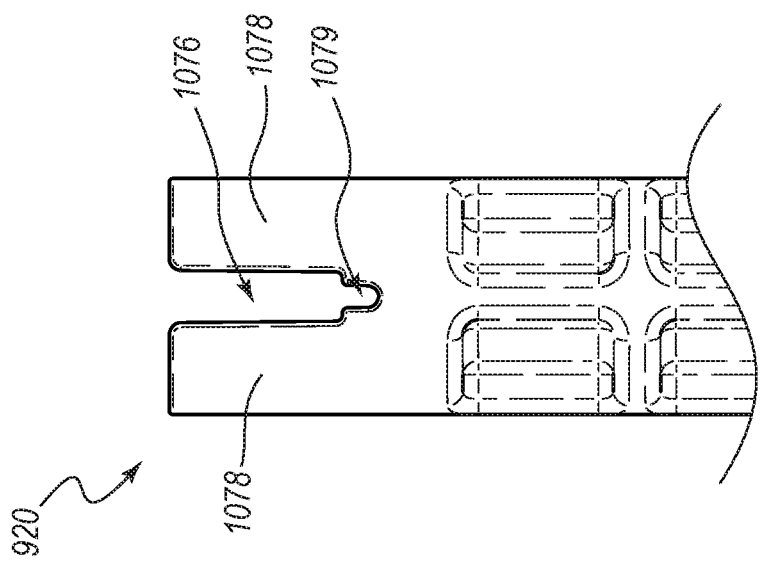
FIG. 36 is an elevation view of a proximal portion of the drive shaft.
Figure 35:
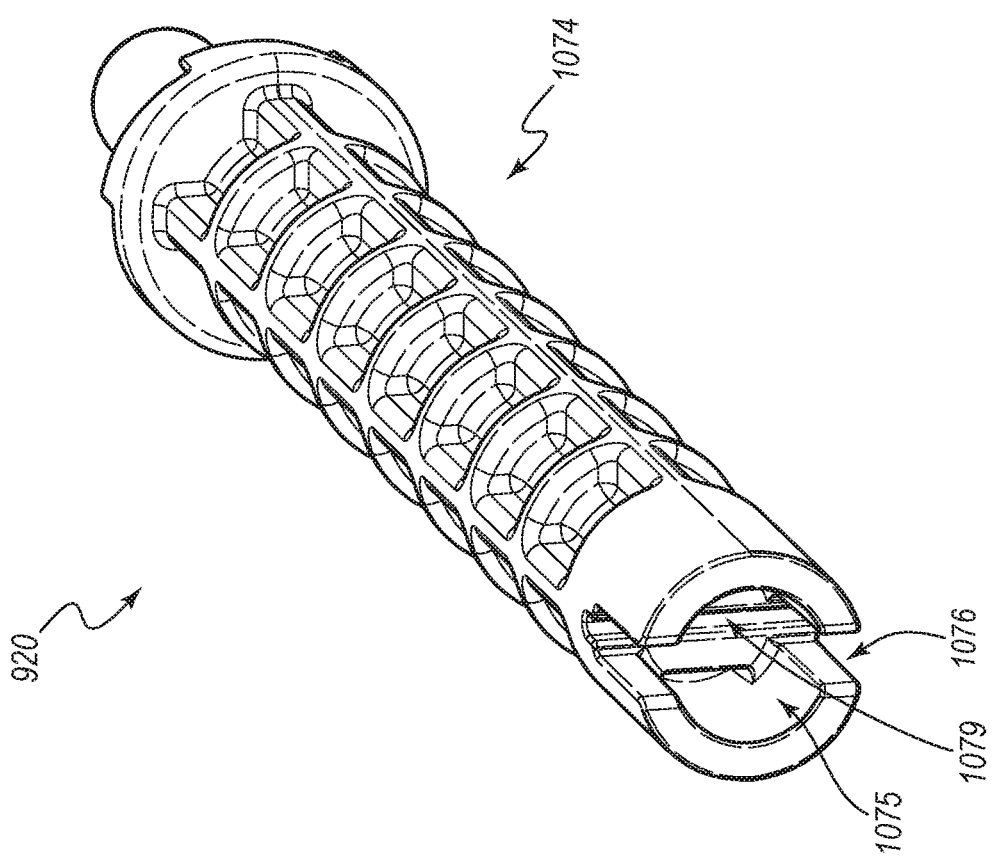
FIG. 35 is an upper perspective view of the drive shaft.

The torsion spring 914 can be fixedly secured to the drive shaft 920 in any suitable manner. With reference to FIGS. 35 and 36, the illustrated drive shaft 920 can include a coupling configuration for receiving and connecting to a proximal end of the torsion spring 914. In particular, the drive shaft 920 includes a spring channel 1079 into which a laterally extending proximal end of the torsion spring 914 can be received. The drive shaft 920 further defines a proximal chamber 1075 and a pair of diametrically opposed slots 1076 into which a portion of the proximal cap or cover 903 can be received. The proximal end of the torsion spring 914 thus may be trapped between the cover 903 and the drive shaft 920. Two semi-cylindrical protrusion 1078 can border the slots 1076.

Figure 37:
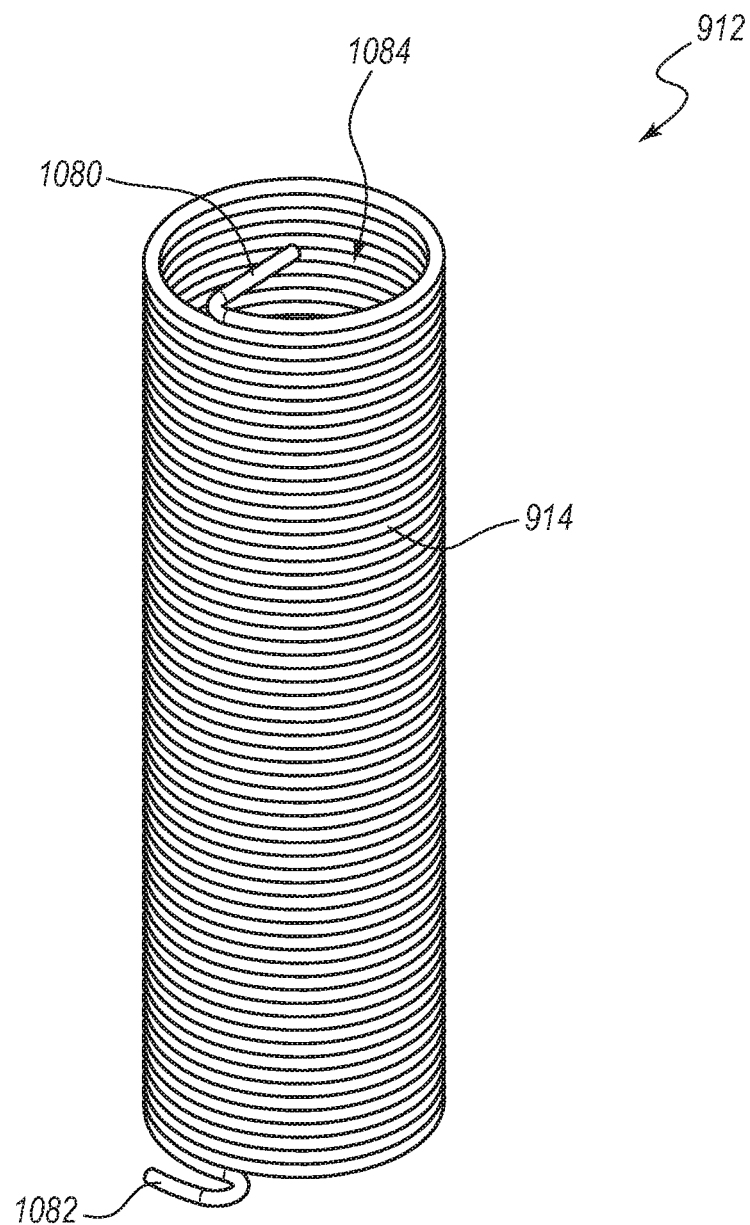
FIG. 37 is a perspective view of an embodiment of a torsion spring compatible with the driver of FIG. 29.

With reference to FIG. 37, the torsion spring 914 can include a plurality of coils that define a cylindrical region, which can generally define a cavity 1084. The proximal end of the spring 914 can include an inwardly extending transverse end 1080 that fits inside the spring channel 1079 of the drive shaft 920, as previously noted. The distal end of the spring 914 can include an outwardly extending transverse end 1082 that can be captured between the distal cap 905 and the body 907 to be fixedly secured with the handle 904, as previously noted.

Figure 39:
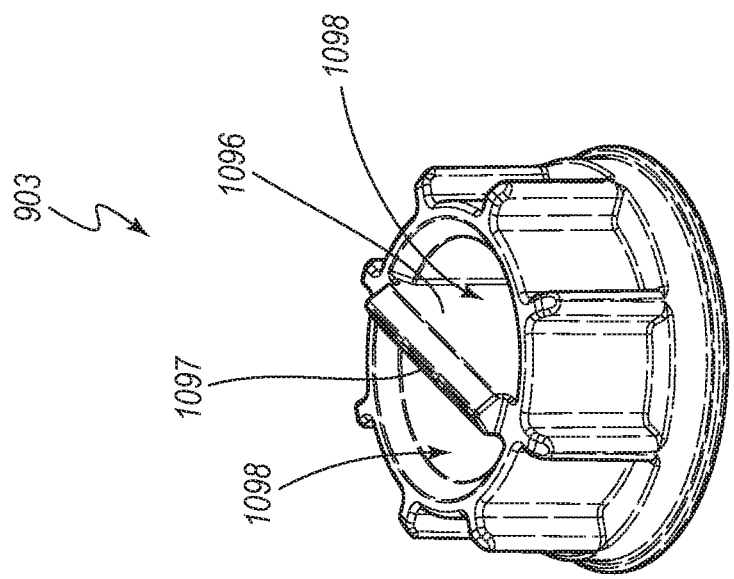
FIG. 39 is a lower perspective view of the proximal cap.
Figure 38:
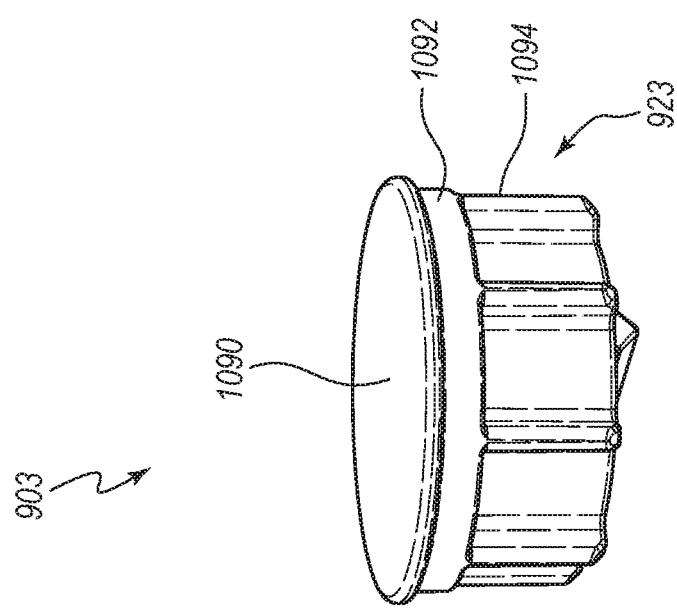
FIG. 38 is an upper perspective view of an embodiment of a proximal cap compatible with the driver of FIG. 29.

With reference to FIGS. 38 and 39, the cover 903 can include a proximal surface 1090 that can be readily pressed by the hand of a user, such as when the driver is used in a manual (rather than automated or powered) mode. The surface 1090 may be spread out laterally to increase comfort (e.g., by distributing forces to reduce pressure).

The cover 903 can further include a bearing 923. The cover 903 may also or alternatively be referred to as a bearing. The bearing 923 may comprise an outer surface for bearing against and/or spinning within the body 907 of the handle 904. In the illustrated embodiment the bearing 923 includes an outer surface of each of a plurality of longitudinally extending ribs 1094. The ribs 1094 can reduce the total surface area of the bearing 923 that contacts the inner surface of the handle 904, thus reducing friction.

Figure 45:
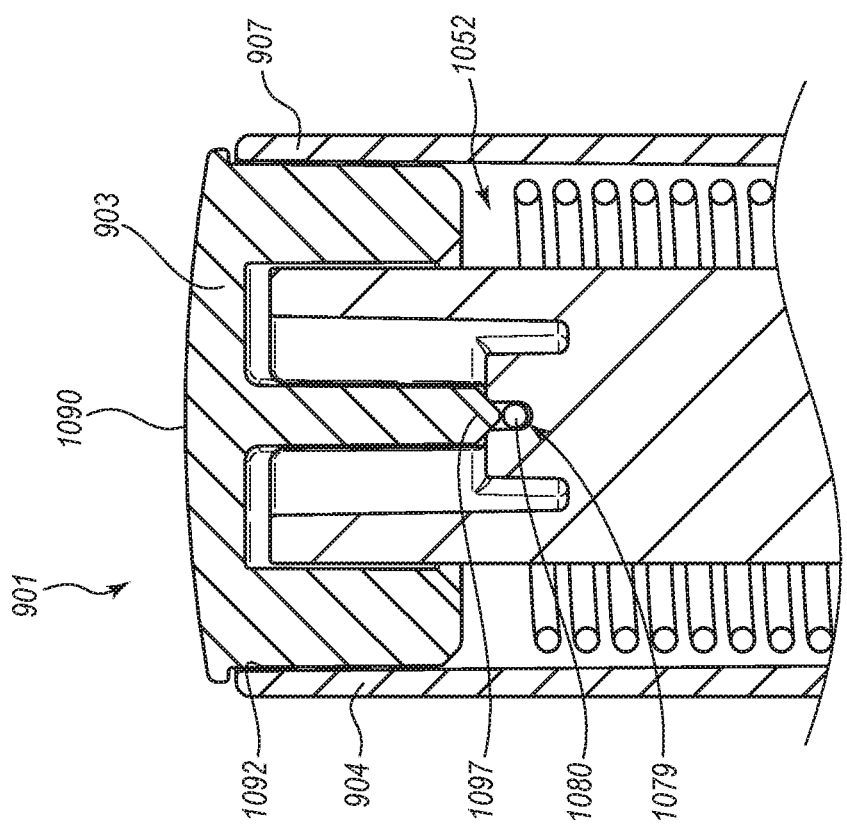
FIG. 45 is an enlarged cross-sectional view, similar to that of FIG. 44, of a proximal end of the driver showing the driver in an early stage of use.

The cover 903 may further include an upper rim or band 1092 that is a substantially solid cylindrical surface. In some embodiments, the band 1092 can engage (e.g., lightly contact) the inner surface of the body 907 of the handle 904 when the drive shaft 920 is in a rotationally restricted state of operation (e.g., when the driver 901 is unactuated), as shown in FIG. 45. In some embodiments, the band 1092 may close the upper end of the cavity 1052.

With reference to FIG. 39, the cover 903 can include a rotation lock or insert 1096 configured to sit within the slots 1076 of the drive shaft 920 and maintain a fixed angular relationship between the cover 903. An angled wedge or protrusion 1097 can extend distally from the insert 1096 to wedge the proximal end 1080 of the torsion spring 914 within the spring channel 1079, or otherwise hold the proximal end 1080 in place, as shown in FIGS. 44 and 45. The cover 903 can further define a pair of cavities 1098 for receiving the protrusions 1078 at the proximal end of the drive shaft 920.

The cover 903 can be attached to the drive shaft 920 in any suitable manner. In some embodiment, the attachment may be by frictional engagement. In other or further embodiments, attachment mechanisms such as adhesives, solvent bonding, and/or ultrasonic welding may be used.

In the illustrated embodiment, the cover 903 and the drive shaft 920 are separate components that are joined together. In other embodiments, the cover 903 and the drive shaft 920 may be unitarily formed together. For example, in some embodiments, the drive shaft 920 may include a proximal end that defines some or all of the features of the cover 903.

Figure 42:
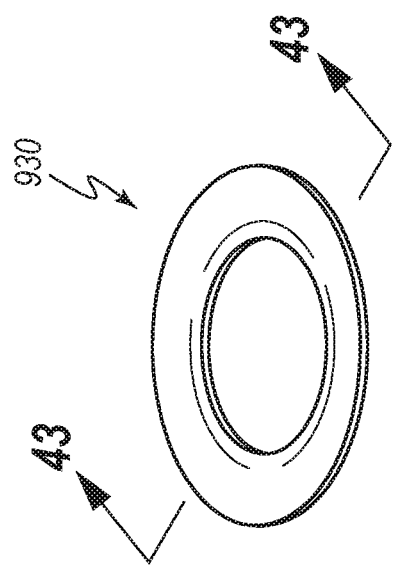
FIG. 42 is a perspective view of an embodiment of a collar compatible with the driver of FIG. 29.
Figure 43:
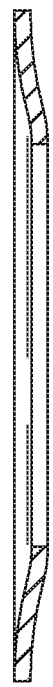
FIG. 43 is a cross-sectional view of the collar taken along the view line 43-43 in FIG. 42.
Figure 41:
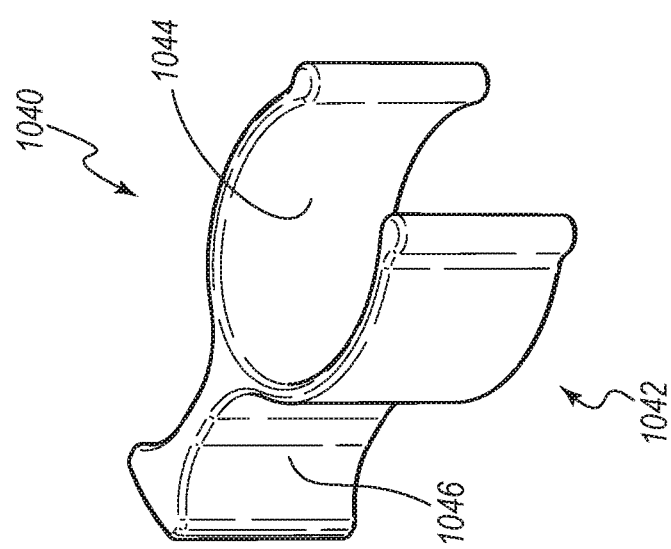
FIG. 41 is a perspective view of an embodiment of a retainer compatible with the driver of FIG. 29.
Figure 40:
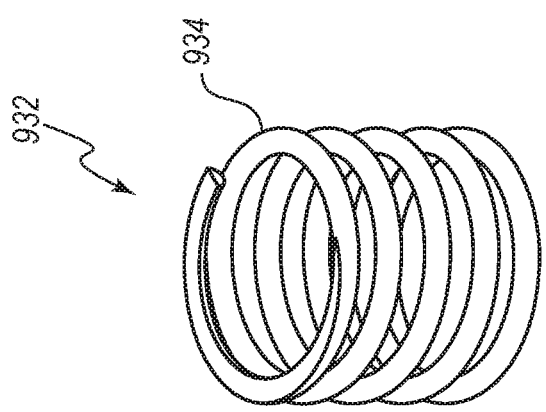
FIG. 40 is a perspective view of an embodiment of a compression spring compatible with the driver of FIG. 29.
Figure 48:
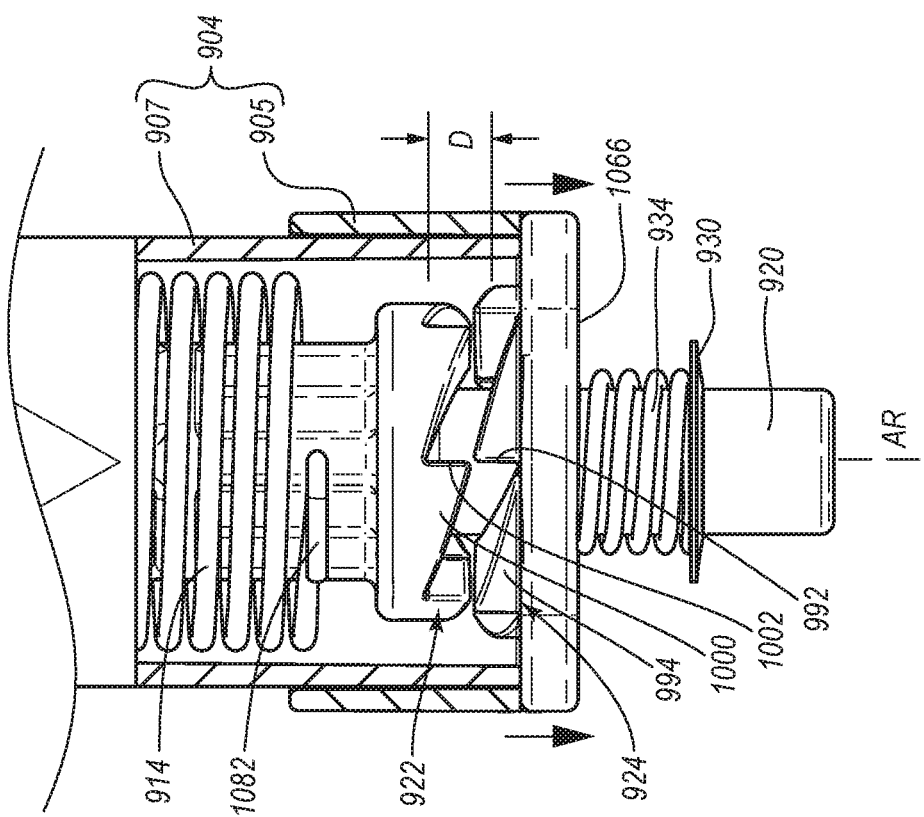
FIG. 48 is another cutaway elevation view of the distal end of the driver while the driver is in the same later stage of use depicted in FIG. 47.

With reference to FIGS. 40-43, the biasing member 932, the retainer 1040, and the collar 930 can resemble previously discussed components. In the illustrated embodiment, the biasing member 932 includes a flattened proximal end and a flattened distal end (see FIG. 46). The retainer 1040 can include a clip 1042, resilient arms 1044, and a handle or grip 1046, such as discussed with respect to earlier embodiments. As shown in FIGS. 42 and 43, the collar 930 can be an angled washer configured to grip into a sidewall of the drive shaft 920. Application of a distally directed force against the collar 930, as shown in FIG. 48, can cause the collar 930 to grip the shaft 920 tighter. Any other suitable arrangement is contemplated.

With reference to FIG. 44, when the driver 901 is in an assembled state, the drive shaft 920 extends longitudinally through an entirety of the cavity 1084 defined by the torsion spring 914. Positioning the drive shaft 920 within the spring 914 can, in some instances, advantageously achieve a relatively compact design.

In the illustrated embodiment, a proximal end of the drive shaft 920 is positioned proximal to a medial plane MP that extends transversely through a longitudinal or rotational axis of the driver 901. In contrast, a proximal end of the drive shaft 320 discussed above is distal to a medial plane that extends transversely through the longitudinal or rotational axis of the driver 101.

FIG. 44 depicts the driver 901 in an early stage of use. As with other embodiments discussed herein the driver 901 may be provided in a pre-wound or pre-loaded state. In other or further embodiments, an end user may wind the driver 901, such as by using a hex key in manners such as previously discussed. In the case of such end-user winding, the user can hold onto the handle 904 with one hand and rotate a hex key that has been coupled to the socket of the drive shaft 920 in a clockwise direction (as viewed from above). The clutch 922 and the stop 924 can act as a ratchet, incrementally retaining increased amounts of angular deflection of the torsion spring 914. During such winding, the interacting ramps of the clutch 922 and stop 924 gradually raise the drive shaft 920 and the cover 903 relative to the handle 904 (e.g., move them proximally relative to the handle 904) until the end of the ramps are reached and the stopping surfaces align or angularly move past one another. This movement can compress the compression spring 934, thus increasing the bias provided thereby. When the stopping surfaces align or angularly move past one another, the compression spring 934 can act on the drive shaft 920 and cover 903 to cause these components to drop relative to the handle 904 (e.g., move distally relative to the handle 904). The cover drive shaft 920 and the cover 903 thus can sequentially bounce or raise and lower relative to the handle 904 during an energy storage event. In some embodiments, the retainer 1040 is removed prior to winding the torsion spring 1084 to permit relative movement of the drive shaft 1020 and the handle 1040.

In certain embodiments, the end user can remove the driver 901 from the packaging. The user can subsequently remove the retainer 1040 to permit relative movement of the drive shaft 1020 and the handle 1040. In some embodiments, the driver 901 is provided in a pre-loaded state. In other embodiments (e.g., certain reusable embodiments), the end user winds the driver 901.

At any suitable time, an access assembly, such as the access assembly 109, can be coupled to the socket 929 of the drive shaft 920. The user may grip the handle 904 and urge the system into a bone and subsequently infuse and/or aspirate in manners such as previously disclosed.

Figure 46:
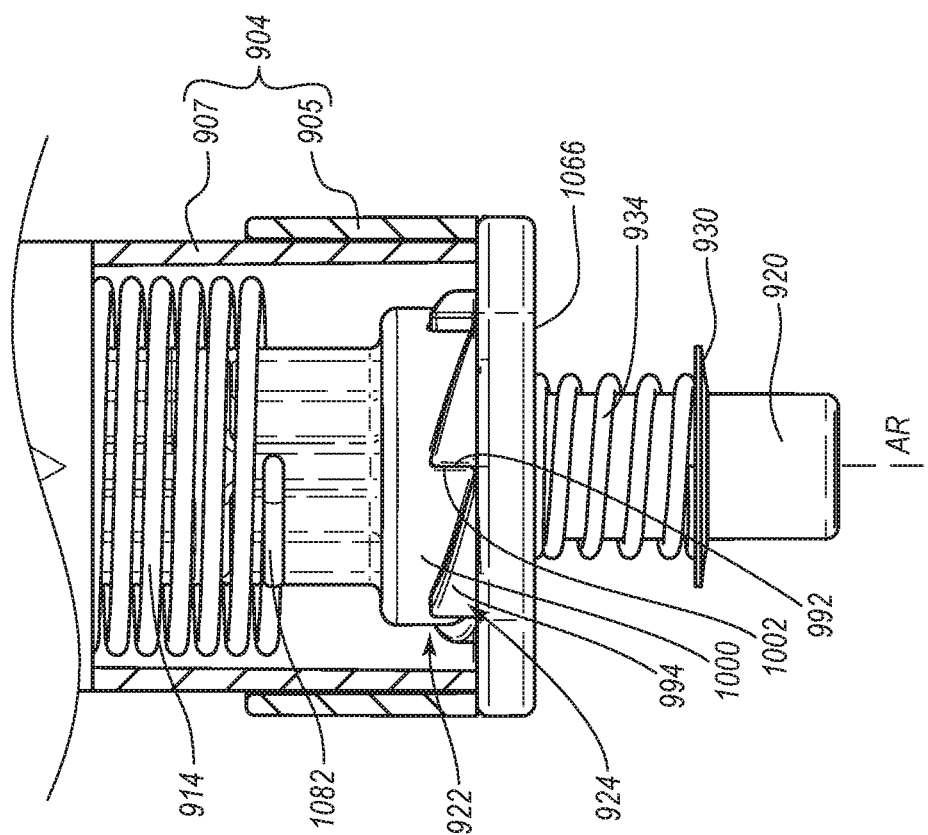
FIG. 46 is a cutaway elevation view of a distal end of the driver while the driver is in the same early stage of use depicted in FIG. 45.

FIGS. 45 and 46 depict a point in time during such an illustrative process in which the driver 901 has not yet been actuated so as to permit the torsion spring 914 to unwind. This stage is similar to that depicted in FIG. 25B, in which the needle 204 has first been brought into contact with an exterior surface of the bone.

In this state, the stopping surfaces 992, 1002 of the stop 924 and the clutch 922, respectively, abut one another so as to oppose the rotational bias provided by the charged torsion spring 914. In the illustrated embodiment, the stopping surfaces 992, 1002 are substantially vertical, and thus are aligned with or are parallel to the rotational axis of the drive shaft 920. In such circumstances, the stopping surfaces 992, 1002 can slide longitudinally past each other without causing the drive shaft 920 and the handle 904 to rotate relative to one another. Stated otherwise, a distally directed force can be applied to the handle 904, which force can be opposed by the bone to yield a proximally directed force on the drive shaft 920. As the handle 904 moves distally under the distal force and the drive shaft 920 remains in place, the stopping surface 992 can translate or slide downward relative to the stopping surface 1002. The stopping surfaces 992, 1002 continue to oppose the rotational bias of the torsion spring 914 without causing any relative rotation until the stopping surfaces 992, 1002 are decoupled from each other.

The drive shaft 920 is thus maintained in a rotationally restricted state. The non-rotation just described is a special case of a rotationally restricted state in which no rotation is achieved. In other embodiments, some rotation may be permitted while the drive shaft 920 is in a rotationally restricted state. For example, in other embodiments, the stopping surfaces 992, 1002 may be oriented at an angle relative to the rotational axis AR, which can yield a limited amount of rotation of the drive shaft 920 as it is transitioned from the rotationally restricted state to a drilling state.

Figure 47:
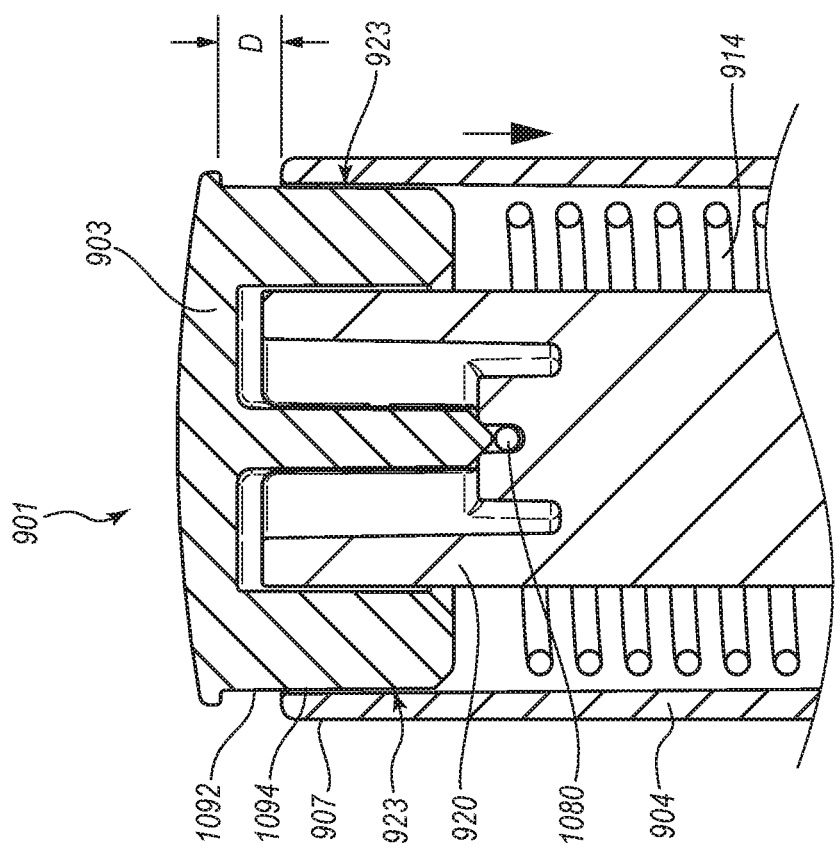
FIG. 47 is another cross-sectional view of the proximal end of the driver, such as the view of FIG. 45, with the driver shown in a later stage of use.

FIGS. 47 and 48 depict a stage at which the stopping surfaces 992, 1002 have been decoupled, such that the drive shaft 920 has been transitioned to the drilling state. In the illustrated embodiment, a proximal end of the drive shaft 920 is moved from a position in which it is encompassed by the body 907 of the handle 904 (as shown in FIG. 45) when in the rotationally restricted state to a position in which it is located proximally past a proximal end of the body 907 of the handle 904 in the drilling state. In other embodiments, the proximal end of the drive shaft 920 may remain encompassed by the handle 904.

With reference to FIGS. 45 and 47, relative movement of the handle 904 and the drive shaft 920 by a displacement distance D in transitioning from the unactuated to actuated states of the driver 901 can raise the band 1092 of the cover 903 out of contact with the handle 904. This can leave only the ribs 1094 of the bearing 923 in reduced frictional contact with the handle 904. As previously discussed, the bearing 923 can bear against and/or rotate within the handle 904 to stabilize the drive shaft 920, such as by centering the drive shaft 920 and/or maintaining alignment of a central or rotational axis of the drive shaft 920 and a longitudinal axis of the handle. Further, the distal end of the drive shaft 920 can directly bear against and/or rotate within the opening 980 of the distal cap 905 for stabilization and or centering.

When the distally directed force is removed from the handle 904, the driver 901 can return to the orientation depicted in FIGS. 45 and 46. Whether before, after, or instead of actuating the driver 901 to operate in an automated or powered mode, the user may use the driver 901 in a fully manual mode. The user can press distally on the cover or cap 903 to urge an access assembly distally relative to the bone. Pressing on the cap 903 directly transfers the downward or distal force to the drive shaft 920. A user may additionally twist the handle 904 (e.g., in a single direction or back and forth) while pressing downward in this manner. The user may grip both the cap 903 and the handle 904 during such manipulation, which can tend to keep these components rotationally locked. Moreover, the clutch 922 and the stop 924 can remain engaged due to the absence of any differential forces between the cap 903 and the handle 904 that exceed the actuation force of the compression spring 934. By applying a distal force to the cap 903 in this manner, the medical driver can be used in the fully manual mode, independent of whether the torsion spring 914 is in the loaded state, and thus provides a rotational bias to the system, or in the unloaded state without providing any rotational bias.

Figure 49:
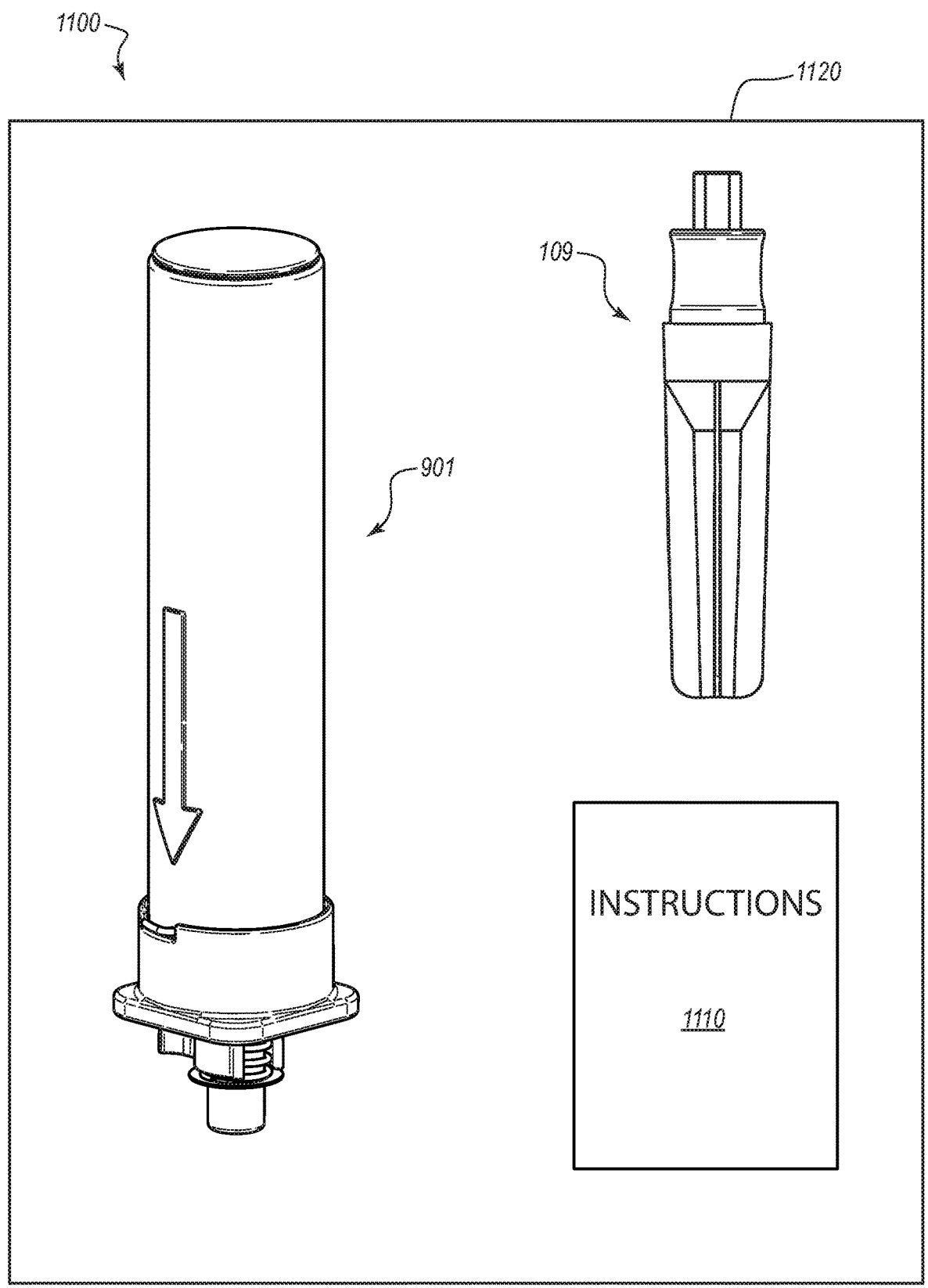
FIG. 49 depicts an embodiment of a kit that includes the driver of FIG. 29, shown in perspective, and an access assembly and instructions for use, shown in elevation.

FIG. 49 depicts an embodiment of a kit 1100 for accessing the interior of a bone, or stated otherwise, depicts an embodiment of an intraosseous access kit 1100. The kit 1100 can include any of the systems disclosed herein (e.g., the system 100) and/or components thereof (e.g., any of the drivers 101, 501, 701, 901), or alternative components therefor. For example, in the illustrated embodiment, the kit 1100 includes the driver 901 and the access assembly 109, each described above, which can be used together to achieve intraosseous access in manners such as previously described.

The kit 1100 can include instructions for use 1110, which may provide directions with respect to any of the methods or processes disclosed herein. In various embodiments, the kit 1100—and, in particular, the instructions for use 1110 thereof—can be approved of or authorized by a regulating body of a particular jurisdiction. For example, the kit 1100, and the instructions for use 1110 thereof, may be approved of or authorized by the Food and Drug Administration of the United States of America and/or may comply with the regulations of other jurisdictions, such as by qualifying for CE marking in the European Union.

The kit 1100 may further include packaging 1120 of any suitable variety that contains the driver 901, the access assembly 109, and the instructions for use 1110. In some embodiments, the instructions for use 1110 are physically contained within the packaging 1120. In other or further embodiments, the instructions for use 1110 are printed on the packaging 1120.

Following is a nonlimiting example of an embodiment of a driver consistent with the present disclosure.

EXAMPLE

A driver was constructed consistent with the design depicted in FIGS. 29-48.

A power drill was used to perform tests to determine the amount of user applied force vs. the drill torque for penetrating the cortex into the bone marrow. Based on that data, a linear average relationship between user applied force and drill torque was determined to be approximately:

$TF$=Torque/Force $TF$=0.0045/m

The desired torque for the spring could therefore be calculated to overcome the maximum torque at the at the maximum user applied force:

$F$max=44.5N

Torquemax=44.5N*0.0045/m

Torquemax=0.2 N·m or 200 N·mm

Additionally, the drill outputs were used to determine the average number of rotations required to penetrate the cortex into the bone marrow at a given force. The average number of rotations required at Fmax was 8 turns.

A factor of safety of 1.8 was added to the Torquemax to ensure that the spring driven drill would not stall during use.

Torquespring=200 N·mm*1.8=360 N·mm

Further consideration was given to the outside diameter of the device handle so that it satisfied usability. It was determined that the device preferably should not exceed an outside diameter of 30.5 mm to achieve a desirable usability. Given tolerances, the thickness of the handle, etc., the maximum diameter of the spring was limited to 25 mm.

The torsion spring that fit within the body of the unit, and provided the desired number of turns, and torsion, was determined to be:

TABLE 1

| | |
|---|---|
| Outer Diameter (OD) | 25 millimeters |
| Inner Diameter (ID) | 22.4 millimeters |
| Mean Diameter (D) | 23.7 millimeters |
| Number Coils (N) | 64 |
| Torsional Moment (M) | 360.64 N · mm |
| Deflection in Degrees (T) | 3600 (10 turns) |
| Wire Diameter (d) | 1.3 millimeters |

In order to not exceed the maximum user applied force, the linear actuation force required to activate the torsion spring was multiplied by 0.9. The thrust (compression) spring selected to achieve these requirements was determined to be:

TABLE 2

| | |
|---|---|
| Outer Diameter | 12.2 millimeters |
| Inner Diameter | 9.9 millimeters |
| Free Length | 19.1 millimeters |
| Wire Diameter | 1.1 millimeters |
| Total Coils | 5.25 |
| Max. Load | 40.7 newtons |

The preceding calculations are illustrative of one preferred starting point/max torque provided by the torsion spring (e.g., when in its packaged state as a pre-wound device).

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in any suitable manner. For example, this term is sufficiently broad to include the coupling of two features by virtue of their being defined by, formed on, or otherwise present on a single, unitary, or monolithic component. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of"

an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:
1. A medical driver comprising:
a handle;
a drive shaft coupled to the handle, the drive shaft being configured to couple with an access assembly for drilling into bone, the drive shaft further being configured to be displaced relative to the handle from a rotationally restricted state in which the drive shaft is rotationally restricted relative to the handle to a drilling state in which the drive shaft is freely rotatable in at least one direction relative to the handle;
a mechanical energy-storage device coupled to the drive shaft, the energy-storage device being configured to automatically rotate the drive shaft relative to the handle upon transition of the drive shaft to the drilling state; and
a biasing element coupled to the handle and to the drive shaft, the biasing element being configured to provide a bias to maintain the drive shaft in the rotationally restricted state,
wherein, when distal movement of the drive shaft is opposed, application of a distally directed force on the handle in an amount sufficient to overcome the bias of the biasing element transitions the drive shaft to the drilling state to automatically permit the energy-storage device to rotate the drive shaft relative to the handle.
2. The medical driver of claim 1, wherein the drive shaft is translatable relative to the handle between the rotationally restricted and drilling states.
3. The medical driver of claim 2, wherein the drive shaft is restricted to longitudinal translation without rotational movement relative to the handle when the drive shaft is being transitioned from the rotationally restricted state to the drilling state.

4. The medical driver of claim 1, further comprising a stop coupled with the handle and a stopping surface coupled with the drive shaft, wherein the stop engages the stopping surface to rotationally fix the drive shaft relative to the handle when the drive shaft is in the rotationally restricted state.

5. The medical driver of claim 4, wherein said application of a proximally directed force on the drive shaft in an amount sufficient to overcome the bias of the biasing element displaces the drive shaft proximally in an amount sufficient to disengage the stopping surface from the stop to transition the drive shaft to the drilling state.

6. The medical driver of claim 5, wherein the biasing element comprises a compression spring of which a proximal end is coupled with the handle and a distal end is coupled with the drive shaft.

7. The medical driver of claim 1, wherein at least a portion of a proximal end of the drive shaft is positioned proximal to a proximal end of the handle in at least the drilling state of the drive shaft.

8. The medical driver of claim 1, further comprising a bearing coupled to the drive shaft to substantially maintain alignment of a rotational axis of the drive shaft with a longitudinal axis of the medical driver during rotation of the drive shaft relative to the handle when the drive shaft is in the drilling state.

9. The medical driver of claim 8, wherein a cap comprises the bearing.

10. The medical driver of claim 1, further comprising a cap coupled to the drive shaft.

11. The medical driver of claim 10, wherein the cap is fixedly attached to the drive shaft.

12. The medical driver of claim 1, further comprising a retainer coupled to the handle and the drive shaft that is configured to restrict longitudinal movement of the handle relative to the drive shaft to thereby maintain the drive shaft in the rotationally restricted state.

13. The medical driver of claim 1, wherein the mechanical energy-storage device comprises a torsion spring.

14. The medical driver of claim 13, wherein the torsion spring defines a longitudinal channel, and wherein the drive shaft extends longitudinally through at least a portion of the longitudinal channel.

15. The medical driver of claim 14, wherein the drive shaft extends longitudinally through an entirety of the longitudinal channel.

16. The medical driver of claim 13, wherein the torsion spring defines a longitudinal channel, and wherein the drive shaft is positioned entirely external to the longitudinal channel.

17. A system comprising:
the medical driver of claim 1; and
the access assembly for drilling into bone.

18. A kit comprising:
the medical driver of claim 1;
the access assembly for drilling into bone; and
instructions for using the medical driver, wherein the instructions comprise directions to:
couple the access assembly to the drive shaft of the medical driver;
advance the handle in a distal direction through the skin of a patient to bring the access assembly into contact with a bone of the patient;
continue advancing the handle in a distal direction as the bone resists distal movement of the drive shaft to overcome the bias provided by the biasing element to thereby transition the drive shaft to the drilling state; and
drill a portion of the access assembly through the cortical layer of the bone while the mechanical energy-storage device automatically rotates the drive shaft after the drive shaft has been transitioned to the drilling state.

19. A medical driver comprising:
a handle;
a stop coupled to the handle;
a drive shaft coupled to the handle so as to translate relative to the handle between a rotationally restricted state and a drilling state, the drive shaft being configured to couple with an access assembly for drilling into bone;
a stopping surface coupled with the drive shaft; and
a preloaded mechanical energy-storage device coupled to the drive shaft so as to provide a rotational bias to the drive shaft, wherein the stop and the stopping surface cooperate to oppose the rotational bias when the drive shaft is in the rotationally restricted state, and wherein translation of the drive shaft to the drilling state disengages the stop and the stopping surface from each other to permit the energy-storage device to automatically rotate the drive shaft relative to the handle.

20. A medical driver comprising:
a handle;
a drive shaft coupled to the handle in a first state in which the drive shaft is rotationally restricted relative to the handle, the drive shaft being configured to couple with an access assembly for drilling into bone, the drive shaft further being configured to be displaced relative to the handle to a second state in which the drive shaft is freely rotatable in at least one direction relative to the handle;
a mechanical energy-storage device coupled to the drive shaft, the mechanical energy-storage device being configured to automatically rotate the drive shaft relative to the handle upon transition of the drive shaft to the second state; and
a biasing element coupled to the handle and the drive shaft, the biasing element providing a bias to maintain the drive shaft in the first state,
wherein application of a proximally directed force on the drive shaft in an amount sufficient to overcome the bias provided by the biasing element transitions the drive shaft to the second state to automatically permit the mechanical energy-storage device to rotate the drive shaft relative to the handle.

* * * * *